United States Patent
Nguyen et al.

(10) Patent No.: US 8,267,945 B2
(45) Date of Patent: Sep. 18, 2012

(54) CLIP ADVANCER WITH LOCKOUT MECHANISM

(75) Inventors: Anthony T. Nguyen, West Chester, OH (US); Denzel Z. Herrera-Davis, Cincinnati, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 346 days.

(21) Appl. No.: 12/628,662

(22) Filed: Dec. 1, 2009

(65) Prior Publication Data
US 2011/0087243 A1 Apr. 14, 2011

Related U.S. Application Data

(63) Continuation-in-part of application No. 12/576,736, filed on Oct. 9, 2009.

(51) Int. Cl.
*A61B 17/10* (2006.01)
(52) U.S. Cl. ...................................................... 606/143
(58) Field of Classification Search .............. 606/75, 606/139, 142, 219, 143; 227/175.1
See application file for complete search history.

(56) References Cited

U.S. PATENT DOCUMENTS

| | | | |
|---|---|---|---|
| 2,968,041 A | 1/1961 | Skold | |
| 3,459,029 A | 8/1969 | Rosenfeld et al. | |
| 4,038,987 A | 8/1977 | Komiya | |
| 4,064,881 A | 12/1977 | Meredith | |
| 4,080,820 A | 3/1978 | Allen | |
| 4,152,920 A | 5/1979 | Green | |
| 4,188,953 A | 2/1980 | Klieman et al. | |
| 4,242,902 A | 1/1981 | Green | |
| 4,296,751 A | 10/1981 | Blake, III et al. | |
| 4,298,072 A | 11/1981 | Baker et al. | |
| 4,372,316 A | 2/1983 | Blake, III et al. | |
| 4,408,603 A | 10/1983 | Blake, III et al. | |
| 4,448,193 A | 5/1984 | Ivanov | |
| 4,449,530 A | 5/1984 | Bendel et al. | |

(Continued)

FOREIGN PATENT DOCUMENTS

DE 3490145 5/1985

(Continued)

OTHER PUBLICATIONS

U.S. Appl. No. 12/576,736, filed Oct. 9, 2009, Clip Advancer.

(Continued)

*Primary Examiner* — Julian Woo
(74) *Attorney, Agent, or Firm* — Nutter McClennen & Fish LLP

(57) ABSTRACT

A surgical clip applier and methods for applying surgical clips to a vessel, duct, shunt, etc., during a surgical procedure are provided. In one embodiment, a surgical clip applier is provided and can include a housing having a trigger movably coupled thereto and an elongate shaft extending therefrom with opposed jaws formed on a distal end thereof. The clip applier can include an advancer assembly disposed within the elongate shaft and configured to advance one of a plurality of clips disposed within the elongate shaft into the opposed jaws. A feeder shoe can be disposed within the elongate shaft and can be configured to engage and prevent the advancer assembly from moving to a proximal position after the advancer assembly has moved to a distal position to advance a proximal-most clip into the opposed jaws. This can indicate to a user that a clip supply of the surgical clip applier is depleted.

20 Claims, 60 Drawing Sheets

U.S. PATENT DOCUMENTS

| | | |
|---|---|---|
| 4,452,376 A | 6/1984 | Klieman et al. |
| 4,513,746 A | 4/1985 | Aranyi et al. |
| 4,522,207 A | 6/1985 | Klieman et al. |
| 4,532,925 A | 8/1985 | Blake, III |
| 4,556,058 A | 12/1985 | Green |
| 4,557,263 A | 12/1985 | Green |
| 4,576,165 A | 3/1986 | Green et al. |
| 4,588,580 A | 5/1986 | Gale et al. |
| 4,590,937 A | 5/1986 | Deniega |
| 4,611,595 A | 9/1986 | Klieman et al. |
| 4,616,650 A | 10/1986 | Green et al. |
| 4,651,737 A | 3/1987 | Deniega |
| 4,662,374 A | 5/1987 | Blake, III |
| 4,674,504 A | 6/1987 | Klieman et al. |
| 4,676,504 A | 6/1987 | Ponza |
| 4,702,274 A | 10/1987 | Kramer |
| 4,712,549 A | 12/1987 | Peters et al. |
| 4,741,336 A | 5/1988 | Failla et al. |
| 4,799,481 A | 1/1989 | Transue et al. |
| 4,834,096 A | 5/1989 | Oh et al. |
| 4,844,066 A | 7/1989 | Stein |
| 4,850,355 A | 7/1989 | Brooks et al. |
| 4,976,722 A | 12/1990 | Failla |
| 4,979,950 A | 12/1990 | Transue et al. |
| 5,009,661 A | 4/1991 | Michelson |
| 5,012,666 A | 5/1991 | Chen et al. |
| 5,030,226 A | 7/1991 | Green et al. |
| 5,047,038 A | 9/1991 | Peters et al. |
| 5,049,152 A | 9/1991 | Simon et al. |
| 5,062,846 A | 11/1991 | Oh et al. |
| 5,084,057 A | 1/1992 | Green et al. |
| 5,086,901 A | 2/1992 | Petronis et al. |
| 5,100,416 A | 3/1992 | Oh et al. |
| 5,100,420 A | 3/1992 | Green et al. |
| 5,104,395 A | 4/1992 | Thornton et al. |
| 5,112,343 A | 5/1992 | Thornton |
| 5,116,349 A | 5/1992 | Aranyi |
| 5,127,730 A | 7/1992 | Brelje et al. |
| 5,129,885 A | 7/1992 | Green et al. |
| 5,156,609 A | 10/1992 | Nakao et al. |
| 5,163,945 A | 11/1992 | Ortiz et al. |
| 5,171,247 A * | 12/1992 | Hughett et al. ............... 606/142 |
| 5,171,249 A | 12/1992 | Stefanchik et al. |
| 5,190,203 A | 3/1993 | Rodak |
| 5,192,288 A | 3/1993 | Thompson et al. |
| 5,197,970 A | 3/1993 | Green et al. |
| 5,201,746 A | 4/1993 | Shichman |
| 5,222,961 A | 6/1993 | Nakao et al. |
| 5,232,450 A | 8/1993 | Green et al. |
| 5,246,450 A | 9/1993 | Thornton et al. |
| 5,269,792 A | 12/1993 | Kovac et al. |
| 5,270,171 A | 12/1993 | Cercek et al. |
| 5,282,807 A | 2/1994 | Knoepfler |
| 5,282,808 A | 2/1994 | Kovac et al. |
| 5,286,255 A | 2/1994 | Weber |
| 5,300,081 A | 4/1994 | Young et al. |
| 5,306,149 A | 4/1994 | Schmid et al. |
| 5,336,232 A | 8/1994 | Green et al. |
| 5,354,304 A | 10/1994 | Allen et al. |
| 5,358,506 A | 10/1994 | Green et al. |
| 5,366,458 A | 11/1994 | Korthoff et al. |
| 5,382,254 A | 1/1995 | McGarry et al. |
| 5,382,255 A | 1/1995 | Castro et al. |
| 5,383,880 A | 1/1995 | Hooven |
| 5,383,881 A | 1/1995 | Green et al. |
| 5,395,381 A | 3/1995 | Green et al. |
| 5,403,326 A | 4/1995 | Harrison et al. |
| 5,403,327 A | 4/1995 | Thornton et al. |
| 5,409,498 A | 4/1995 | Braddock et al. |
| 5,423,835 A | 6/1995 | Green et al. |
| 5,431,667 A | 7/1995 | Thompson et al. |
| 5,431,668 A | 7/1995 | Burbank, III et al. |
| 5,431,669 A | 7/1995 | Thompson et al. |
| 5,433,721 A | 7/1995 | Hooven et al. |
| 5,434,081 A | 7/1995 | Maekawa |
| 5,439,156 A | 8/1995 | Grant et al. |
| 5,468,250 A | 11/1995 | Paraschac et al. |
| 5,470,007 A | 11/1995 | Plyley et al. |
| 5,474,732 A | 12/1995 | Korthoff et al. |
| 5,484,095 A | 1/1996 | Green et al. |
| 5,484,451 A | 1/1996 | Akopov et al. |
| 5,496,333 A | 3/1996 | Sackier et al. |
| 5,497,933 A | 3/1996 | DeFonzo et al. |
| 5,499,998 A | 3/1996 | Meade |
| 5,501,693 A | 3/1996 | Gravener |
| 5,509,920 A | 4/1996 | Phillips et al. |
| 5,514,149 A | 5/1996 | Green et al. |
| 5,527,318 A | 6/1996 | McGarry |
| 5,527,319 A | 6/1996 | Green et al. |
| 5,527,320 A | 6/1996 | Carruthers et al. |
| 5,547,117 A | 8/1996 | Hamblin et al. |
| 5,547,474 A | 8/1996 | Kloeckl et al. |
| 5,562,694 A | 10/1996 | Sauer et al. |
| 5,575,206 A | 11/1996 | Szyszko |
| 5,575,806 A | 11/1996 | Nakao et al. |
| 5,580,067 A | 12/1996 | Hamblin et al. |
| 5,582,615 A | 12/1996 | Foshee et al. |
| 5,582,617 A | 12/1996 | Klieman et al. |
| 5,591,178 A | 1/1997 | Green et al. |
| 5,601,224 A | 2/1997 | Bishop et al. |
| 5,601,573 A | 2/1997 | Fogelberg et al. |
| 5,605,272 A | 2/1997 | Witt et al. |
| 5,607,273 A | 3/1997 | Kecmer et al. |
| 5,607,436 A | 3/1997 | Pratt et al. |
| 5,618,291 A | 4/1997 | Thompson et al. |
| 5,624,452 A | 4/1997 | Yates |
| 5,625,592 A | 4/1997 | Shinozaki |
| 5,626,585 A | 5/1997 | Mittelstadt et al. |
| 5,626,586 A | 5/1997 | Pistl et al. |
| 5,630,539 A | 5/1997 | Plyley et al. |
| RE35,525 E | 6/1997 | Stefanchik et al. |
| 5,634,930 A | 6/1997 | Thornton et al. |
| 5,643,291 A | 7/1997 | Pier et al. |
| 5,645,551 A | 7/1997 | Green et al. |
| 5,667,517 A | 9/1997 | Hooven |
| 5,673,841 A | 10/1997 | Schulze et al. |
| 5,681,330 A | 10/1997 | Hughett et al. |
| 5,695,502 A | 12/1997 | Pier et al. |
| 5,697,543 A | 12/1997 | Burdorff |
| 5,700,270 A | 12/1997 | Peyser et al. |
| 5,700,271 A | 12/1997 | Whitfield et al. |
| 5,706,824 A | 1/1998 | Whittier |
| 5,713,911 A | 2/1998 | Racenet et al. |
| 5,720,756 A | 2/1998 | Green et al. |
| 5,725,537 A | 3/1998 | Green et al. |
| 5,725,538 A | 3/1998 | Green et al. |
| 5,749,881 A | 5/1998 | Sackier et al. |
| 5,755,726 A | 5/1998 | Pratt et al. |
| 5,772,673 A | 6/1998 | Cuny et al. |
| 5,776,147 A | 7/1998 | Dolendo |
| 5,792,149 A | 8/1998 | Sherts et al. |
| 5,792,150 A | 8/1998 | Pratt et al. |
| 5,792,165 A | 8/1998 | Klieman et al. |
| 5,794,834 A | 8/1998 | Hamblin et al. |
| 5,830,221 A | 11/1998 | Stein et al. |
| 5,833,695 A | 11/1998 | Yoon |
| 5,833,696 A | 11/1998 | Whitfield et al. |
| 5,833,881 A | 11/1998 | Roe |
| 5,843,097 A | 12/1998 | Mayenberger et al. |
| 5,843,101 A | 12/1998 | Fry |
| 5,849,019 A | 12/1998 | Yoon |
| 5,855,311 A | 1/1999 | Hamblin et al. |
| 5,868,759 A | 2/1999 | Peyser et al. |
| 5,868,761 A | 2/1999 | Nicholas et al. |
| 5,869,435 A | 2/1999 | Kelly et al. |
| 5,895,394 A | 4/1999 | Kienzle et al. |
| 5,902,312 A | 5/1999 | Frater et al. |
| 5,904,693 A | 5/1999 | Dicesare et al. |
| 5,928,251 A | 7/1999 | Aranyi et al. |
| 5,938,667 A | 8/1999 | Peyser et al. |
| 5,941,439 A | 8/1999 | Kammerer et al. |
| 5,972,003 A | 10/1999 | Rousseau et al. |
| 5,993,465 A | 11/1999 | Shipp et al. |
| RE36,720 E | 5/2000 | Green et al. |
| 6,059,799 A | 5/2000 | Aranyi et al. |
| 6,063,097 A | 5/2000 | Oi et al. |
| 6,066,145 A | 5/2000 | Wurster |

| | | |
|---|---|---|
| 6,096,058 A | 8/2000 | Boche |
| 6,139,555 A | 10/2000 | Hart et al. |
| 6,152,920 A | 11/2000 | Thompson et al. |
| 6,217,590 B1 | 4/2001 | Levinson |
| 6,228,097 B1 | 5/2001 | Levinson et al. |
| 6,241,740 B1 | 6/2001 | Davis et al. |
| 6,277,131 B1 | 8/2001 | Kalikow |
| 6,306,149 B1 | 10/2001 | Meade |
| 6,306,150 B1 | 10/2001 | Levinson |
| 6,423,079 B1 | 7/2002 | Blake, III |
| 6,440,144 B1 | 8/2002 | Bacher |
| 6,458,142 B1 | 10/2002 | Faller et al. |
| 6,460,749 B1 | 10/2002 | Levinson et al. |
| 6,462,345 B1 | 10/2002 | Simon et al. |
| 6,507,400 B1 | 1/2003 | Pina et al. |
| 6,533,157 B1 | 3/2003 | Whitman |
| 6,537,289 B1 | 3/2003 | Kayan et al. |
| 6,544,271 B1 | 4/2003 | Adams et al. |
| 6,548,142 B1 | 4/2003 | Kar et al. |
| 6,548,796 B1 | 4/2003 | Silvermintz et al. |
| 6,549,275 B1 | 4/2003 | Cabuz et al. |
| 6,569,171 B2 | 5/2003 | DeGuillebon et al. |
| 6,589,792 B1 | 7/2003 | Malachowski |
| 6,597,438 B1 | 7/2003 | Cabuz et al. |
| 6,610,073 B1 | 8/2003 | Levinson |
| 6,646,742 B1 | 11/2003 | Gangstead et al. |
| 6,673,083 B1 | 1/2004 | Kayan et al. |
| 6,687,052 B1 | 2/2004 | Wilson et al. |
| 6,695,854 B1 | 2/2004 | Kayan et al. |
| 6,727,071 B1 | 4/2004 | Dunlay et al. |
| 6,752,823 B2 | 6/2004 | Prestel |
| 6,869,435 B2 | 3/2005 | Blake, III |
| 6,911,033 B2 | 6/2005 | de Guillebon et al. |
| 7,052,504 B2 | 5/2006 | Hughett |
| 7,211,092 B2 | 5/2007 | Hughett |
| 7,261,724 B2 | 8/2007 | Molitor et al. |
| 7,288,098 B2 | 10/2007 | Huitema et al. |
| 7,297,149 B2 | 11/2007 | Vitali et al. |
| 7,686,820 B2 | 3/2010 | Huitema et al. |
| 7,731,641 B1 | 6/2010 | Chen |
| 7,731,724 B2 | 6/2010 | Huitema et al. |
| 7,740,641 B2 | 6/2010 | Huitema |
| 8,038,686 B2 | 10/2011 | Huitema et al. |
| 8,075,571 B2 | 12/2011 | Vitali et al. |
| 2002/0099388 A1 | 7/2002 | Mayenberger |
| 2002/0123767 A1 | 9/2002 | Prestel |
| 2002/0128668 A1 | 9/2002 | Manetakis et al. |
| 2002/0138086 A1 | 9/2002 | Sixto et al. |
| 2002/0177863 A1 | 11/2002 | Mandel et al. |
| 2002/0198541 A1 | 12/2002 | Smith et al. |
| 2003/0014060 A1 | 1/2003 | Wilson et al. |
| 2003/0023249 A1 | 1/2003 | Manetakis |
| 2003/0040756 A1 | 2/2003 | Field |
| 2003/0040759 A1 | 2/2003 | de Guillebon et al. |
| 2003/0065358 A1 | 4/2003 | Frecker et al. |
| 2003/0069474 A1 | 4/2003 | Couvillon |
| 2003/0135224 A1 | 7/2003 | Blake |
| 2003/0191478 A1 | 10/2003 | Kortenbach et al. |
| 2004/0087979 A1 | 5/2004 | Field et al. |
| 2004/0097970 A1 | 5/2004 | Hughett |
| 2004/0097971 A1 | 5/2004 | Hughett |
| 2004/0097972 A1 | 5/2004 | Shipp et al. |
| 2004/0153107 A1 | 8/2004 | Kayan et al. |
| 2004/0167545 A1 | 8/2004 | Sadler et al. |
| 2006/0235437 A1 | 10/2006 | Vitali et al. |
| 2006/0235438 A1 | 10/2006 | Huitema et al. |
| 2006/0235439 A1 | 10/2006 | Molitor et al. |
| 2006/0235440 A1 | 10/2006 | Huitema et al. |
| 2006/0235441 A1 | 10/2006 | Huitema et al. |
| 2006/0235443 A1 | 10/2006 | Huitema et al. |
| 2006/0235444 A1 | 10/2006 | Huitema et al. |
| 2008/0004639 A1 | 1/2008 | Huitema et al. |
| 2008/0015615 A1 | 1/2008 | Molitor et al. |
| 2008/0027465 A1 | 1/2008 | Vitali et al. |
| 2008/0027466 A1 | 1/2008 | Vitali et al. |
| 2010/0185215 A1 | 7/2010 | Huitema et al. |
| 2010/0249804 A1 | 9/2010 | Huitema |
| 2011/0087241 A1 | 4/2011 | Nguyen |
| 2011/0087243 A1 | 4/2011 | Nguyen et al. |
| 2011/0218553 A1 | 9/2011 | Huitema et al. |
| 2011/0218555 A1 | 9/2011 | Huitema |
| 2011/0218556 A1 | 9/2011 | Nguyen et al. |
| 2011/0224696 A1 | 9/2011 | Huitema et al. |

FOREIGN PATENT DOCUMENTS

| | | |
|---|---|---|
| DE | 3152411 | 8/1986 |
| DE | 4015562 A1 | 11/1991 |
| DE | 4303544 A1 | 9/1993 |
| DE | 19534320 C1 | 2/1997 |
| DE | 19537299 A1 | 4/1997 |
| DE | 19643073 A1 | 4/1997 |
| DE | 19647354 A1 | 5/1998 |
| DE | 1993372 | 2/2001 |
| DE | 19933672 A1 | 2/2001 |
| EP | 090815 A1 | 10/1983 |
| EP | 152226 A1 | 8/1985 |
| EP | 409569 A1 | 1/1991 |
| EP | 0500353 A1 | 8/1992 |
| EP | 0 510 826 | 10/1992 |
| EP | 0510826 A1 | 10/1992 |
| EP | 0 671 148 A2 | 9/1995 |
| EP | 0674876 A2 | 10/1995 |
| EP | 0681810 | 11/1995 |
| EP | 0704190 | 3/1996 |
| EP | 0769274 | 4/1997 |
| EP | 0832605 A1 | 4/1998 |
| EP | 832605 A1 | 4/1998 |
| EP | 0834286 A1 | 4/1998 |
| EP | 0908152 | 4/1999 |
| EP | 908152 A1 | 4/1999 |
| EP | 1317906 A1 | 6/2003 |
| EP | 1405601 A1 | 4/2004 |
| EP | 1522264 A1 | 4/2005 |
| EP | 1537883 | 6/2005 |
| EP | 1764045 A1 | 3/2007 |
| FR | 900376 A | 6/1945 |
| JP | 59-067943 A | 4/1984 |
| JP | 62-002528 B | 1/1987 |
| JP | 05-505732 A | 8/1993 |
| JP | 07-047070 A | 2/1995 |
| JP | 07-213528 A | 8/1995 |
| JP | 07-308322 A | 11/1995 |
| JP | 2002-535030 A | 10/2002 |
| JP | 2004-500190 A | 1/2004 |
| JP | 2004-535236 A | 11/2004 |
| RU | 620263 | 6/1978 |
| SU | 620263 | 6/1978 |
| SU | 1560125 | 4/1990 |
| WO | WO-8910094 A1 | 11/1989 |
| WO | 9608203 | 3/1996 |
| WO | WO-9608203 A1 | 3/1996 |
| WO | WO-9902090 A1 | 1/1999 |
| WO | 0042922 A1 | 7/2000 |
| WO | WO-0042922 | 7/2000 |
| WO | WO-0042922 A1 | 7/2000 |
| WO | 0126705 | 4/2001 |
| WO | WO-0156455 A2 | 8/2001 |
| WO | WO-0215797 | 2/2002 |
| WO | WO-0215797 A1 | 2/2002 |
| WO | WO-0228268 | 4/2002 |
| WO | WO-0228268 A2 | 4/2002 |
| WO | 03005878 | 1/2003 |
| WO | WO-03/005911 A1 | 1/2003 |
| WO | WO-2004050971 A2 | 6/2004 |

OTHER PUBLICATIONS

U.S. Appl. No. 12/748,959, filed Mar. 29, 2010, Surgical Clip Applier Ratchet Mechanism.

Notice of Opposition filed in EP 1,764,044 on Feb. 4, 2010.

European Search Report for 06252080.4, dated Dec. 27, 2006 (6 Pages).

European Search Report for 06254800.3, dated Jan. 15, 2007 (6 Pages).

European Search Report for 06254801.1, dated Jan. 17, 2007 (6 Pages).

European Search Report for 10179717.3, dated Nov. 19, 2010 (5 Pages).

European Search Report for 10179743.9, dated Feb. 7, 2011 (10 Pages).
International Search Report for PCT/US 02/21609, dated Nov. 21, 2002 (3 Pages).
Partial European Search Report for 06252083.8, dated Dec. 27, 2006 (4 Pages).
Partial European Search Report for 10179741.3, dated Nov. 5, 2010 (6 Pages).
U.S. Appl. No. 12/576,736, Nguyen et al.
U.S. Appl. No. 12/635,990, Cropper et al.
U.S. Appl. No. 12/748,959, Huitema et al.
Auto Suture Premium Surgiclip Titanium Disposable Automatic Clip Appliers, U.S. Surgical Corporation, Copyright 1988.
European Search Report for 0625479.3, dated Feb. 16, 2009. (8 pages).
Singapore Supplementary Search Report for 0602116-6, dated Feb. 9, 2009. (6 pages).
European Search Report for 06254793.0, dated Oct. 1, 2009. (6 pages).
Singapore Written Opinion for 0806148-3, dated Oct. 19 2009. (5 pages).
Japanese Office Action issued Nov. 29, 2011 for Application No. 2006-111085 (3 Pages).
Japanese Office Action issued Aug. 30, 2011 for Application No. 2006-249658 (3 Pages).

* cited by examiner

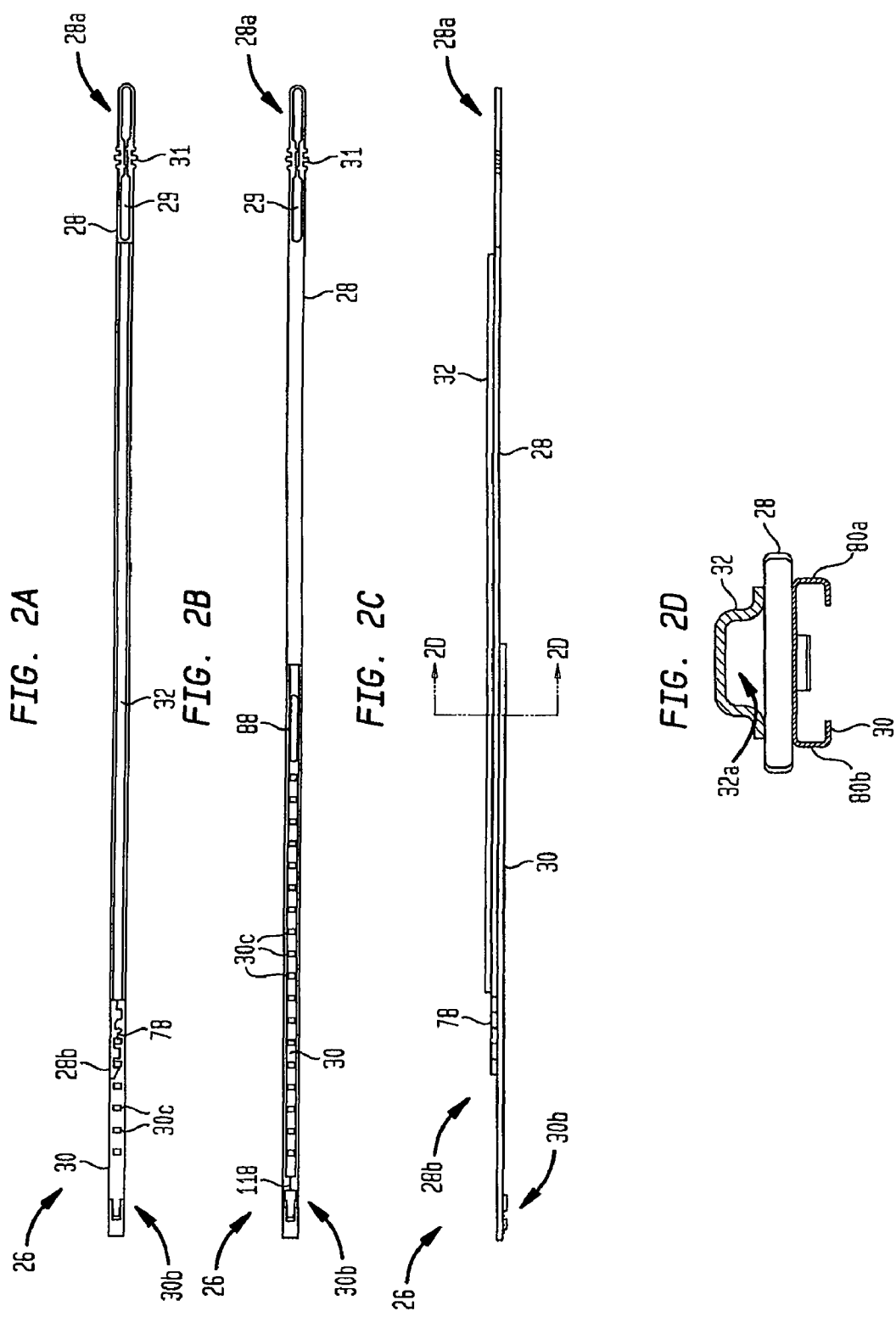

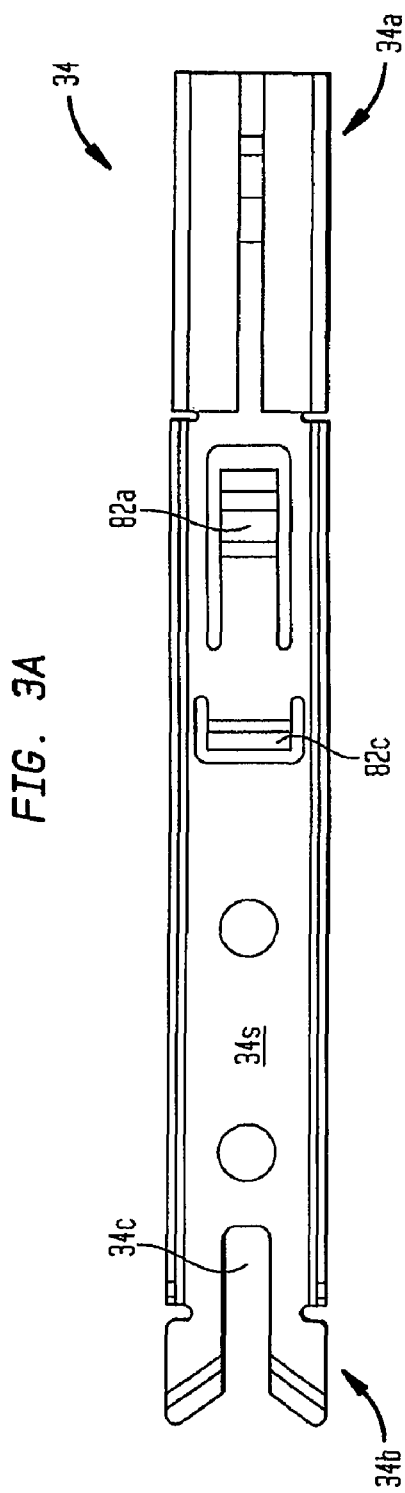
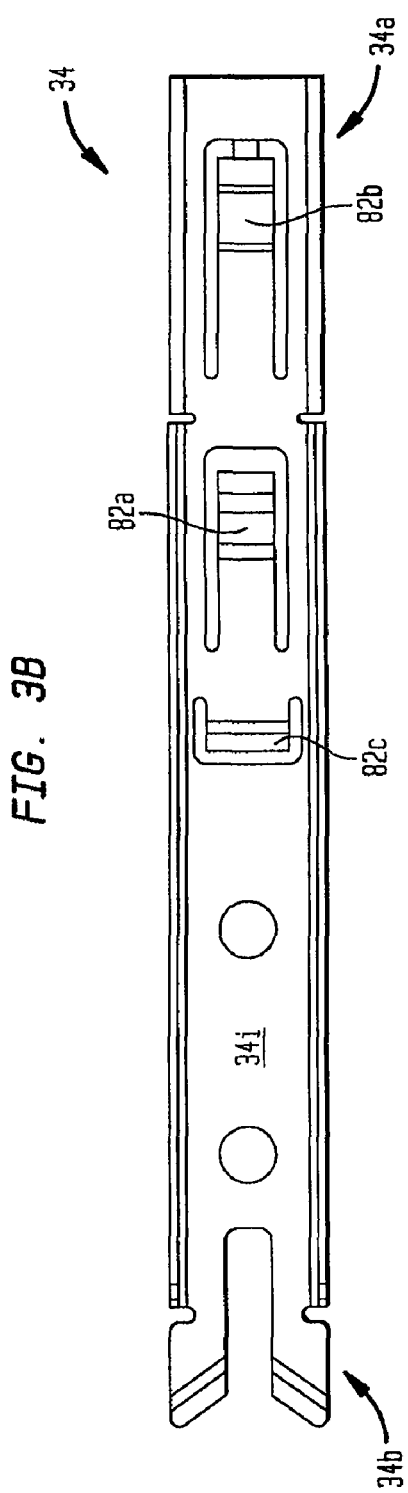

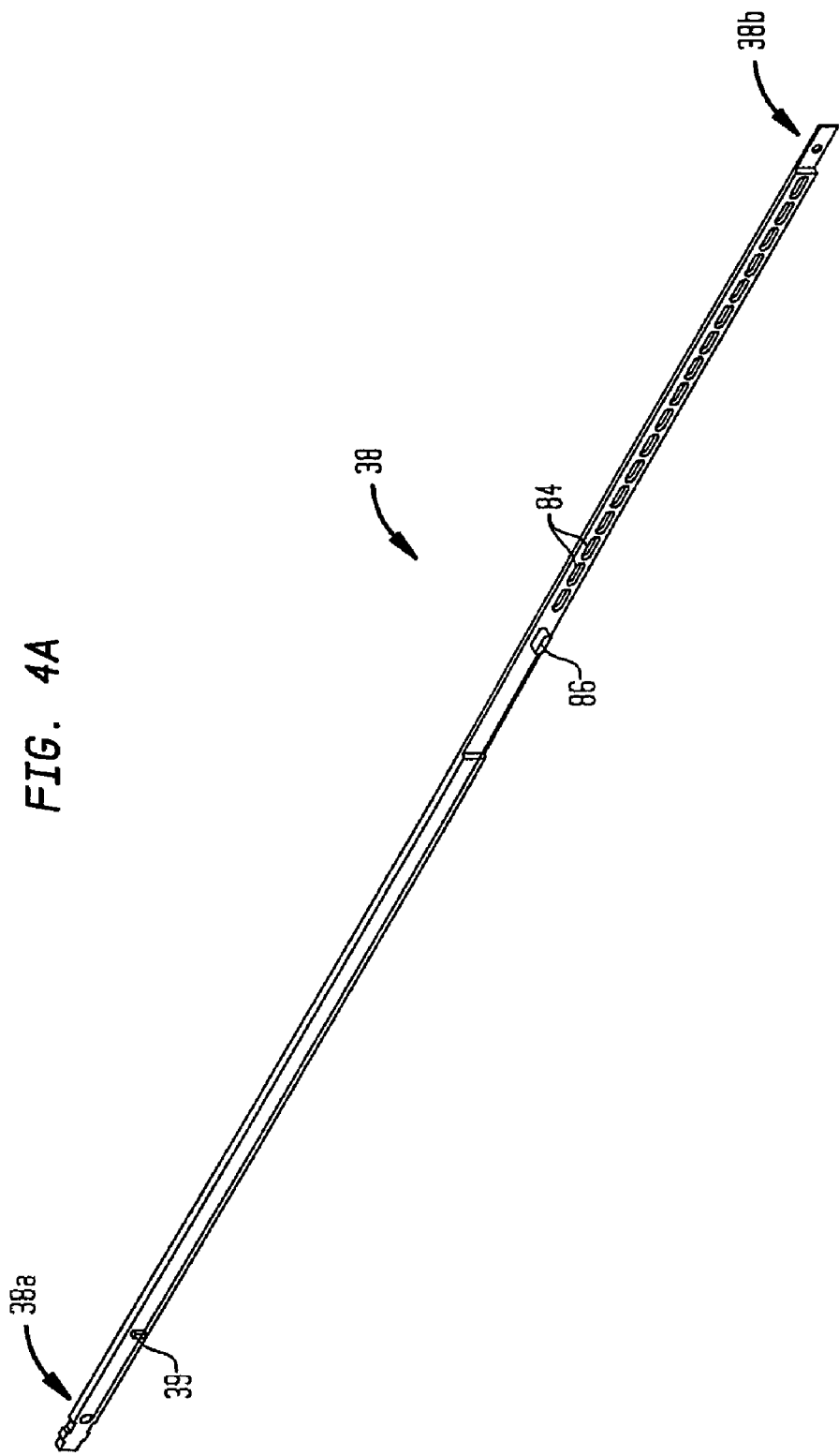

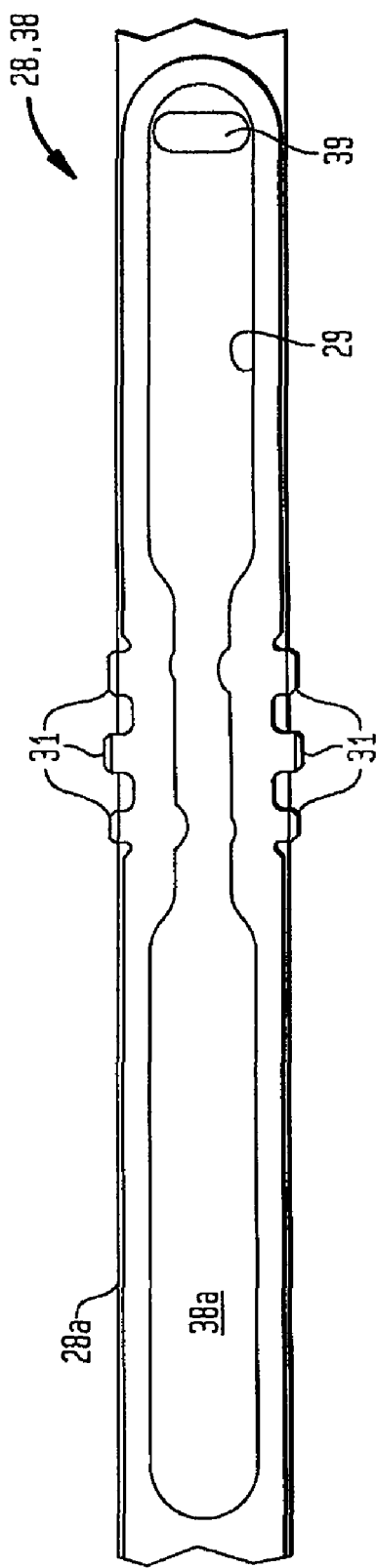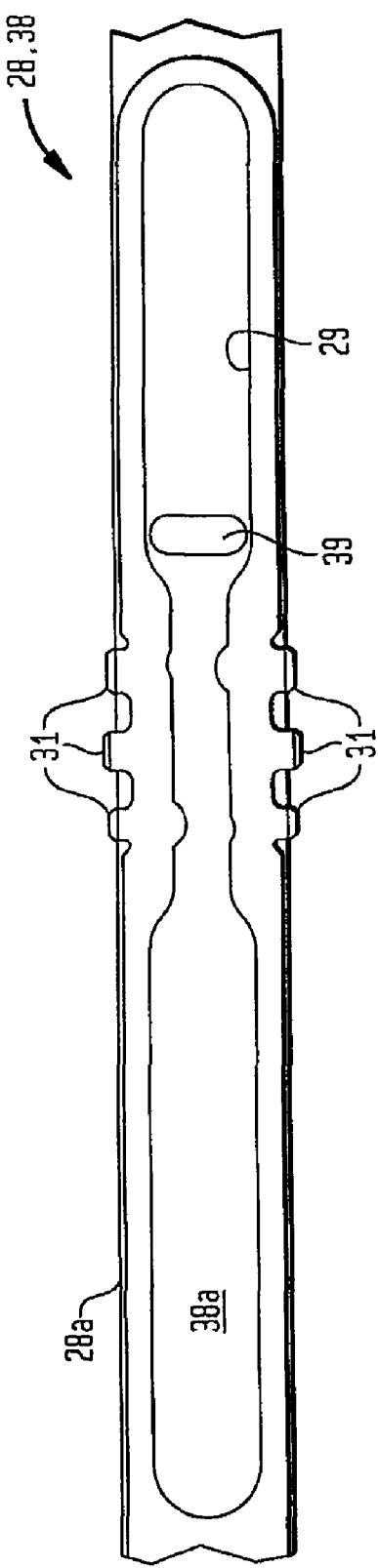

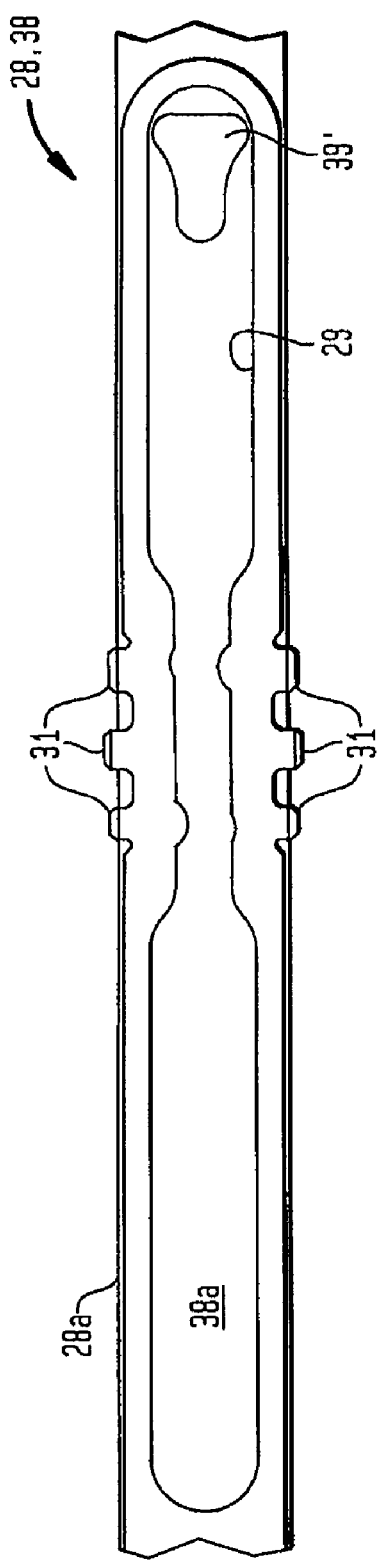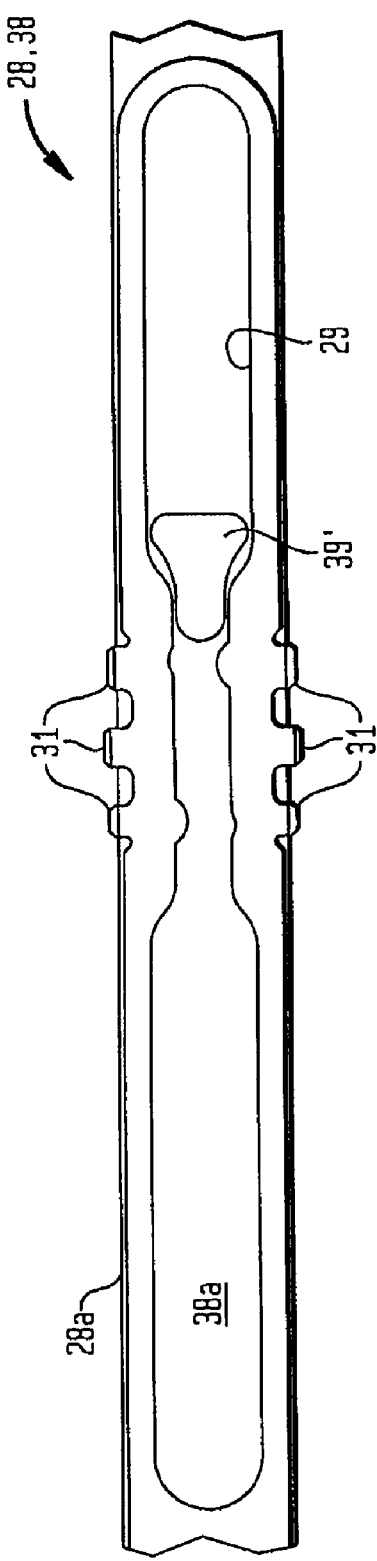

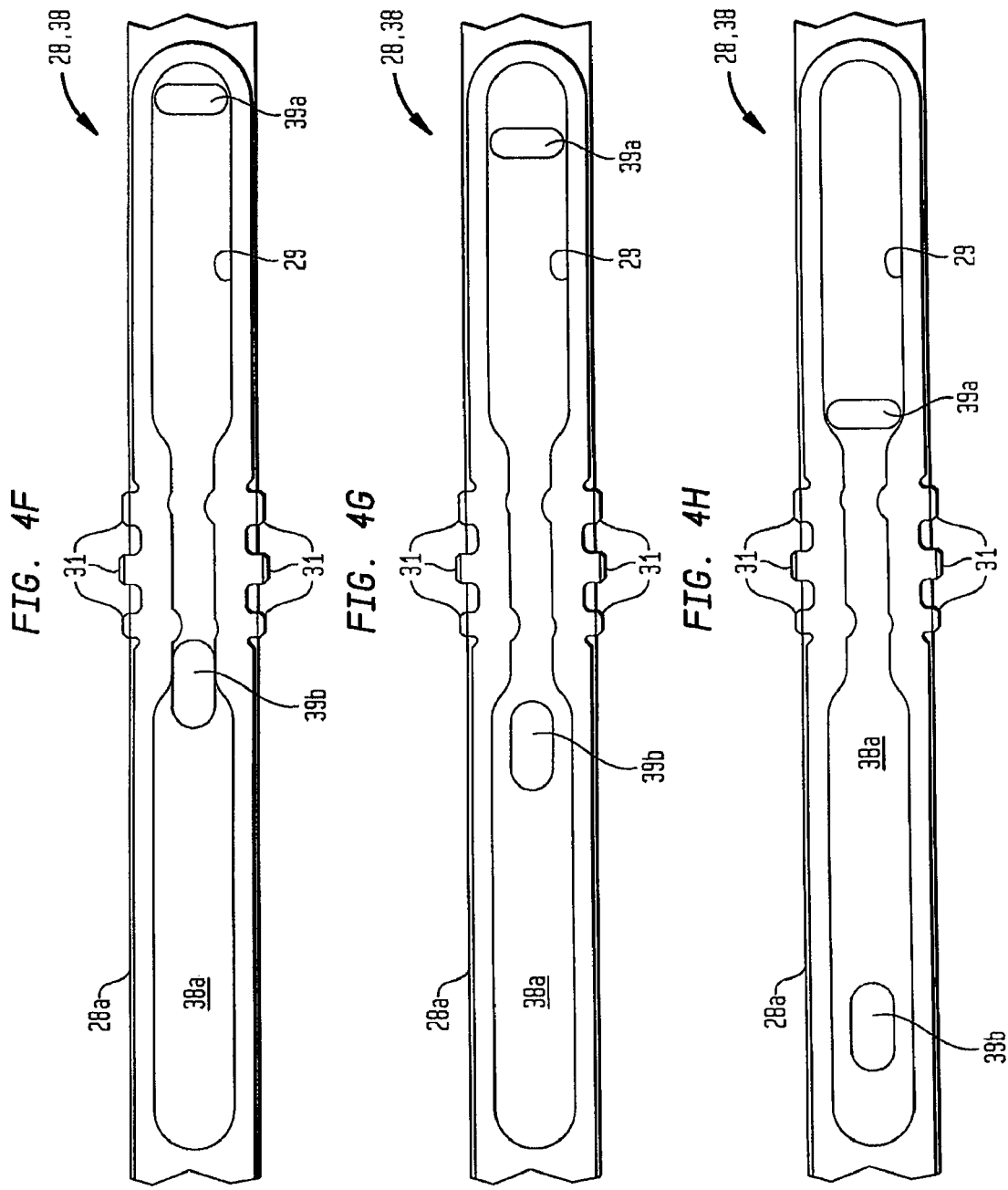

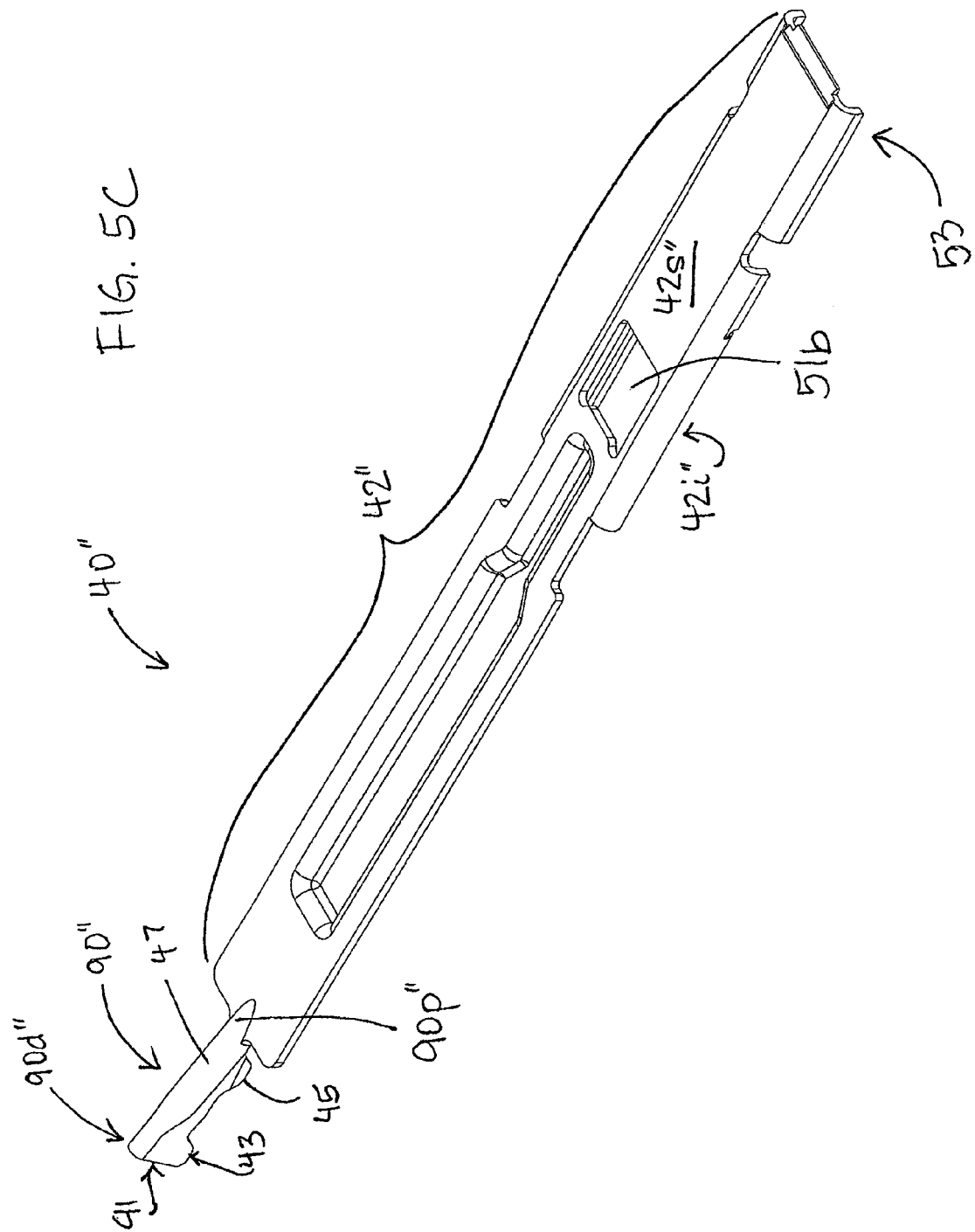

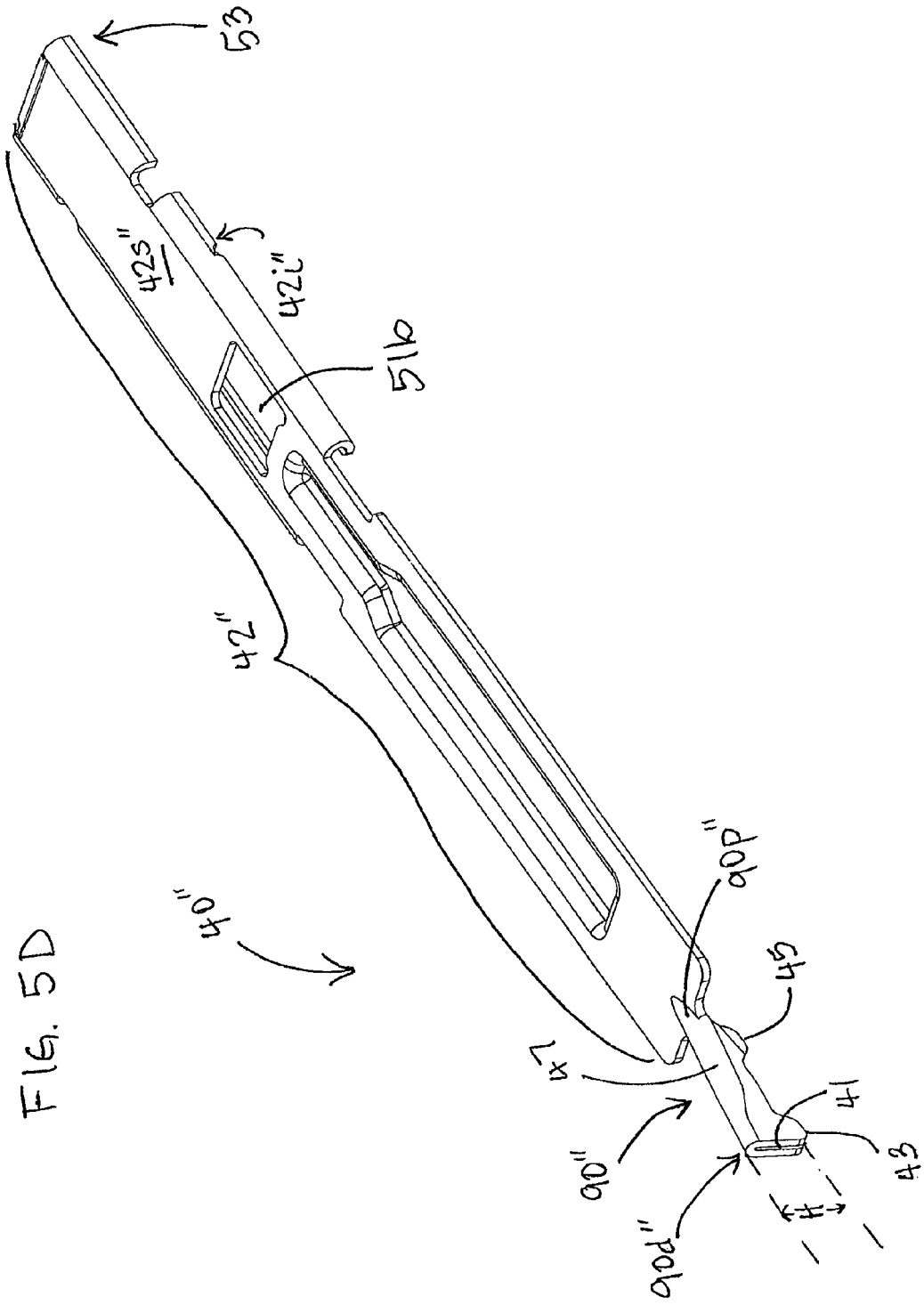

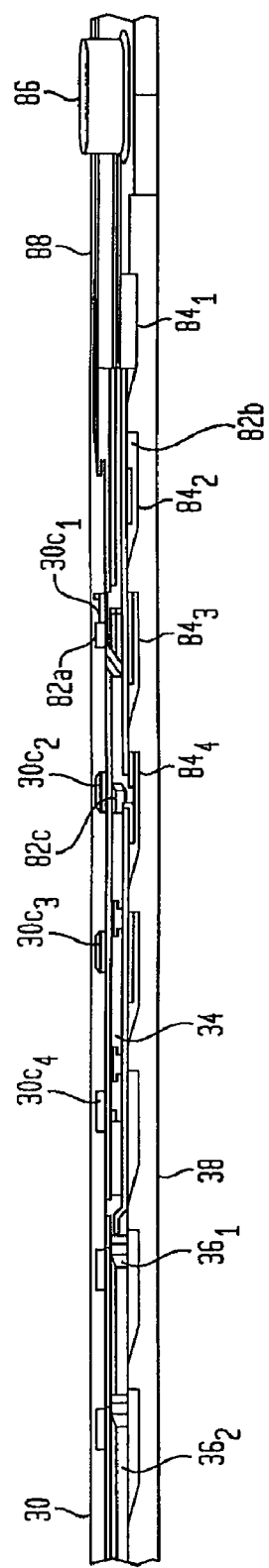
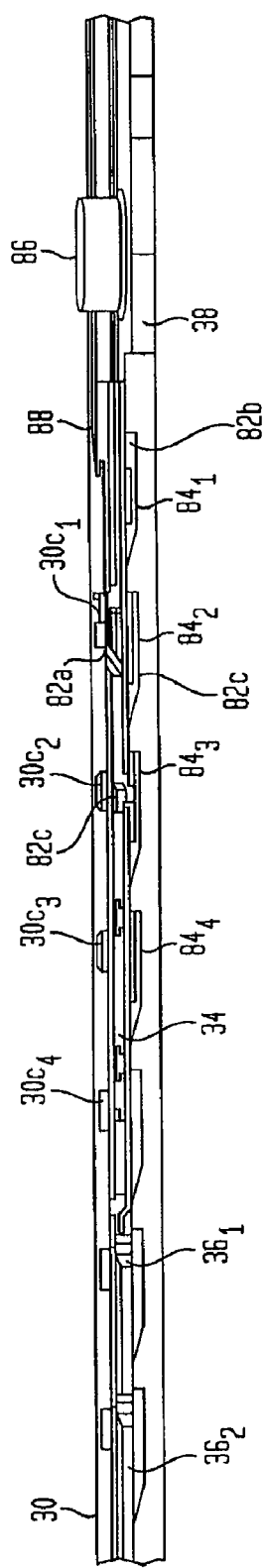
FIG. 6A
FIG. 6B

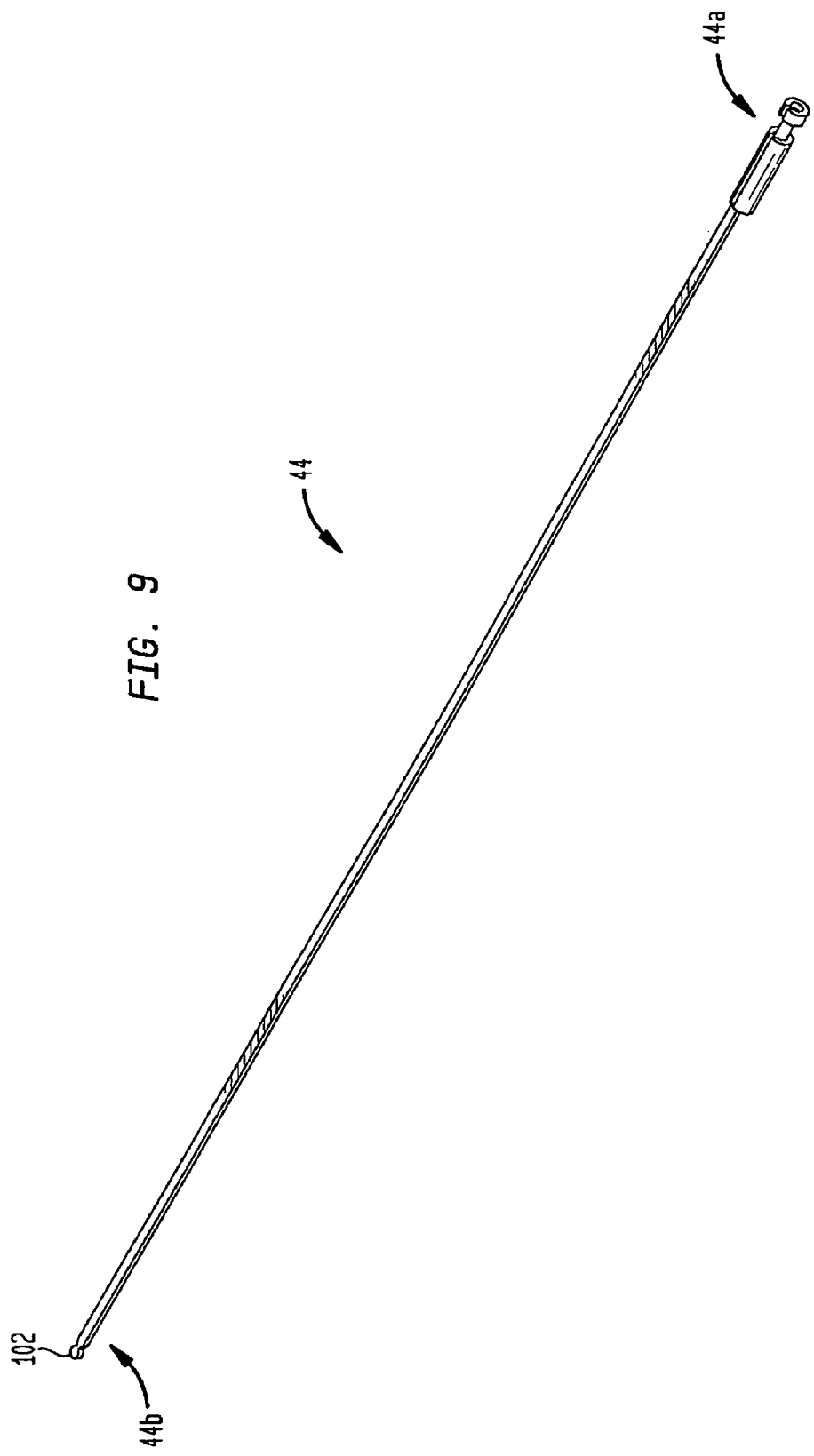

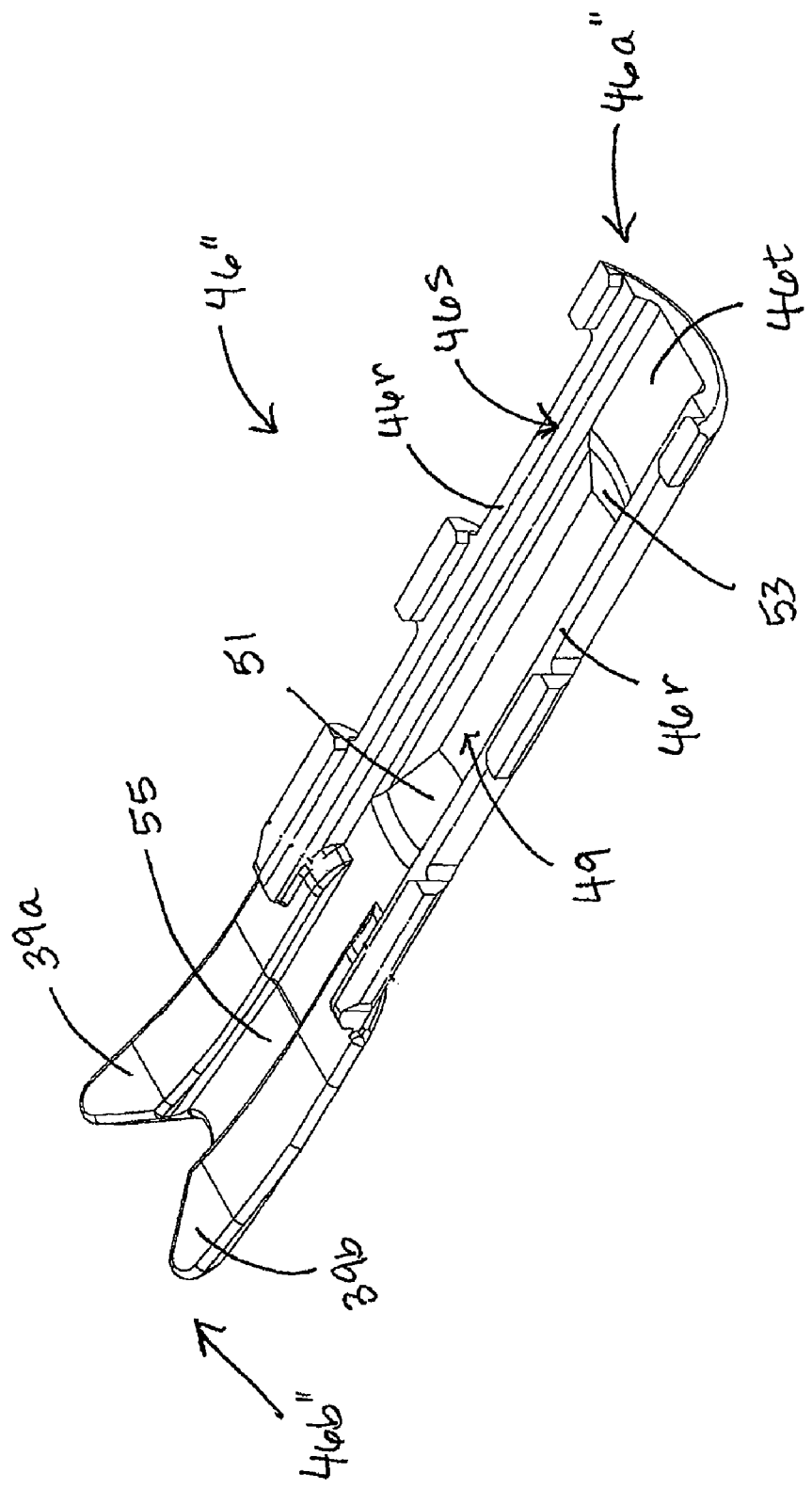

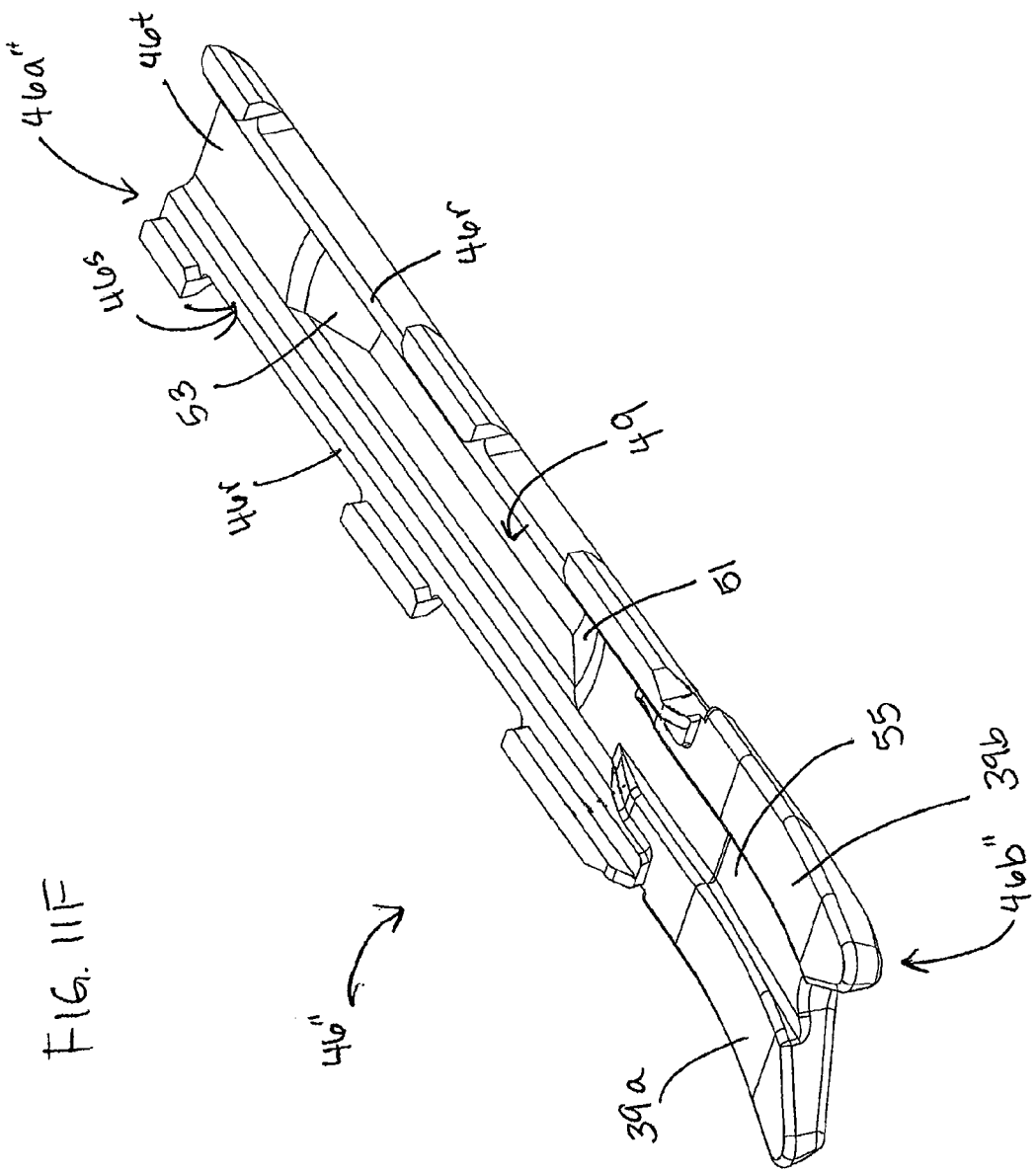

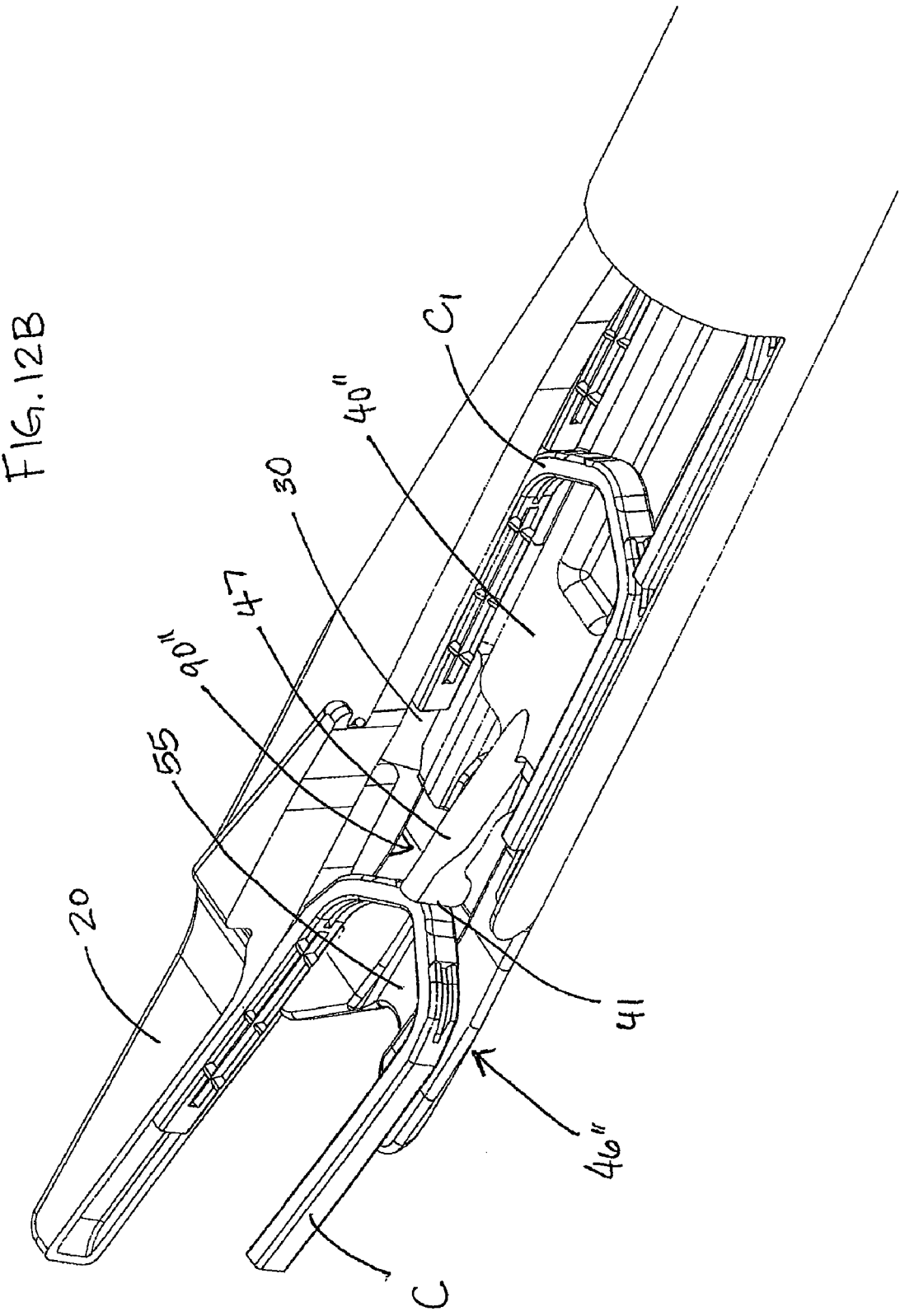

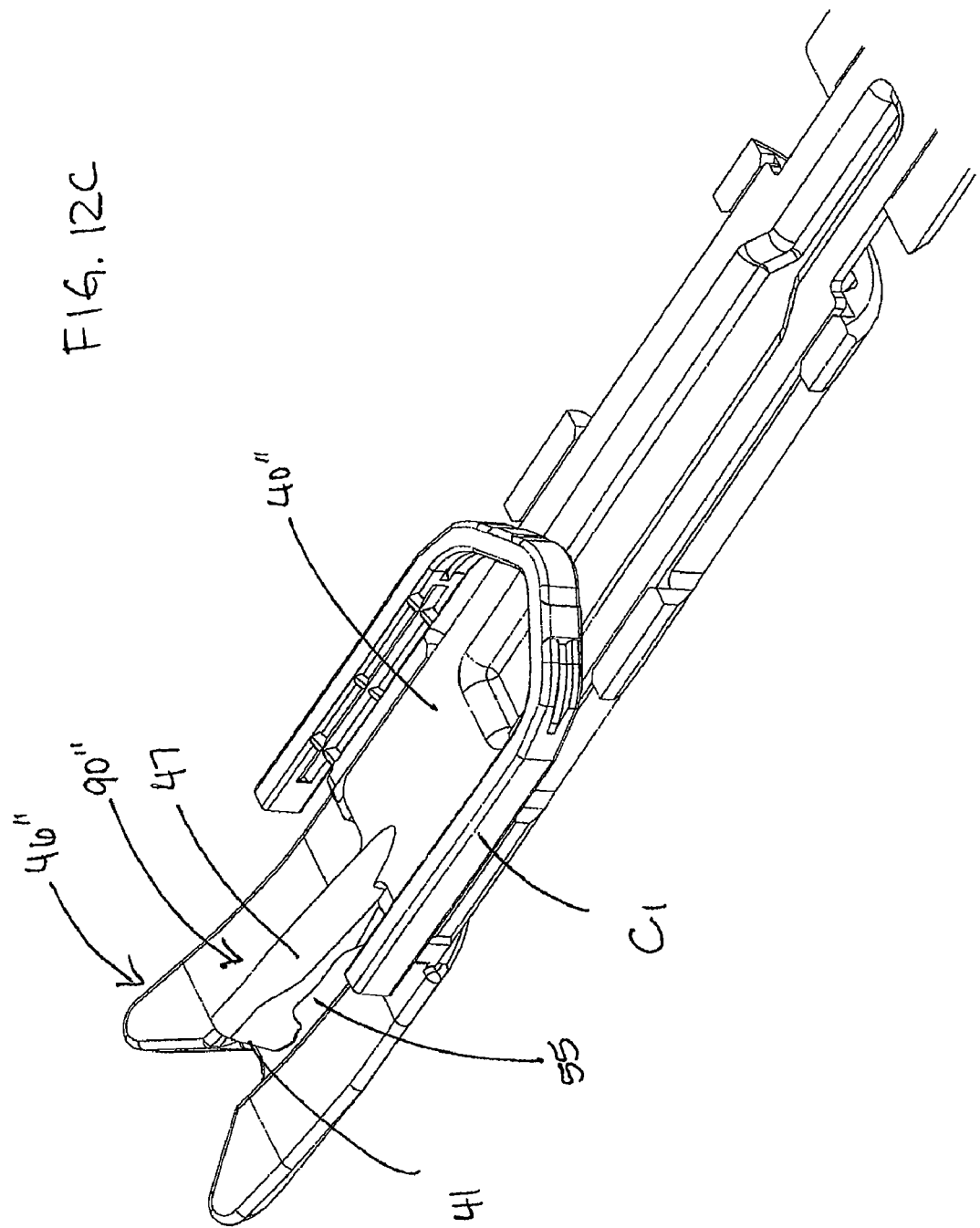

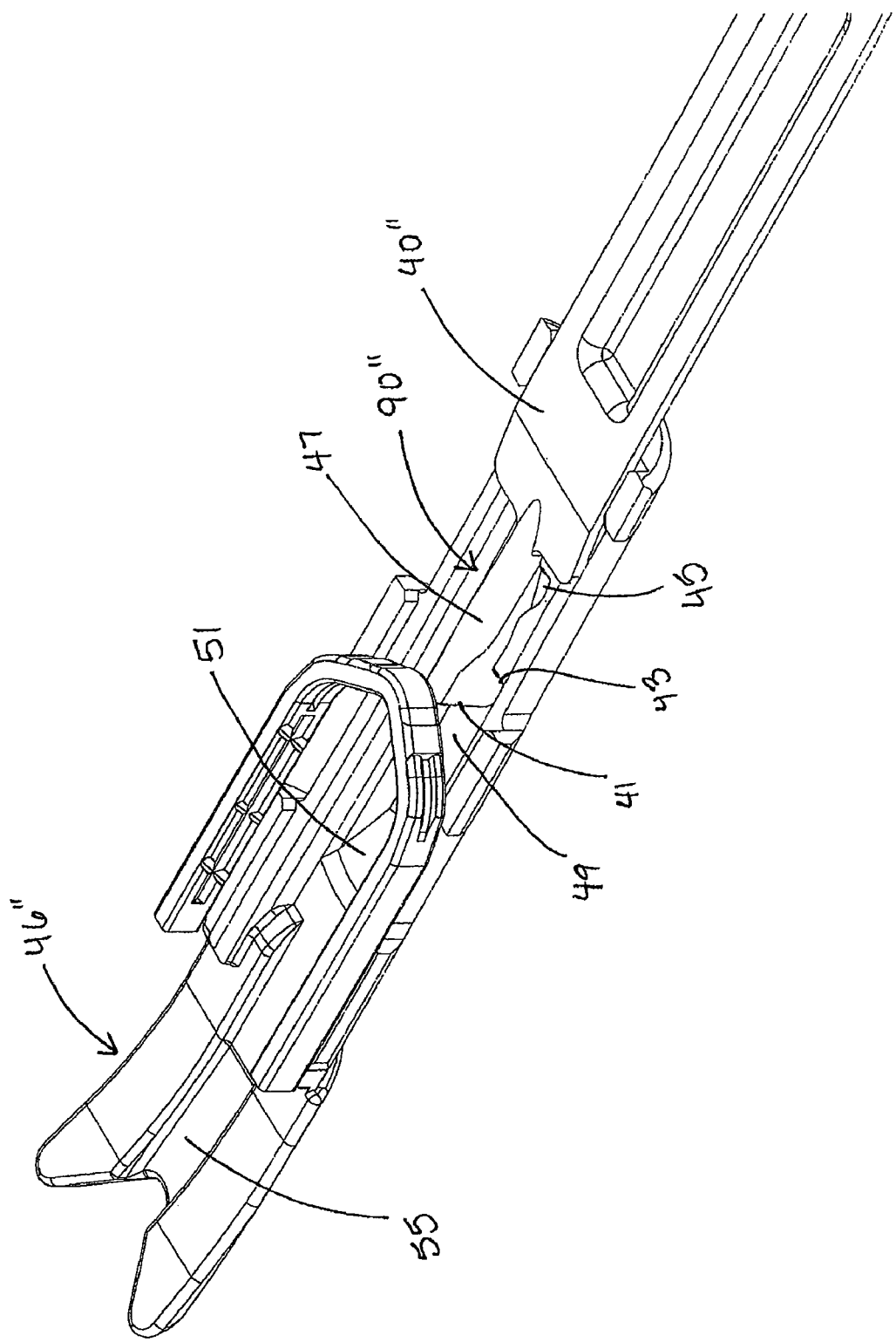

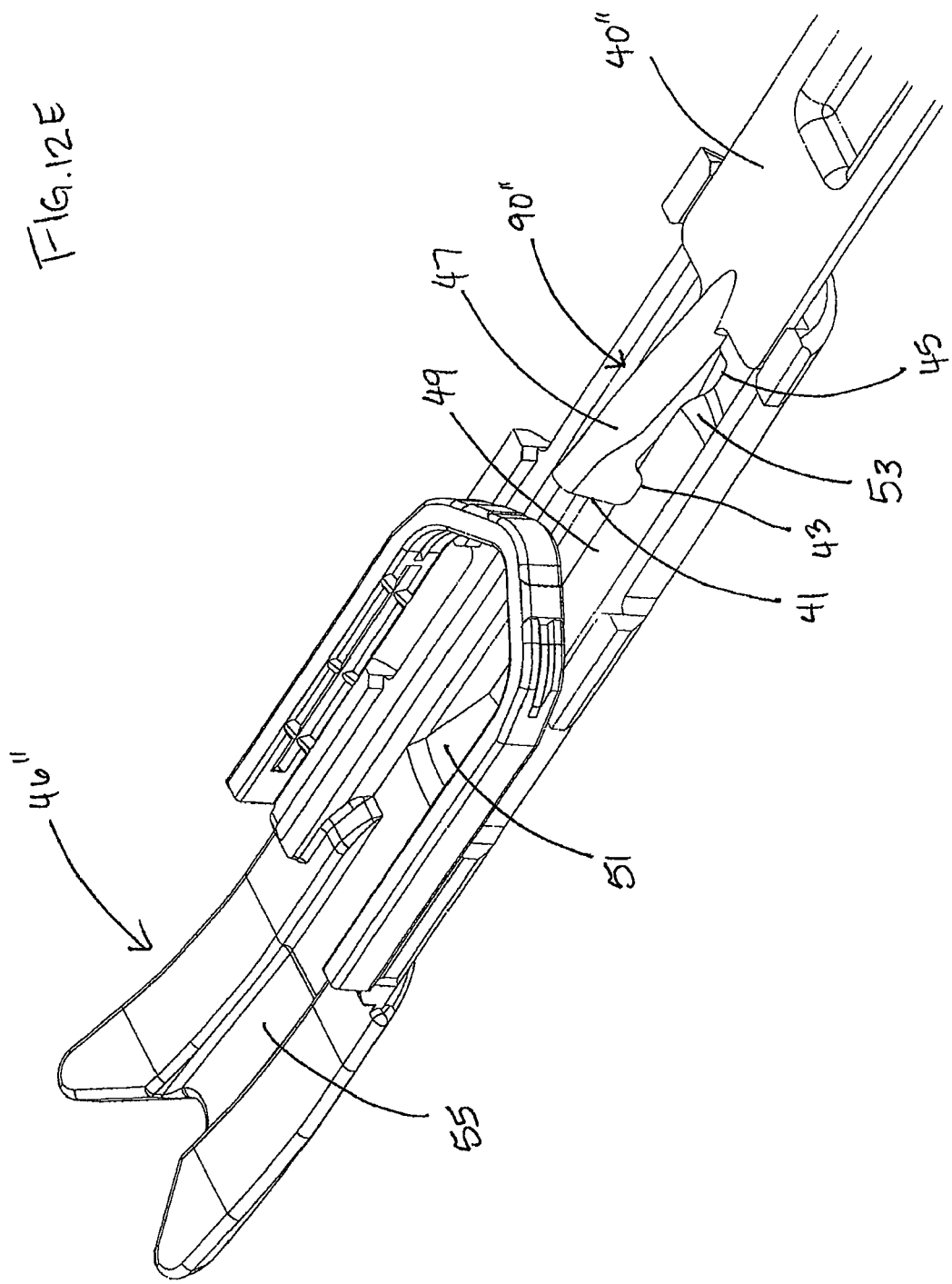

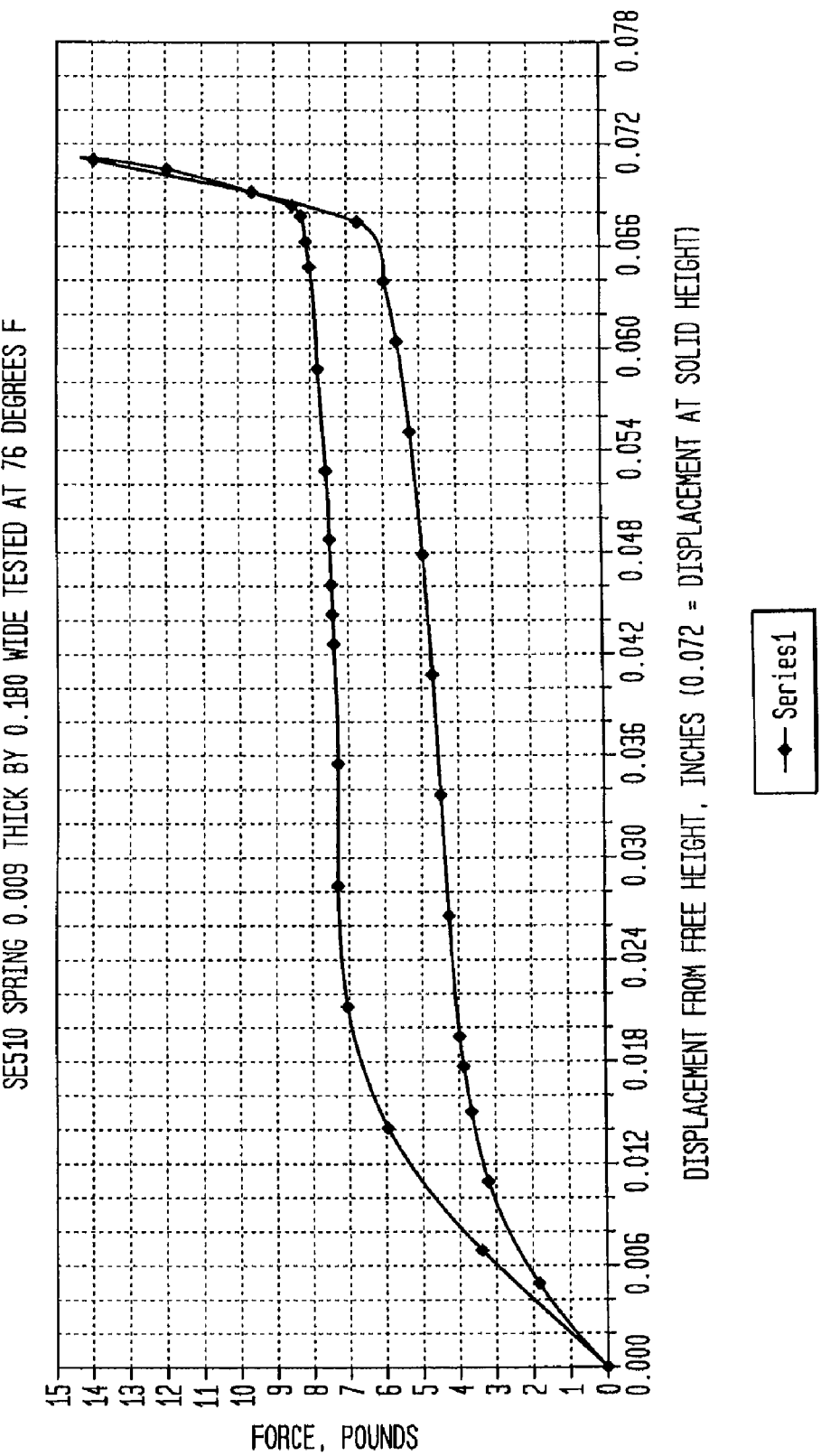

CLIP ADVANCER WITH LOCKOUT MECHANISM

CROSS-REFERENCE TO RELATED APPLICATIONS

The present application is a continuation-in-part of U.S. application Ser. No. 12/576,736 filed Oct. 9, 2009 and entitled "Improved Clip Advancer" which is hereby incorporated by reference in its entirety.

FIELD OF THE INVENTION

The present invention relates broadly to surgical devices, and in particular to methods and devices for applying surgical clips to ducts, vessels, shunts, etc.

BACKGROUND OF THE INVENTION

Surgical clip appliers are commonly used for ligating blood vessels, ducts, shunts, or a portion of body tissue during surgery. Most clip appliers typically have a handle with an elongate shaft having a pair of movable opposed jaws formed on an end thereof for holding and forming a ligation clip therebetween. The jaws are positioned around the vessel or duct, and the clip is crushed or formed on the vessel by the closing of the jaws.

Clip appliers that are configured to deliver multiple clips typically include an advancer mechanism that sequentially advances the clips into the jaws of the clip applier. One problem associated with advancer mechanisms is that there is generally no indication of when the clip applier is out of clips. In the middle of a procedure, a surgeon or other user may continue squeezing the trigger of a clip applier to apply clips even after the last clip has been applied. With no indication otherwise from the clip applier, the surgeon may believe he is closing an incision or other opening in tissue when he is not. Such a mistake could be dangerous to the patient, and at a minimum, could cost the surgeon valuable time in having to repeat at least a portion of the closing procedure.

Accordingly, there remains a need for improved methods and devices for applying surgical clips to vessels, ducts, shunts, etc.

SUMMARY OF THE INVENTION

The present invention provides method and devices for applying a surgical clip to a vessel, duct, shunt, etc. In one embodiment, a surgical clip applier is provided and can include a housing having a trigger movably coupled thereto and an elongate shaft extending therefrom with opposed jaws formed on a distal end thereof. An advancer assembly can be disposed within the elongate shaft and it can be configured to advance one of a plurality of clips disposed within the elongate shaft into the opposed jaws. In some embodiments, the advancer assembly can be movable between a proximal position and a distal position. The surgical clip applier can also include a feeder shoe disposed within the elongate shaft and configured to engage and prevent the advancer assembly from moving to the proximal position after the advancer assembly has moved to the distal position to advanced a proximal-most clip into the opposed jaws.

In some embodiments, movement of the trigger from an open position to a closed position can be effective to move the advancer assembly from the proximal position to the distal position. The surgical access device can also include a clip track disposed within the elongate shaft and having a plurality of clips seated therein, and the feeder shoe can be slidably disposed within the clip track to distally advance the plurality of clips through the clip track. In one embodiment, the advancer assembly can include a recess formed therein that is configured to be engaged by a tang on the feeder shoe to prevent the advancer assembly from moving to the proximal position after the advancer assembly has moved a proximal-most clip into the opposed jaws. The tang on the feeder shoe can be configured to move distally with the feeder shoe as the feeder shoe advances the plurality of clips through the clip track.

The advancer assembly can have many configurations and can include a feed bar coupled to an advancer. The advancer can have a distal end configured to contact and advance one of a plurality of clips into the opposed jaws. In some embodiments, the recess can be formed through a distal portion of the feed bar and a proximal portion of the advancer. A proximal portion of the tang can be connected to the feeder shoe and a distal portion of the tang can be disconnected from the feeder shoe and can extend a distance below an inferior surface of the feeder shoe.

In other aspects, a surgical clip applier is provided and can include a handle housing having a trigger movably coupled thereto and an elongate shaft extending distally therefrom. The elongate shaft can have opposed jaws on a distal end thereof. A clip advancing assembly can be operatively associated with the trigger and it can be configured to advance one of a plurality of clips disposed within the elongate shaft into the opposed jaws. A lockout mechanism can be configured to lock the clip advancing assembly in place after the clip advancing assembly has distally advanced a proximal-most clip into the opposed jaws. The clip advancing assembly can also be configured to lock the trigger in an actuated position when the clip advancing assembly is locked in place by the lockout mechanism.

In some embodiments, the surgical clip applier can further include a pawl and ratchet mechanism disposed within the handle housing and operatively associated with the trigger. The pawl and ratchet mechanism can have an engaged configuration in which the pawl and ratchet mechanism controls movement of the trigger and a disengaged configuration in which the trigger is movable independently of the pawl and ratchet mechanism. The lockout mechanism can be configured to lock the pawl and ratchet mechanism in an engaged configuration after the clip advancing assembly has advanced a proximal-most clip into the opposed jaws to thereby lock the trigger in an actuated position.

In one embodiment, the trigger can be movable in a first direction from a fully open position to a fully closed position, and a second direction from the fully closed position to the fully open position. The trigger can be limited to movement in only one of the first and second directions when the pawl and ratchet mechanism are in the engaged configuration. The trigger can be freely movable in both the first and second directions when the pawl and ratchet mechanism are in the disengaged configuration. In some embodiments, the ratchet mechanism can include a series of teeth for engaging the pawl.

The clip advancing assembly can have many configurations. For example, the clip advancing assembly can include a feeder shoe and an advancer assembly. In some embodiments, the lockout mechanism can include a tang formed on the feeder shoe that is configured for locking engagement with a recess formed in the advancer assembly after the advancer assembly advances a proximal-most clip into the opposed jaws. An inferior surface of the feeder shoe can be in slidable engagement with a superior surface of the advancer assembly. In other embodiments, the opposed jaws can be configured to open and release a proximal-most clip before the lockout mechanism locks the clip advancing assembly.

In another aspect, methods for advancing surgical clips are provided and can include moving a trigger from an open-most position to a closed-most position to correspondingly advance a proximal-most clip of a plurality of clips into opposed jaws of a clip applier. The method can further include releasing the trigger such that the trigger is locked in an actuated position between the open-most and closed-most positions to prevent the trigger from being moved to the open-most position. A tang formed on a feeder shoe can be engaged by a recess formed in an advancer assembly to lock the trigger. In some embodiments, moving the trigger from the open-most position to the closed-most position can move the advancer assembly distally over the feeder shoe to advance the proximal-most clip into the opposed jaws of the clip applier. Furthermore, releasing the trigger can move the advancer assembly proximally over the feeder shoe until the recess in the advancer assembly engages the tang on the feeder shoe. The method can also include releasing the proximal-most clip from the opposed jaws of the clip applier before the trigger is locked in an actuated position between the open-most and closed-most positions to prevent the trigger from being moved to the open-most position.

BRIEF DESCRIPTION OF THE DRAWINGS

The invention will be more fully understood from the following detailed description taken in conjunction with the accompanying drawings, in which:

FIG. 2A is a top view of a jaw retainer assembly of the surgical clip applier shown in FIG. 1A;

FIG. 2B is a bottom view of the jaw retainer assembly shown in FIG. 2A;

FIG. 2C is a side view of the jaw retainer assembly shown in FIG. 2B;

FIG. 2D is a cross-sectional view of the jaw retainer assembly shown in FIG. 2C taken across line D-D;

FIG. 3A is a top view of a feeder shoe for use with the jaw retainer assembly shown in FIGS. 2A-2D;

FIG. 3B is a bottom view of the feeder shoe shown in FIG. 3A;

FIG. 4A is a side perspective view of a feed bar that is configured to advance the feeder shoe of FIGS. 3A and 3B through the jaw retainer assembly shown in FIGS. 2A-2D;

FIG. 4B is a side view of the proximal end of the feed bar shown in FIG. 4A and the proximal end of the jaw retainer shaft shown in FIGS. 2A and 2B, showing the feed bar in a proximal-most position;

FIG. 4C is a side view of the feed bar and jaw retainer shaft shown in FIG. 4B, showing the feed bar in a distal-most position;

FIG. 4D is a side view of another embodiment of a proximal end of a feed bar shown in connection with the proximal end of the jaw retainer shaft shown in FIGS. 2A and 2B, showing the feed bar in the proximal-most position;

FIG. 4E is a side view of the feed bar and jaw retainer shaft shown in FIG. 4D, showing the feed bar in a distal-most position;

FIG. 4F is a side view of yet another embodiment of a proximal end of a feed bar shown in connection with the proximal end of the jaw retainer shaft shown in FIGS. 2A and 2B, showing the feed bar in the proximal-most position;

FIG. 4G is a side view of the feed bar and jaw retainer shaft shown in FIG. 4F, showing the feed bar in an intermediate position;

FIG. 4H is a side view of the feed bar and jaw retainer shaft shown in FIG. 4F, showing the feed bar in a distal-most position;

FIG. 5C is a perspective view of still another embodiment of an advancer that is configured to couple to a distal end of the feed bar shown in FIG. 4I;

FIG. 5D is another perspective view of the advancer of FIG. 5C;

FIG. 6A is a cross-sectional view of a clip advancing assembly, which includes the jaw retainer assembly shown in FIGS. 2A-2D, the feeder shoe shown in FIGS. 3A-3B, and the feed bar shown in FIG. 4A, showing the feed bar in an initial, proximal position relative to the clip track of the jaw retainer assembly;

FIG. 6B is a cross-sectional view of the clip advancing assembly shown in FIG. 6A, showing the feed bar moved in a distal direction;

FIG. 9 is a top perspective view of a push rod that is adapted to couple to the cam shown in FIG. 8 for moving the cam relative to the jaws shown in FIG. 7;

FIG. 11E is a perspective view of another embodiment of a tissue stop that is adapted to couple to a distal end of the clip track of the jaw retainer assembly shown in FIGS. 2A-2D;

FIG. 11F is another perspective view of the tissue stop of FIG. 11E;

FIG. 12B is perspective view of the advancer of FIG. 5C advancing a clip over the tissue stop of FIG. 11E;

FIG. 12C is a perspective view of the advancer of FIG. 5C in a distal position on the tissue stop of FIG. 11E;

FIG. 12D is a perspective view of the advancer of FIG. 5C deflecting under a distal-most clip within a channel formed in the tissue stop of FIG. 11E;

FIG. 12E is a perspective view of the advancer of FIG. 5C in a proximal position on the tissue stop of FIG. 11E;

FIG. 20D is a chart showing the amount of force required to displace the biasing element shown in FIG. 20B;

DETAILED DESCRIPTION OF THE INVENTION

Figure 1A:
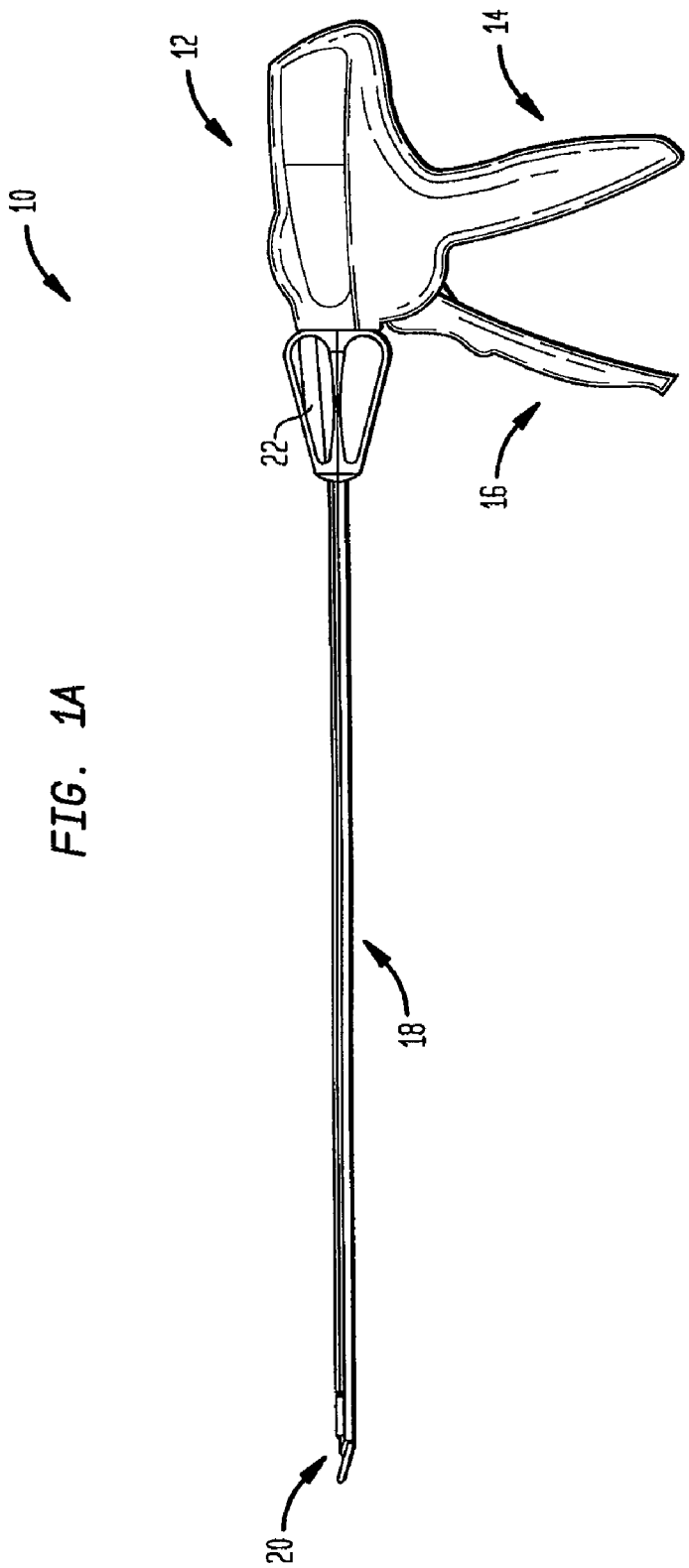
FIG. 1A is a side view of one exemplary embodiment of a surgical clip applier.

The present invention generally provides a surgical clip applier and methods for using a surgical clip applier to apply surgical clips to a vessel, duct, shunt, etc., during a surgical procedure. An exemplary surgical clip applier can include a variety of features to facilitate application of a surgical clip, as described herein and illustrated in the drawings. However, a person skilled in the art will appreciate that the surgical clip applier can include only some of these features and/or it can include a variety of other features known in the art. The surgical clip applier described herein is merely intended to represent certain exemplary embodiments.

Figure 1B:
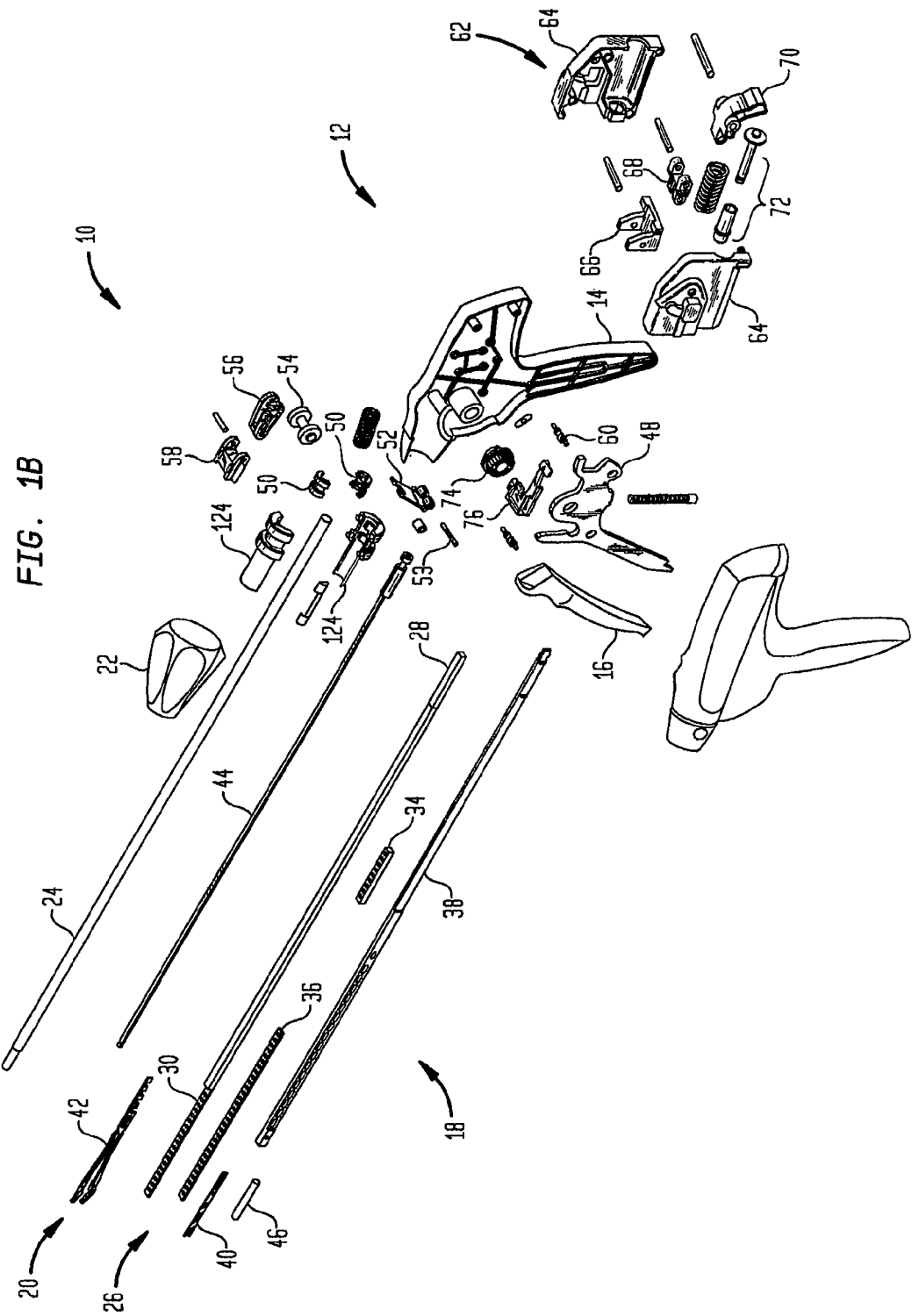
FIG. 1B is an exploded view of the surgical clip applier shown in FIG. 1A.

FIG. 1A illustrates one exemplary surgical clip applier 10. As shown, the clip applier 10 generally includes a housing 12 having a stationary handle 14 and a movable handle or trigger 16 that is pivotally coupled to the housing 12. An elongate shaft 18 extends from the housing 12 and it includes a pair of opposed jaws 20 formed on a distal end thereof for crimping a surgical clip. The elongate shaft 18 can be rotatably coupled to the housing 12, and it can include a rotation knob 22 for rotating the shaft 18 relative to the housing 12. FIG. 1B illustrates an exploded view of the surgical clip applier 10 shown in FIG. 1A, and the various components will be described in more detail below.

FIGS. 2A-12 illustrate exemplary embodiments of the various components of the shaft 18 of the surgical clip applier 10. In general, referring to FIG. 1B, the shaft 18 includes an outer tube 24 that houses the shaft components, which can include a jaw retaining assembly 26 having a jaw retainer shaft 28 with a clip track 30 and a push rod channel 32 formed thereon. The jaws 20 can be configured to mate to a distal end of the clip track 30. The shaft assembly 18 can also include a clip advancing assembly, which in one exemplary embodiment can include a feeder shoe 34 that is adapted to be slidably disposed within the clip track 30 to advance a series of clips 36 positioned therein, and a feed bar 38 that is adapted to drive the feeder shoe 34 through the clip track 30. The feed bar 38 can include an advancer assembly 40 that is adapted to mate to a distal end thereof for advancing a distal-most clip into the jaws 20. The shaft assembly 18 can also include a clip forming or camming assembly, which in one exemplary embodiment can include a cam 42 that is adapted to slidably mate to the jaws 20, and a push rod 44 that can couple to the cam 42 to move the cam 42 relative to the jaws 20. The shaft assembly can also include a tissue stop 46 that can mate to a distal end of the clip track 30 for facilitating positioning of the jaws 20 relative to a surgical site.

The various components of one exemplary clip advancing assembly are shown in more detail in FIGS. 2A-5. Referring first to FIGS. 2A-2D, the jaw retaining assembly 26 is shown and it includes an elongate, substantially planar jaw retainer shaft 28 having a proximal end 28a that mates to the outer tube 24, and a distal end 28b that is adapted to mate to the jaws 20. While a variety of techniques can be used to mate the proximal end 28a of the jaw retainer shaft 28 to the outer tube 24, in the illustrated embodiment the proximal end 28a includes teeth 31 formed on opposed sides thereof that are adapted to be received within corresponding holes or openings (not shown) formed in the outer tube 24, and a cut-out 29 formed therein that allows the opposed sides of the proximal end 28a to deflect or to form a spring. In particular, the cut-out 29 allows the opposed sides of the proximal end 28a of the jaw retainer shaft 28 to be compressed toward one another when the jaw retainer shaft 28 is inserted in the outer tube 24. Once the teeth 31 are aligned with the corresponding openings in the outer tube 24, the proximal end 28a of the jaw retainer shaft 28 will return to its original, uncompressed configuration thereby causing the teeth 31 to extend into the corresponding openings to engage the outer 24. As will be discussed in more detail below with respect to FIG. 4A, the device can also include a feature to prevent compression of the opposed sides of the proximal end 28a of the jaw retainer shaft 28 during use of the device to prevent accidental disengagement of the teeth 31 from the outer tube 24.

A variety of techniques can also be used to mate the distal end 28b of the jaw retainer shaft 28 to the jaws 20, however in the illustrated embodiment the distal end 28b of the jaw retainer shaft 28 includes several cut-outs or teeth 78 formed therein for mating with corresponding protrusions or teeth 94 formed on the jaws 20, which will be discussed in more detail below with respect to FIG. 7. The teeth 78 allow a proximal portion of the jaws 20 to be substantially co-planar with the jaw retainer shaft 28.

The jaw retaining assembly 26 can also include a push rod channel 32 formed thereon for slidably receiving the push rod 44, which is used to advanced the cam 42 over the jaws 20, as will be discussed in more detail below. The push rod channel 32 can be formed using a variety of techniques, and it can have any shape and size depending on the shape and size of the push rod 44. As shown in FIG. 2D, the push rod channel 32 is fixedly attached, e.g., by welding, to a superior surface of the retainer shaft 28, and it has a substantially rectangular shape and defines a pathway 32a extending therethrough. The push rod channel 32 can also extend along all or only a portion of the retainer shaft 28. A person skilled in the art will appreciate that the jaw retaining assembly 26 does not need to include a push rod channel 32 for facilitating movement of the push rod 44 within the elongate shaft 18 of the surgical clip applier 10.

As is further shown in FIGS. 2A-2D, the jaw retaining assembly 26 can also include a clip track 30 mated thereto or formed thereon. The clip track 30 is shown mated to an inferior surface of the jaw retainer shaft 28, and it extends distally beyond the distal end 28b of the jaw retainer shaft 28 to allow a distal end 30b of the clip track 30 to be substantially aligned with the jaws 20. In use, the clip track 30 is configured to seat at least one, and preferably a series, of clips therein. Accordingly, the clip track 30 can include opposed side rails 80a, 80b that are adapted to seat opposed legs of one or more clips therein, such that the legs of the clips are axially aligned with one another. In an exemplary embodiment, the clip track 30 can be configured to seat about twenty clips that are pre-disposed within the clip track 30 during manufacturing. A person skilled in the art will appreciate that the shape, size, and configuration of the clip track 30 can vary depending on the shape, size, and configuration of clips, or other closure devices such as staples, adapted to be received therein. Moreover, a variety of other techniques can be used, instead of a clip track 30, to retain a clip supply with the elongate shaft 18.

The clip track 30 can also include several openings 30c formed therein for receiving a tang 82a formed on a feeder shoe 34 adapted to be disposed within the clip track 30, as will be discussed in more detail below. In an exemplary embodiment, the clip track 30 includes a quantity of openings 30c that corresponds to at least the number of clips adapted to be pre-disposed within the device 10 and applied during use. The openings 30c are preferably equidistant from one another to ensure that the tang 82a on the feeder shoe 34 engages an opening 30c each time the feeder shoe 34 is advanced. While not shown, the clip track 30 can include detents, rather than openings 30c, or it can include other features that allow the clip track 30 to engage the feeder shoe 34 and prevent proximal movement, yet allow distal movement, of the feeder shoe 34. The clip track 30 can also include a stop tang 118 formed thereon, as shown in FIG. 2B, that is effective to be engaged by a corresponding stop tang formed on the feeder shoe 34 to prevent movement of the feeder shoe 34 beyond a distal-most position, as will be discussed below. The stop tang 118 can have a variety of configurations, but in one exemplary embodiment it is in the form of two adjacent tabs that extend toward one another to enclose a portion of the clip track, thus allowing clips to pass therethrough.

An exemplary feeder shoe 34 is shown in more detail in FIGS. 3A and 3B, and it can be adapted to directly drive clips through the clip track 30. While the feeder shoe 34 can have a variety of configurations, and a variety of other techniques can be used to drive clips through the clip track 30, in an exemplary embodiment the feeder shoe 34 has a generally elongate shape with proximal and distal ends 34a, 34b. The distal end 34b can be adapted to cradle the proximal-most clip in the clip track 30 to push the clip(s) through the clip track 30. In the illustrated exemplary embodiment, the distal end 34b is substantially v-shaped for seating a v-shaped bight portion of a clip. The distal end 34b also includes a rectangular-shaped notch 34c formed therein for allowing the advancer 40 to engage a distal-most clip and advance it into the jaws 20, as will be discussed in more detail below. The distal end 34b can, of course, vary depending on the configuration of the clip, or other closure mechanism, being used with the device 10.

In another exemplary embodiment, the feeder shoe 34 can also include features to facilitate distal movement of the feeder shoe 34 within the clip track 30, and to substantially prevent proximal movement of the feeder shoe 34 within the clip track 30. Such a configuration will ensure advancement and proper positioning of the clips within the clip track 30, thus allowing a distal-most clip to be advanced between the jaws 20 with each actuation of the trigger 16, as will be discussed in more detail below. In the illustrated exemplary embodiment, the feeder shoe 34 includes a tang 82a formed on a superior surface 34s thereof and angled proximally for engaging one of the openings 30c formed in the clip track 30. In use, the angle of the tang 82a allows the feeder shoe 34 to slide distally within the clip track 30. Each time the feeder shoe 34 is advanced, the tang 82a will move in a distal direction from one opening 30c to the next opening 30c in the clip track 30. The engagement of the tang 82a with the opening 30c in the clip track 30 will prevent the feeder shoe 34 from moving proximally to return to the previous position, as will be described in more detail below.

In order to facilitate distal movement of the feeder shoe 34 within the clip track 30, the feeder shoe 34 can also include a tang 82b formed on the inferior surface 34i thereof, as shown in FIG. 3B, for allowing the feeder shoe 34 to be engaged by the feed bar 38 (FIG. 4A) as the feed bar 38 is moved distally. The inferior tang 82b is similar to the superior tang 82a in that it can be angled proximally. In use, each time the feed bar 38 is moved distally, a detent 84 formed in the feed bar 38 can engage the inferior tang 82b and move the feeder shoe 34 distally a predetermined distance within the clip track 30. The feed bar 38 can then be moved proximally to return to its initial position, and the angle of the inferior tang 82b will allow the tang 82b to slide into the next detent 84 formed in the feed bar 38. As previously noted, a variety of other features rather than tangs 82a, 82b and openings 30c or detents 84 can be used to control movement of the feeder shoe 34 within the clip track 30.

As previously mentioned, the feeder shoe 34 can also include a stop formed thereon that is adapted to stop movement of the feeder shoe 34 when the feeder shoe 34 is in the distal-most position and there are no clips remaining in the device 10. While the stop can have a variety of configurations, FIGS. 3A and 3B illustrate a third tang 82c formed on the feeder shoe 34 and extending in an inferior direction for engaging the stop tang 118 (FIG. 2B) formed on the clip track 30. The third tang 82c is positioned such that it will engage the stop tang 118 on the clip track 30 when the feeder shoe 34 is in a distal-most position, thereby preventing distal movement of the feeder shoe 34 and the feed bar 38 when the clip supply is depleted.

In another embodiment, the surgical clip applier can have a stop mechanism that can indicate to a user when a clip supply of the surgical clip applier is depleted. The stop mechanism can, for example, prevent the user from fully opening a trigger of the surgical clip applier to thereby indicate that the last clip has been applied. This prevents the user from continuing to attempt to apply clips in the belief that clips remain in the clip supply. The stop mechanism can have many configurations, but in an exemplary embodiment the stop mechanism is configured to lock the clip advancing assembly of the surgical clip applier in a fixed position after a proximal-most clip has been advanced into opposed jaws of the clip applier. This is in turn effective to lock the trigger 16, which is operatively associated with the clip advancing assembly, in a fixed position. Thus, as a user attempts to release the trigger 16 of the clip applier and return it to its open position, the locked advancer and feed bar prevent the trigger from returning to its open position, thereby indicating to the user that the clip supply is depleted.

Figure 3C:
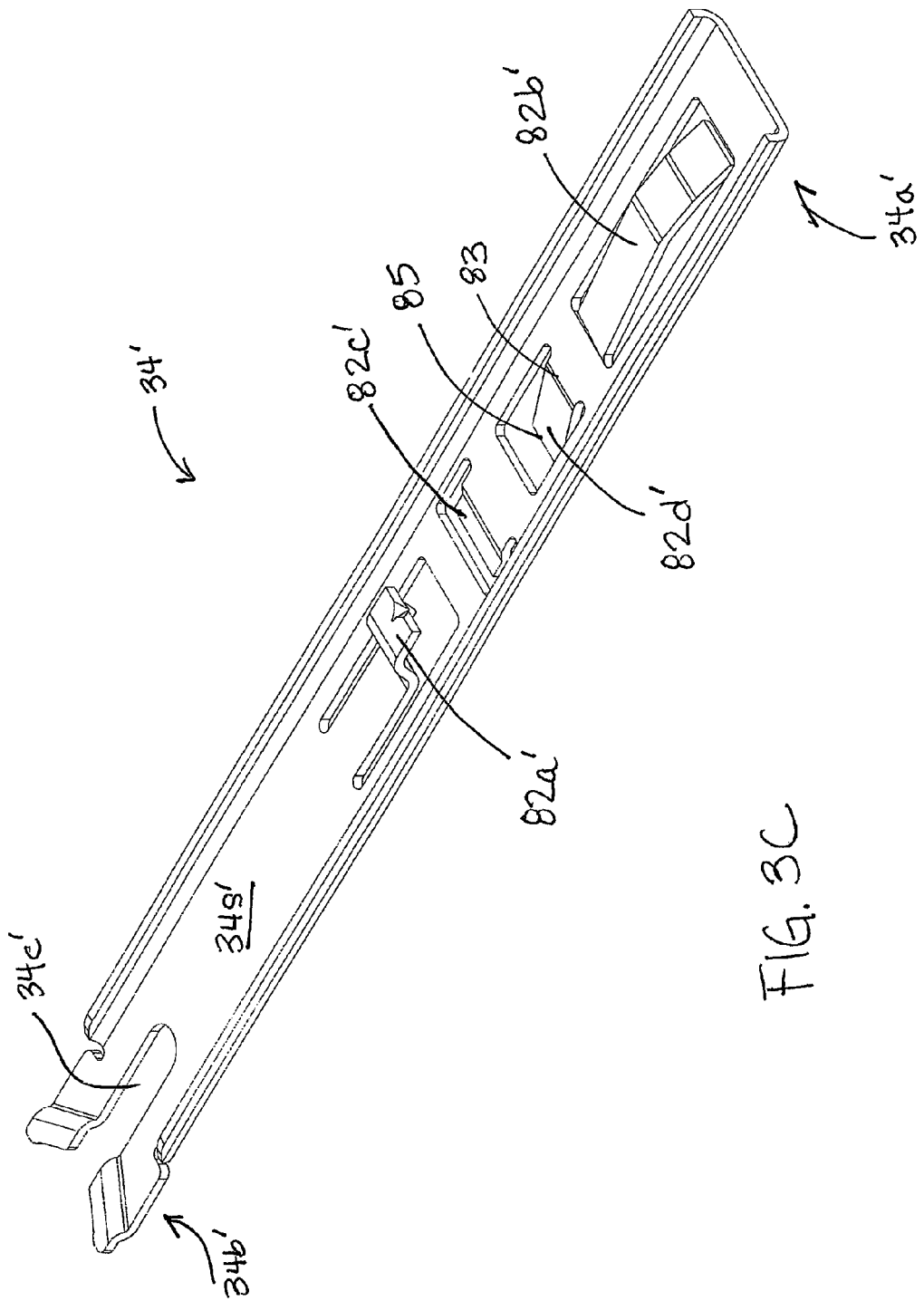
FIG. 3C is a perspective view of another embodiment of a feeder shoe for use with the jaw retainer assembly shown in FIGS. 2A-2D.
Figure 3D:
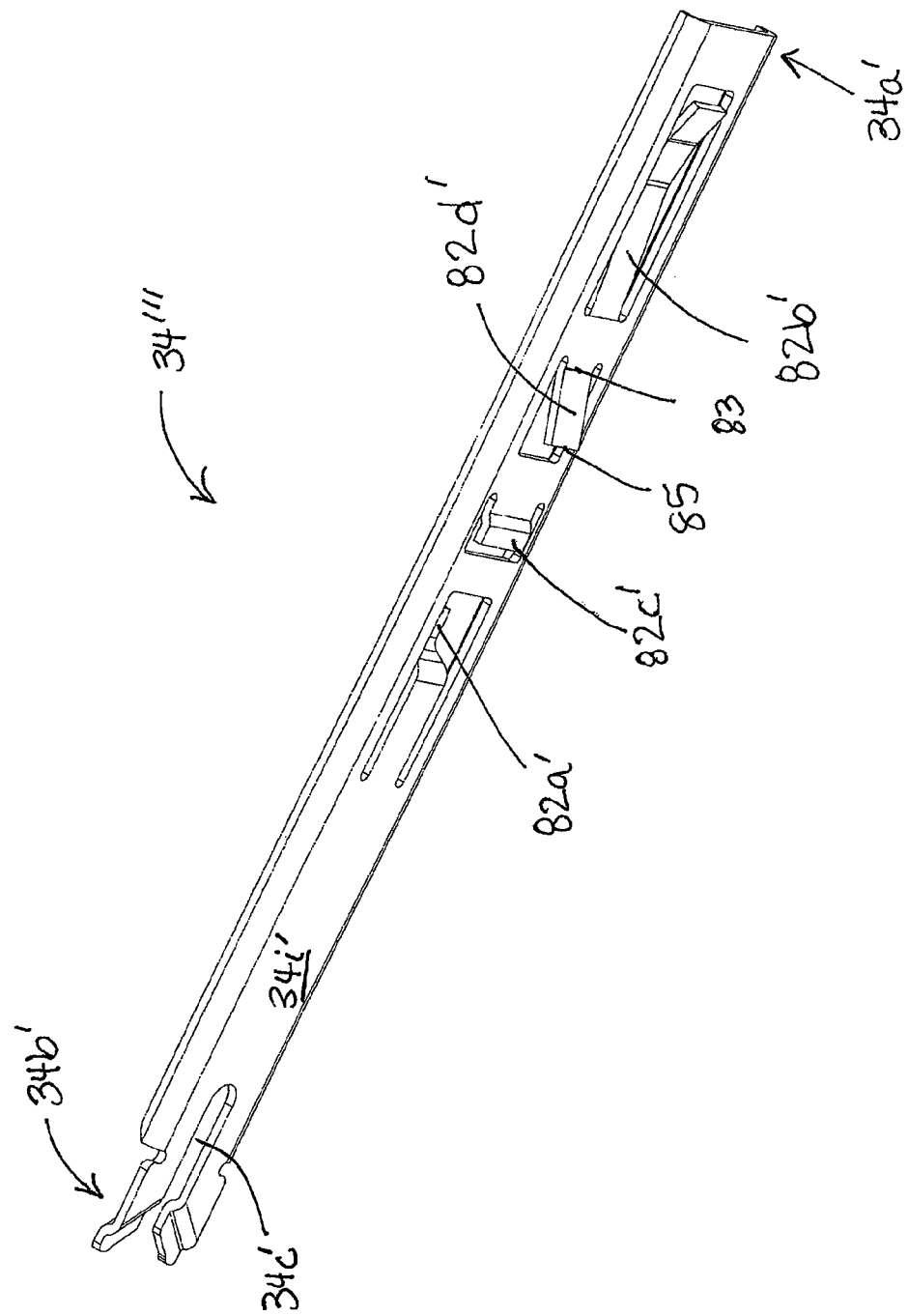
FIG. 3D is a perspective view of the feeder shoe of FIG. 3C.

While the stop mechanism can have any configuration and can be formed at various locations on the device, in one embodiment the stop mechanism is in the form of an engagement feature formed on the feeder shoe and the feed bar. FIGS. 3C and 3D illustrate one exemplary embodiment of a feeder shoe 34''' having an engagement feature formed thereon for mating with a corresponding engagement feature on the feed bar, as will be discussed in more detail below. Similar to the previous embodiment, the illustrated feeder shoe 34''' has a generally elongate shape with proximal and distal ends 34a', 34b'. The distal end 34b' is adapted to cradle the proximal-most clip in the clip track 30 to push the clip(s) through the clip track 30. In this embodiment, the distal end 34b' is substantially v-shaped for seating a v-shaped bight portion of a clip. The distal end 34b' can also include a rectangular-shaped notch 34c' formed therein for allowing the advancer 40, 40'' to engage a distal-most clip and advance it into the jaws 20, as will be discussed in more detail below. The distal end 34b' can, of course, vary depending on the configuration of the clip, or other closure mechanism, being used with the device 10.

The illustrated feeder shoe 34''' can also include a number of features, such as tangs similar to those discussed above with respect to the feeder shoe 34 shown in FIGS. 3A and 3B, to facilitate distal movement of the feeder shoe 34''' within the clip track 30, and to substantially prevent proximal movement of the feeder shoe 34''' within the clip track 30. Such a configuration will ensure advancement and proper positioning of the clips within the clip track 30, thus allowing a distal-most clip to be advanced between the jaws 20 with each actuation of the trigger 16, as will be discussed in more detail below. For example, one or more tangs can be provided on the feeder shoe 34''' to engage the clip track 30. The tangs can generally have a rectangular shape and can be formed by cutting three sides of a rectangle from the feeder shoe 34''' and deflecting the rectangle away from the feeder shoe 34' so as to form a snag tab. Tangs that are angled proximally can be spaced apart from a superior or inferior surface of the feeder shoe 34''' at their proximal end to form a catch that will engage the clip track 30 when the feeder shoe 34''' is moved proximally. Likewise, tangs that are angled distally can be spaced apart from a superior or inferior surface of the feeder shoe 34''' at their distal end to form a catch that will engage the clip track 30 when the feeder shoe 34''' is moved distally. In the illustrated exemplary embodiment, the feeder shoe 34''' includes a tang 82a' that protrudes above a superior surface 34s' of the feeder shoe 34''' and that is angled proximally for engaging one of the openings 30c formed in the clip track 30. In use, the angle of the tang 82a' allows the feeder shoe 34''' to slide distally within the clip track 30. Each time the feeder shoe 34''' is advanced, the tang 82a' will move in a distal direction from one opening 30c to the next opening 30c in the clip track 30 (shown in FIG. 6A). The engagement of the tang 82a' with the opening 30c in the clip track 30 will prevent the feeder shoe 34''' from moving proximally to return to the previous position, as will be described in more detail below.

In order to facilitate distal movement of the feeder shoe 34''' within the clip track 30, the feeder shoe 34''' can also include a tang 82b' that protrudes below the inferior surface 34i' of the feeder shoe 34''', as shown in FIG. 3D, for allowing the feeder shoe 34''' to be engaged by a feed bar 38' as the feed bar 38' is moved distally. The inferior tang 82b' is similar to the superior tang 82a' in that it can be angled proximally. In use, each time the feed bar 38' is moved distally, a detent 84 formed in the feed bar 38' can engage the inferior tang 82b' and move the feeder shoe 34''' distally a predetermined distance within the clip track 30. The feed bar 38' can then be moved proximally to return to its initial position, and the angle of the inferior tang 82b' will allow the tang 82b' to slide into the next detent 84 formed in the feed bar 38'. As previously noted, a variety of other features rather than tangs 82a', 82b' and openings 30c or detents 84 can be used to control movement of the feeder shoe 34''' within the clip track 30.

The feeder shoe 34''' can also include a stop formed thereon that is adapted to stop distal movement of the feeder shoe 34''' when the feeder shoe 34''' is in the distal-most position and there are no clips remaining in the device 10. While the stop can have a variety of configurations, FIGS. 3C and 3D illustrate a third tang 82c' formed on the feeder shoe 34''' that protrudes below the inferior surface and that is angled for engaging the stop tang 118 (FIG. 2B) formed on the clip track 30. The third tang 82c' is positioned such that it will engage the stop tang 118 on the clip track 30 when the feeder shoe 34''' is in a distal-most position, thereby preventing distal movement of the feeder shoe 34''' and the feed bar 38 when the clip supply is depleted.

The feeder shoe 34''' can further include a stop mechanism that is adapted to lock an advancer 40'' and the feed bar 38', described in more detail below, in a fixed position after the advancer 40'' advances the proximal-most clip into the jaws 20. Such a stop mechanism can provide tactile feedback to a user to ensure that the user is aware that the clip supply is depleted. While the stop mechanism can have many configurations, in the embodiment illustrated in FIGS. 3C and 3D, the feeder shoe 34''' includes a fourth tang 82d' that extends below the inferior surface and that is angled distally. A proximal portion 83 of the tang 82d' is connected with the feeder shoe 34''' while a distal portion 85 is not connected with the feeder shoe 34''' and is spaced a distance apart from the inferior surface. The tang 82d' is positioned to engage a recess 51 formed in the advancer 40' and the feed bar 38' to thereby prevent the advancer 40'' and the feed bar 38' from moving proximally back to their starting position, as will be described in more detail below.

FIG. 4A illustrates an exemplary feed bar 38 for driving the feeder shoe 34 through the clip track 30 of the jaw retaining assembly 26. As shown, the feed bar 38 has a generally elongate shape with proximal and distal ends 38a, 38b. The proximal end 38a of the feed bar 38a can be adapted to mate to a feed bar coupler 50 (FIG. 1B), which will be discussed in more detail below. The feed bar coupler 50 can mate to a feed link 52 that is effective, upon actuation of the trigger 16, to slidably move the feed bar 38 in a distal direction within the elongate shaft 18. The distal end 38b of the feed bar 38b can be adapted to mate to an advancer 40, 40', exemplary embodiments of which are shown in FIGS. 5A and 5B, that is effective to drive a distal-most clip disposed within the clip track 30 into the jaws 20, which will be discussed in more detail below.

As previously mentioned, the proximal end 38a of the feed bar 38 can include a feature to prevent compression of the opposed sides of the proximal end 28a of the jaw retainer shaft 28 (FIGS. 2A and 2B) during use of the device to prevent accidental disengagement of the teeth 31 from the outer tube 24. In one exemplary embodiment, shown FIGS. 4A-4C, the proximal end 38a of the feed bar 38 can include a protrusion 39 formed thereon that is adapted to extend into the opening 29 formed in the proximal end 28a of the jaw retainer shaft 28. When the feed bar 38 is in a proximal-most position (i.e., when the trigger 16 is in an open position), the protrusion 39 will be positioned at the proximal end of the opening 29, as shown in FIG. 4B, allowing the proximal end 28a of the jaw retainer shaft 28 to compress to allow the shaft 28 to slide into the outer tube 24. When the feed bar 38 is in a distal-most position (i.e., when the trigger 16 is in at least a partially closed position), the protrusion 39 will be positioned at an intermediate location adjacent to the teeth 31 as shown in FIG. 4C, to prevent compression of the proximal end 28a of the jaw retainer shaft 28. This is particularly advantageous during use of the device, as the protrusion 39 will prevent accidental disengagement of the jaw retainer shaft 28 from the outer tube 24 during use of the device. While FIGS. 4A-4C illustrate a protrusion 39 having a rectangular cross-sectional shape with rounded edges, the protrusion 39 can have a variety of other shapes and sizes. For example, as shown in FIGS. 4D and 4E, the protrusion 39' has a cross-sectional shape that is somewhat triangular with a tapering end that is adapted to extend between the teeth 31 to further ensure that the proximal end 28a of the jaw retainer shaft 28 can not be compressed during use of the device. More than one protrusion can also be used. For example, FIGS. 4F-4H illustrate another embodiment in which the proximal end 38a' of the feed bar 38 includes two protrusions 39a, 39b formed thereon and spaced a distance apart from one another. The two protrusions 39a, 39b will prevent compression of the proximal end 28a of the jaw retainer shaft 28 when the feed bar 38 is in a proximal-most position, as shown in FIG. 4F, and when the feed bar 38 is in a distal-most position, as shown in FIG. 4H. Compression of the proximal end 28a of the jaw retainer shaft 28 can only occur when the feed bar 38 is at an intermediate position such that the teeth 31 are positioned between the protrusions 39a, 39b, as shown in FIG. 4G.

As was also previously mentioned, the feed bar 38 can include one or more detents 84 formed therein for engaging the inferior tang 82b formed on the feeder shoe 34. The quantity of detents 84 can vary, but in an exemplary embodiment the feed bar 38 has a quantity of detents 84 that corresponds to or is greater than a quantity of clips adapted to be delivered by the device 10, and more preferably it has one more detent 84 than the quantity of clips adapted to be delivered by the device 10. By way of non-limiting example, the feed bar 38 can include eighteen detents 84 formed therein for delivering seventeen clips that are pre-disposed within the clip track 30. Such a configuration allows the feed bar 38 to advance the feeder shoe 34 seventeen times, thereby advancing seventeen clips into the jaws 20 for application. The detents 84 are also preferably equidistant from one another to ensure that the feeder shoe 34 is engaged and advanced by the feed bar 38 each time the feed bar 38 is advanced.

The feed bar 38 can also include a feature to control the amount of movement of the feed bar 38 relative to the clip track 30. Such a configuration will ensure that the feeder shoe 34 is advanced a predetermined distance each time the trigger 16 is actuated, thereby advancing only a single clip into the jaws 20. While a variety of techniques can be used to control the distal of movement of the feed bar 38, in an exemplary embodiment the feed bar 38 can include a protrusion 86 formed thereon that is adapted to be slidably received within a corresponding slot 88 (FIG. 2B) formed in the jaw retainer shaft 28. The length of the slot 88 is effective to limit movement of the protrusion 86 therein, thus limiting movement of the feed bar 38. Accordingly, in use the feed bar 38 can slide between a fixed proximal position and a fixed distal position with respect to the clip track 30, thereby allowing the feed bar 38 to advance the feeder shoe 34 by a predetermined distance with each advancement of the feed bar 38.

Figure 4I:
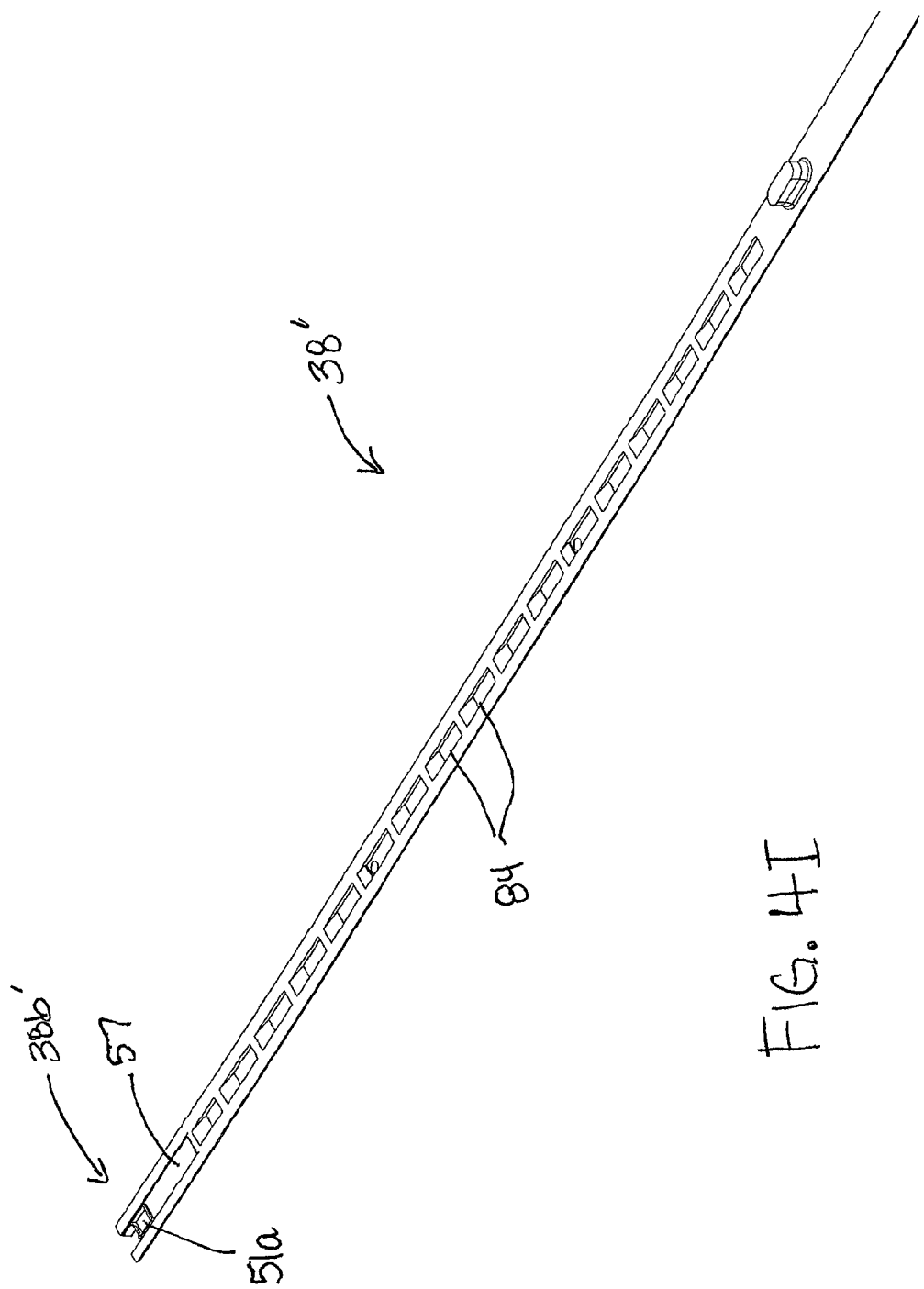
FIG. 4I is perspective view of another embodiment of a feed bar that is configured to advance the feeder shoe of FIGS. 3C and 3D through the jaw retainer assembly shown in FIGS. 2A-2D.
Figure 5A:
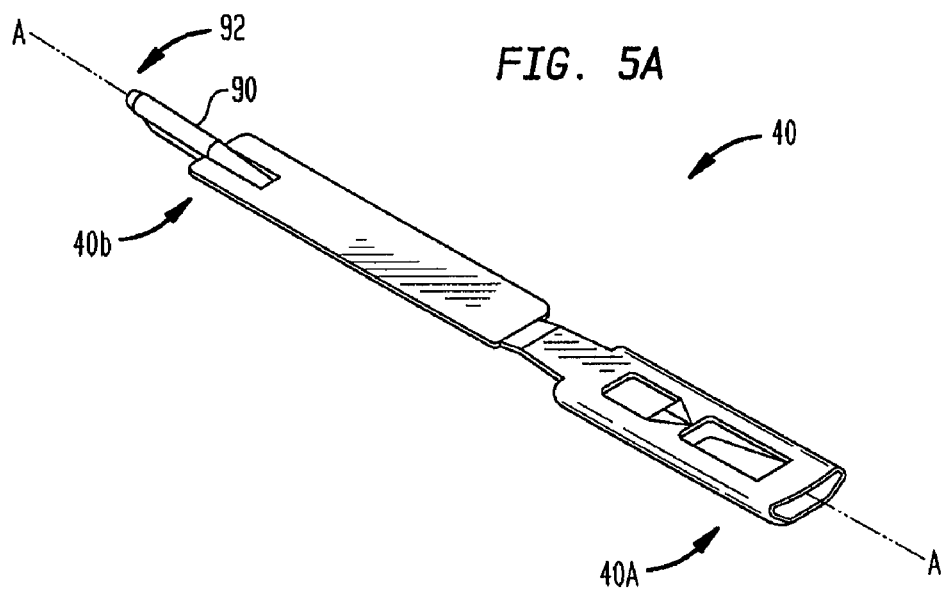
FIG. 5A is a side perspective view of an advancer that is configured to couple to a distal end of the feed bar shown in FIG. 4A.
Figure 5B:
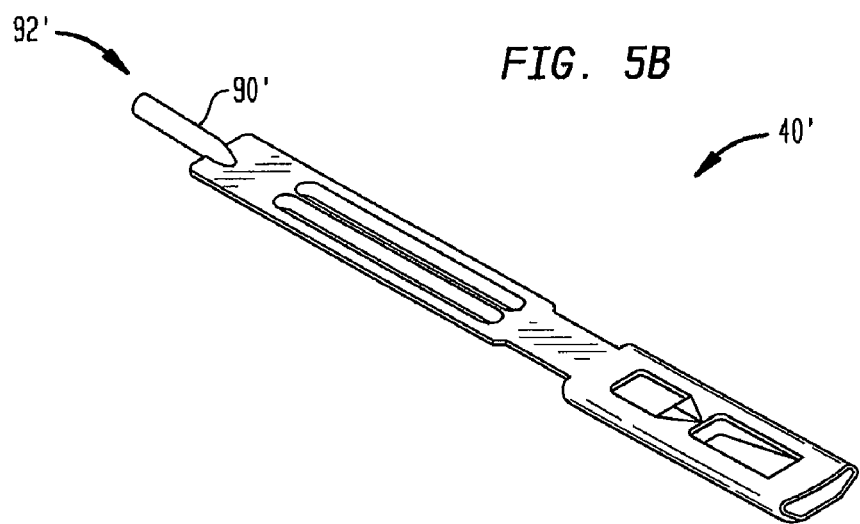
FIG. 5B is a side perspective view of another embodiment of an advancer that is configured to couple to a distal end of the feed bar shown in FIG. 4A.

FIG. 4I illustrates another exemplary embodiment of a feed bar 38'. In the illustrated embodiment, the feed bar 38' is the same as the embodiment described in FIG. 4A except for its distal end 38b'. The distal end 38b' can be configured to mate with the advancer 40" that will be described in more detail below, and it can be used with the feeder shoe 34' described above. As noted above, the feeder shoe 34' can have a stop mechanism that is able to lock the advancer 40" and the feed bar 38' in place after a proximal-most clip is advanced into the jaws 20. The stop mechanism can be, for example, a tang 82d' formed on the feeder shoe 34' that is adapted to engage a recess 51a formed the feed bar 38', as shown in FIG. 4I. The recess 51a, in combination with the recess 51b, is configured to catch and retain the tang 82d' as the advancer 40" and the feed bar 38' are moved over the feeder shoe 34'. The recesses 51a, 51b can have any size as needed and can be formed on the same side of the feed bar 38' as the detents 84. In the illustrated embodiment, the recesses 51a, 51b are in the shape of a square and have sidewalls configured for receiving the tang 82d' therebetween. Once engaged, the tang 82d' is unable to move out of the recesses 51a, 51b thereby locking the advancer 40" and the feed bar 38' in a locked position. The feed bar 38' can also include an elongated recess 57 formed in its distal end 38b' for receiving the proximal end 53 of the advancer 40" so that the two components can be mated together as described below.

FIG. 5A illustrates one exemplary embodiment of an advancer 40 that is adapted to mate to the distal end 38b of the feed bar 38 and which is effective to drive a distal-most clip from the clip track 30 into the jaws 20. A variety of techniques can be used to mate the advancer 40 to the feed bar 38, but in the illustrated embodiment the proximal end 40a of the advancer 40 is in the form of a female connector that is adapted to receive the male connector formed on the distal end 38b of the feed bar 38. The advancer 40 preferably fixedly mates to the feed bar 38, however it can optionally be integrally formed with the feed bar 38. The distal end 40b of the feed bar 38 is preferably adapted to advance a clip into the jaws 20 and thus the distal end 40b of the advancer 40 can include, for example, a clip-pusher member 90 formed thereon. The clip-pusher member 90 can have a variety of shapes and sizes, but in one exemplary embodiment it has an elongate shape with a recess 92 formed in the distal end thereof for seating the bight portion of a clip. The shape of the recess 92 can vary depending on the particular configuration of the clip. The clip-pusher member 90 can also extend at an angle in a superior direction with respect to a longitudinal axis A of the advancer 40. Such a configuration allows the clip-pusher member 90 to extend into the clip track 30 to engage a clip, while the remainder of the advancer 40 extends substantially parallel to the clip track 30.

FIG. 5B illustrates another exemplary embodiment of a clip-pusher member 90' of an advancer 40'. In this embodiment, the clip-pusher member 90' is slightly more narrow and it has a small recess 92' formed in the distal-most end thereof. In use, the advancer 40 can engage and advance only the distal-most clip disposed within the clip track 30 into the jaws 20. This is due to the positioning of the feed bar 38, which is slidably movable between a fixed proximal and distal positions, as previously discussed.

FIGS. 5C and 5D illustrate still another exemplary embodiment of a clip-pusher member or distal tip 90" of an advancer 40". In this embodiment, the clip-pusher member or distal tip 90" has been modified to allow an apex of a surgical clip being advanced into the jaws to move in superior and inferior directions while still maintaining contact with the apex of the surgical clip. In addition, and as noted above, the advancer 40" can include a recess 51b formed near a proximal end 53 thereof. The recess 51b can have any size and shape as needed to catch and hold the tang 82d' formed on the feeder shoe 34' such that the advancer 40", as well as the feed bar 38' to which the advancer 40" is coupled, is locked in position and unable to move to an open position after a proximal-most clip is advanced into the jaws 20.

With regard to the distal tip 90", in general, the distal tip 90" has an elongate configuration with a proximal end 90p" that is coupled to a body portion or shaft 42" of the advancer 40". The shaft 42" can have various shapes and sizes, but in the illustrated embodiment the shaft 42" has a generally planar configuration with superior and inferior surfaces 42s''', 42i'''. The particular configuration of the shaft 42", with the exception of the distal tip 90", can be similar to the embodiments previously described herein. In an exemplary embodiment, the distal tip 90" and the shaft 42" can be formed as a single integral component, however each component can be formed from different materials. For example, the distal tip 90" can be formed from a metal, while the entire shaft 42" or a portion of the shaft 42" can be formed from a plastic that is integral to the feed bar 38 and is overmolded onto the metal distal tip 90". Regardless of the particular material used, the distal tip 90" is preferably formed from a flexible material that allows the tip 90" to deflect in superior and inferior directions relative to the shaft 42". In certain exemplary embodiments, the distal tip 90" can be formed by punching a predetermined shape out of a planar sheet of metal, and then folding opposed sides of the shape together to form the tip as shown, with the inferior surface being hollow.

As indicated above, the distal tip 90" can be configured to allow an apex of a surgical clip being advanced into the jaws by the tip to move in superior and inferior directions while still maintaining contact with the apex of the clip. In other words, the distal tip 90" can have a height that is greater than a height of the apex, as measured in the superior/inferior direction (i.e., transverse to the longitudinal axis of the advancer 40"). This will allow the apex of the clip to slide up and down along the tip. In particular, as shown in FIG. 5D, a distal-facing surface 41 of the clip-pusher member 90" can have a height H, measured in a superior/inferior direction, that is greater than a height (as measured in the same direction) of an apex of a clip pushed by the clip-pusher member 90", as will be described in more detail below. The increased height can result from a distal biasing surface 43 formed on an inferior surface of the tip 90" and located adjacent to the distal end 90d" of the tip 90". The distal biasing surface 43 can be in the form of a ramped portion or a surface feature. As further shown in FIGS. 5C and 5D, the distal tip 90" can also include a proximal biasing surface 45 formed on an inferior surface of the tip 90" and located adjacent to the proximal end 90p" of the tip 90". The two biasing surfaces 43, 45 can be configured to interact with the tissue stop, as will be described in detail below, and to thereby deflect in superior and inferior directions relative to the tissue stop. The flexible or resilient material used to form the advancer tip 90" can facilitate repeated bending of the distal tip 90". As further shown in FIGS. 5C and 5D, a superior or top portion 47 of the clip-pusher member 90" can be substantially straight and can extend upward at an angle between the proximal end 90p" of the tip 90" and the distal end 90d" of the tip 90". A person skilled in the art will appreciate that the particular configuration of the distal tip 90" can vary depending on the desired movement of the tip during use.

Figure 5E:
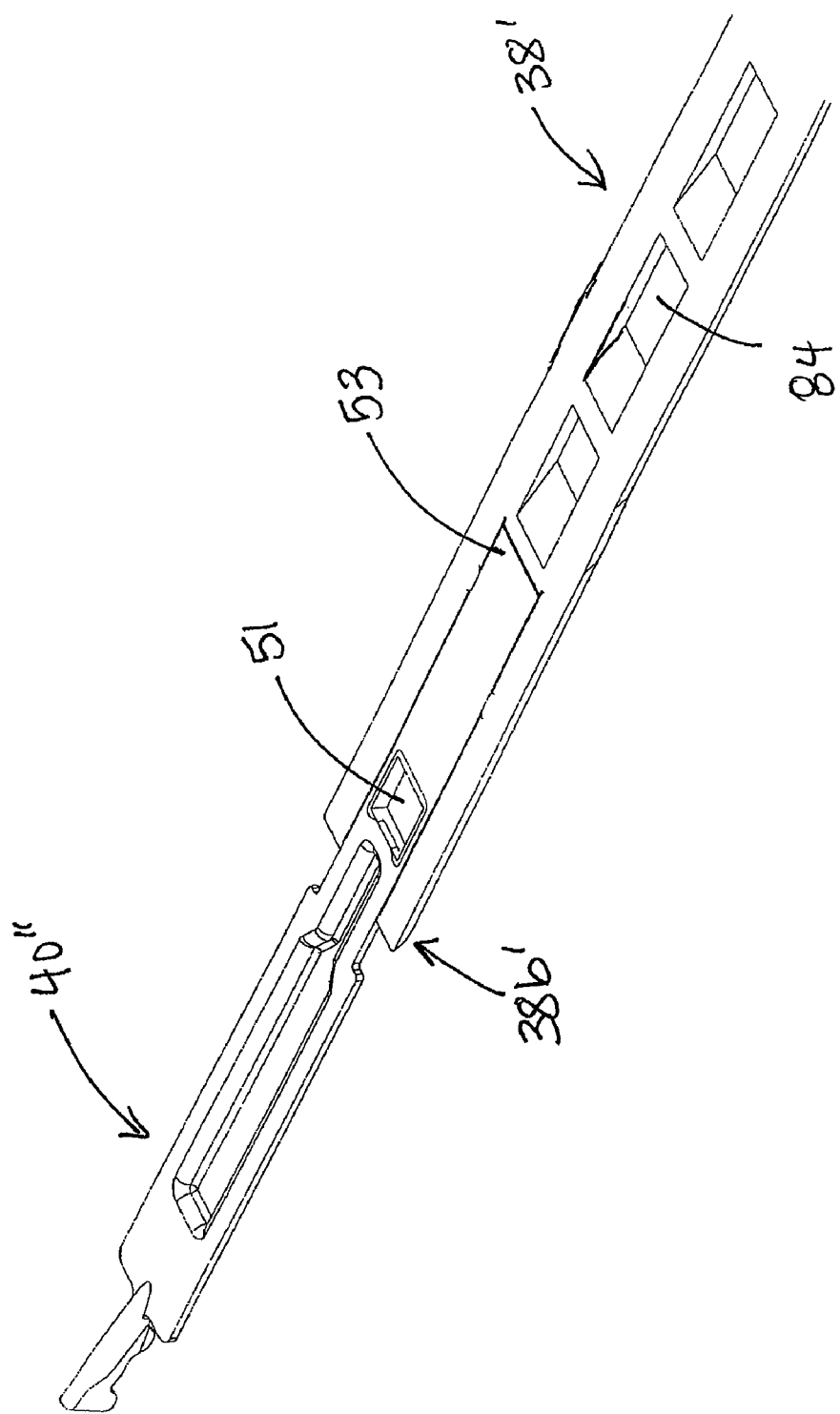
FIG. 5E is a perspective view of the feed bar of FIG. 4I and the advancer of FIGS. 5C and 5D mated together.

FIG. 5E illustrates the advancer 40" and the feed bar 38' mated together. As shown, the distal end 53 of the advancer 40" is disposed within the recess 57 formed in the feed bar 38'. The two can be mated together using any technique known in the art including, but not limited to, press or interference fit, adhesives, fasteners, etc. The recesses 51a, 51b can extend entirely through the proximal end 53 of the advancer 40", and it can extend into the distal end 38b' of the feed bar 38'.

Figure 6C:
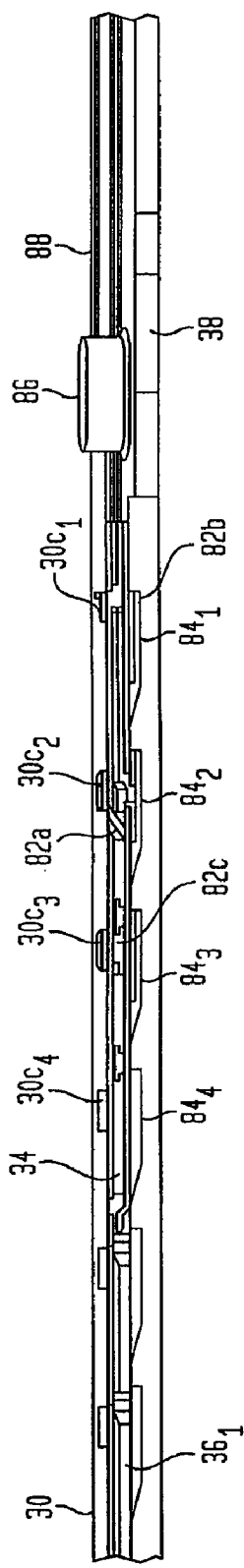
FIG. 6C is a cross-sectional view of the clip advancing assembly shown in FIG. 6B, showing the feed bar moved further distally, thereby moving the feeder shoe and a clip supply disposed distally of the feeder shoe in a distal direction.
Figure 6D:
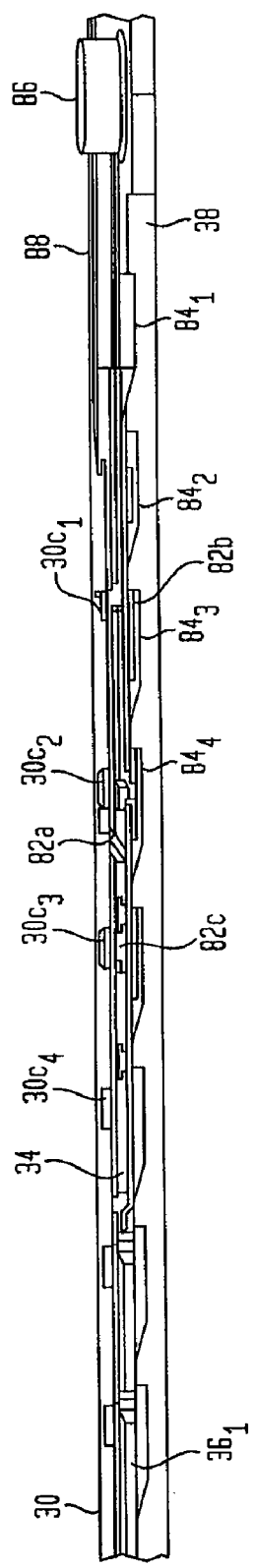
FIG. 6D is a cross-sectional view of the clip advancing assembly shown in FIG. 6C, showing the feed bar returned to the initial, proximal position, shown in FIG. 6A, while the feeder shoe and clip supply remain in the advanced position shown in FIG. 6C.
Figure 6E:
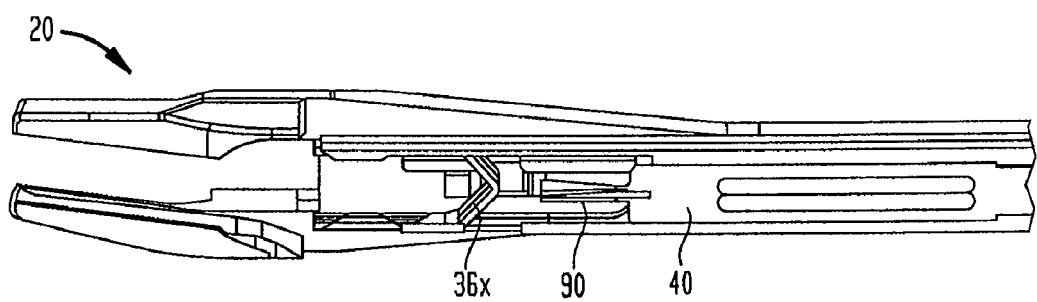
FIG. 6E is a bottom perspective view of the advancer shown in FIG. 5A disposed within the clip track of the jaw retainer assembly shown in FIGS. 2A-2D, showing the advancer in a proximal-most position.
Figure 6F:
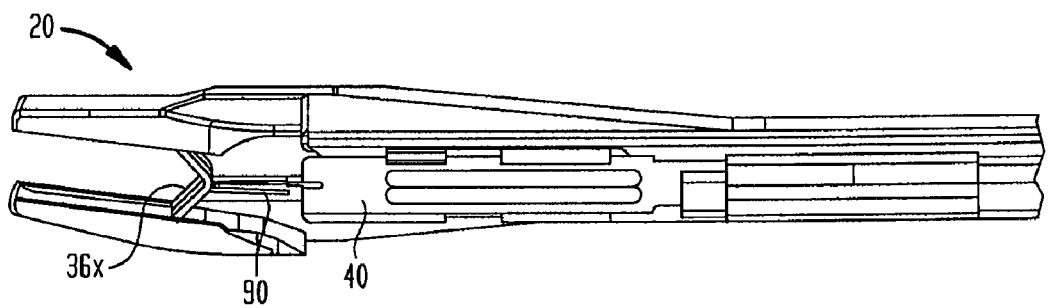
FIG. 6F is a bottom perspective view of the advancer shown in FIG. 6E, showing the advancer in a distal-most position after advancing a clip into the jaws of the surgical clip applier.

FIGS. 6A-6F illustrate the clip advancing assembly in use, and in particular FIGS. 6A-6D illustrate movement of the feed bar 38 within the clip track 30 to advance the feeder shoe 34 and clip supply 36, and FIGS. 6E-6F illustrate movement of the advancer 40 to advance a distal-most clip into the jaws 20. The components in the housing 12 that are used to actuate the clip advancing assembly will be discussed in more detail below.

As shown in FIG. 6A, in the resting position the feed bar 38 is in a proximal-most position such that the protrusion 86 is positioned proximally within the elongate slot 88 in the jaw retainer shaft 28. The feeder shoe 34 is disposed within the clip track 30 and, assuming the device 10 has not yet been used, the feeder shoe 34 is in a proximal-most position such that the superior tang 82a on the feeder shoe 34 is engaged with the proximal-most or first opening $30c_1$ formed in the clip track 30 to prevent proximal movement of the feeder shoe 34, and the inferior tang 82b on the feeder shoe 34 is positioned between the first detent $84_1$ and the second detent $84_2$ in the feed bar 38, such that the inferior tang 82b is biased in a superior direction by the feed bar 38. The detents 84 in the feed bar are labeled sequentially as $84_k$, $84_2$, etc., and the openings 30c in the clip track 30 are labeled sequentially as $30c_1$, $30c_2$, etc. As is further shown in FIG. 6A, a series of clips 36, labeled sequentially as $36_k$, $36_2$, ... $36_x$ with $36_x$ being the distal-most clip, are positioned within the clip track 30 distal of the feeder shoe 34.

Upon actuation of the trigger 16, the feed bar 38 is advanced distally, causing the protrusion 86 to slide distally within the slot 88. As the feed bar 38 moves distally, the inferior tang 82b on the feeder shoe 34 will slide into the first detent $84_1$ in the feed bar 38. Further distal movement of the feed bar 38 will cause the first detent $84_1$ to engage the inferior tang 82b, as shown in FIG. 6B, and to move the feeder shoe 34 and clip supply $36_k$, $36_2$, etc. in a distal direction. As shown in FIG. 6C, when the protrusion 86 abuts the distal end of the elongate slot 88 in the jaw retainer shaft 28, the feed bar 38 is prevented from further distal movement. In this position, the feeder shoe 34 has advanced a predetermined distance to advance the clip supply $36_k$, $36_2$, ... $36_x$ within the clip track 30 by a predetermined distance. The superior tang 82a of the feeder shoe 34 has been advanced into the second opening $30c_2$ in the clip track 30 to prevent proximal movement of the feeder shoe 34, and the inferior tang 82b on the feeder shoe 34 is still engaged by the first detent $84_1$ in the feed bar 38.

Movement of the feed bar 38 from the initial, proximal-most position, shown in FIG. 6A, to the final, distal-most position, shown in FIG. 6C, will also advance the distal-most clip $36_x$ into the jaws 20. In particular, as shown in FIG. 6E, distal movement of the feed bar 38 will cause the clip-pusher member 90 of the advancer 40, which is attached to the distal end of the feed bar 38, to engage the distal-most clip $36_x$ disposed within the clip track 30 and to advance the clip $36_x$ into the jaws 20, as shown in FIG. 6F. In an exemplary embodiment, the advancer 40 will engage and initiate advancement of the distal-most clip $36_x$ prior to engaging and initiating advancement of the feeder shoe 34. As a result the distal-most clip $36_x$ will advance a distance that is greater than a distance traveled by the feeder shoe 34. Such a configuration allows only the distal-most clip $36_x$ to be advanced into the jaws 20 without accidentally advancing an additional clip into the jaws 20.

Once the clip $36_x$ has been partially or fully formed, the trigger 16 can be released to release the formed clip $36_x$. Release of the trigger 16 will also retract the feed bar 38 in a proximal direction until the protrusion 86 returns to the initial proximal-most position within the elongate slot 88, as shown in FIG. 6D. As the feed bar 38 is retracted proximally, the feeder shoe 34 will not move proximally since the superior tang 82a will engage the second opening $30c_2$ in the clip track 30. The inferior tang 82b will not interfere with proximal movement of the feed bar 38, and once the feed bar 38 is in the initial, proximal-most position, as shown, the inferior tang 82b will be positioned between the second detent $84_2$ and the third detent $84_3$ in the feed bar 38.

The process can be repeated to advance another clip into the jaws 20. With each actuation of the trigger 16, the inferior tang 82b will be engaged by the next detent, i.e., detent $84_2$ formed in the feed bar 38, the superior tang 82a on the feeder shoe 34 will be moved distally into the next opening, i.e., opening $30c_3$ on the clip track 30, and the distal-most clip will be advanced into the jaws 20 and released. Where the device 10 includes a predetermined amount of clips, e.g., seventeen clips, the trigger 16 can be actuated seventeen times. Once the last clip has been applied, the stop, e.g., the third tang 82c, on the feeder shoe 34 can engage the stop tang 118 on the clip track 30 to prevent further distal movement of the feeder shoe 34.

Figure 6G:
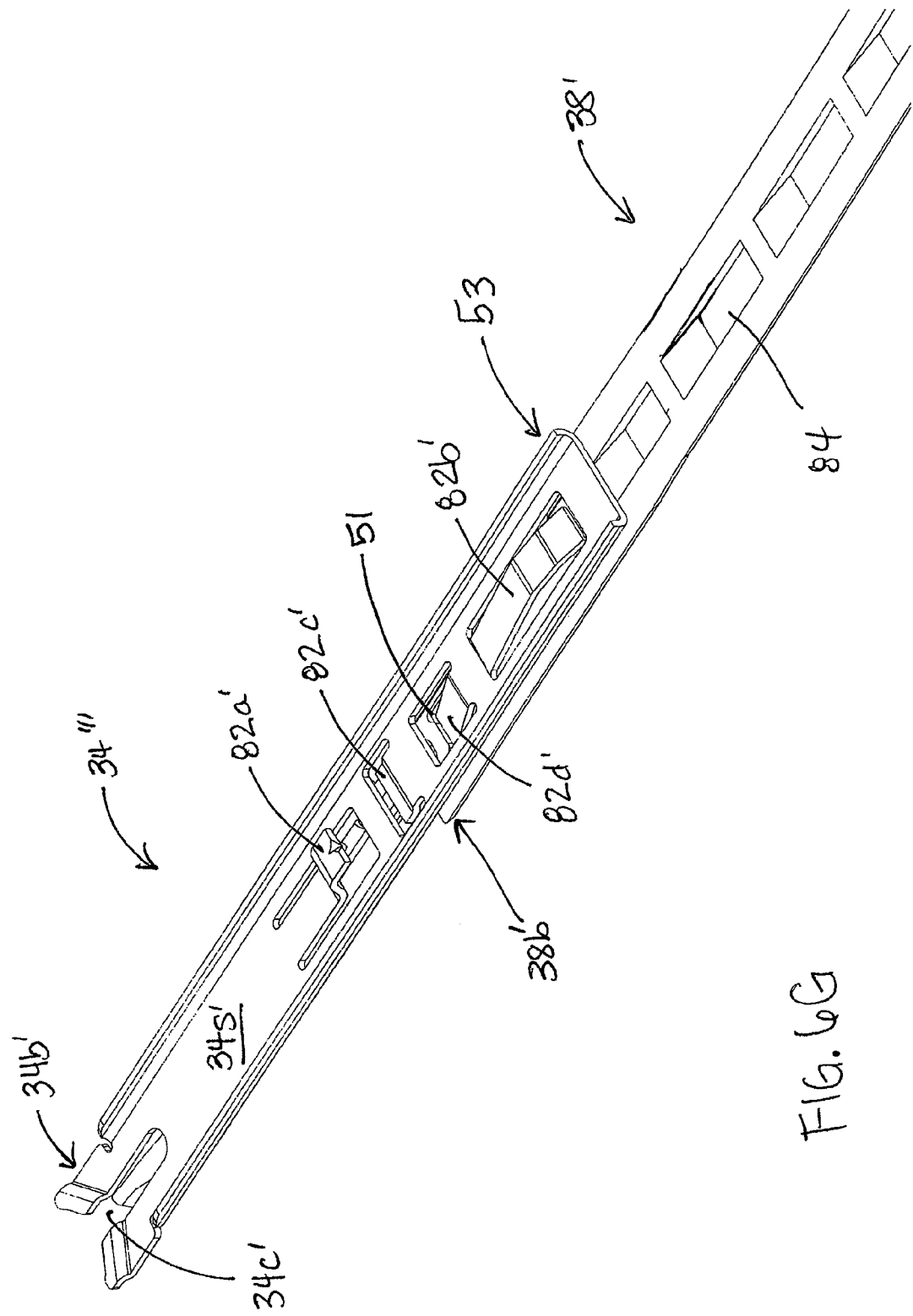
FIG. 6G is a perspective view of one embodiment of a stop mechanism for indicating to a user that a clip supply of an exemplary clip applier is depleted.

As explained above, in another embodiment the clip applier can include a stop mechanism that is effective to lock the trigger 16 in a partially opened position after the last clip is applied, thereby indicating to a user that the last clip has been applied. FIG. 6G illustrates use of a stop mechanism formed between the feed bar 38' of FIG. 4I and the feeder shoe 34''' of FIGS. 3C and 3D. In use, when the last clip is applied to tissue, the stop mechanism can lock the advancer 40" (shown in FIGS. 5C-E) and feed bar 38' in place relative to the feeder shoe 34''' to thereby prevent the trigger 16 from opening to its starting position. In particular, as the feeder shoe 34''' advances the proximal-most clip (i.e., the last clip remaining in the clip track) into position to be advanced into the jaws 20, it moves into sliding engagement with the advancer 40". The trigger 16 can be actuated from its starting position to cause the advancer 40" to move the proximal-most clip into the jaws 20. As the advancer 40" and the feed bar 38' move distally adjacent to the feeder shoe 34''' to move the proximal-most clip into the jaws 20, the recesses 51a, 51b move distally over the tang 82d'. Moving distally, the recesses 51a, 51b do not engage the tang 82d' because the tang 82d' is angled distally. As the trigger 16 is released, however, the advancer 40" and the feed bar 38' begin to move proximally adjacent to the feeder shoe 34'''. Once the recesses 51a, 51b reach the tang 82d', the tang 82d' will extend into and engage the recesses 51a, 51b to lock the advancer 40" and the feed bar 38" in a fixed position, preventing further proximal movement. This engagement between the recesses 51a, 51b and the tang 82d' preferably occurs prior to the trigger being fully opened. In other words, engagement preferably occurs when the trigger 16 is in a partially opened position. Engagement between the feeder shoe 34''' and the advancer 40" and feed bar 38" also preferably occurs when a pawl and ratchet mechanism associated with the trigger is in a position in which the pawl is prevented from rotating, as will be discussed in more detail below. This will prevent further movement of the trigger 16 in either direction. Accordingly, the inability of the trigger to move in any direction will indicate to a user that the clip supply is depleted.

The feeder shoe 34, feed bar 38, and/or the clip track 30 can also optionally include features to prevent accidental or unintentional movement of the feeder shoe 34, for example during shipment of the device. This is particularly advantageous as migration of the feeder shoe 34, particularly prior to first use of the device, can cause the device to malfunction. For example, if the feeder shoe 34 migrates distally, the feeder shoe 34 will advance two clips into the jaws simultaneously, thereby resulting in delivery of two misformed clips. Accordingly, in an exemplary embodiment the feeder shoe 34, feed bar 38, and/or the clip track 30 can include an engagement mechanism and/or can be configured to generate a frictional force therebetween that is sufficient to resist movement, but that can be overcome by actuation of the trigger 16 to allow the feed bar to advance the feeder shoe 34 through the clip track 30.

Figure 27A:
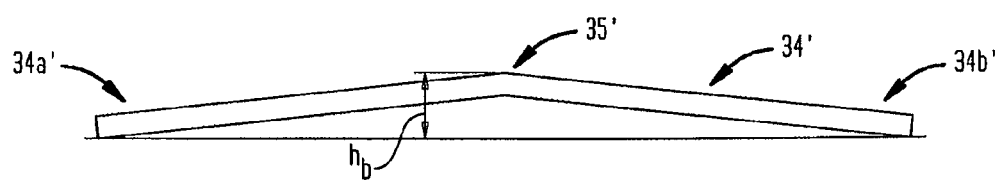
FIG. 27A is a side view illustration showing another embodiment of a feeder shoe having a pre-formed A-shaped bend formed therein and configured to create friction between the feeder shoe and the clip track.

While various techniques can be used to prevent undesirable migration of the feeder shoe 34 within the clip track 30, FIGS. 27A-29C illustrate various exemplary embodiments of techniques for creating friction or an engagement mechanism between the feeder shoe 34, feed bar 38, and/or the clip track 30. Referring first to FIG. 27A, one exemplary embodiment of a feeder shoe 34' is shown having a pre-formed cantilevered or bowed configuration in a free state (i.e., when the feeder shoe 34' is removed from the clip track 30) such that the feeder shoe 34' forms a cantilevered spring when disposed within the clip track 30. In particular, a portion of the feeder shoe 34' can include a bend 35' formed therein such that the opposed ends 34a', 34b' of the feeder shoe 34' are angled relative to one another. The bend 35' can cause the height $h_b$ of the feeder shoe 34' to be greater than the height of the clip track 30. While the height $h_b$ can vary, in an exemplary embodiment the bend 35' is configured to increase a height of the feeder shoe 34' by an amount that is sufficient to create a frictional drag force between the feeder shoe 34' and the clip track 30, but that still allows the feeder shoe 34' to slide within the clip track 30 when the trigger 16 is actuated. In an exemplary embodiment, the height of the feeder shoe 34' is increased at least about 30%, or more preferably about 40%. In use, the clip track 30 will force the feeder shoe 34' into a substantially planar configuration such that the feeder shoe 34' is biased against the clip track 30 when disposed therein. The bend 35' of the feeder shoe 34', as well as the terminal ends 34a', 34b' of the feeder shoe 34', will therefore apply a force to the clip track 30, thereby creating a frictional drag force between the feeder shoe 34' and the clip track 30. The frictional force will prevent the feeder shoe 34' from migrating relative to the clip track 30 unless the trigger 16 is actuated, in which case the force applied by the trigger 16 will overcome the frictional forces.

Figure 27B:
FIG. 27B is a side view illustration of another embodiment of a feeder shoe having a pre-formed V-shaped bend formed therein and configured to create friction between the feeder shoe and the clip track.

A person skilled in the art will appreciate that the bend 35' can have a variety of configurations, and it can be formed anywhere along the length of the feeder shoe 34'. In FIG. 27A the bend 35' is formed at or near the mid-portion of the feeder shoe 34'. The bend 35' can also extend in various directions. While FIG. 27A illustrates the bend 35' extending in a direction perpendicular to the axis such that the bend 35' and the ends 34a', 34b' apply a force to the clip track 30, the bend 35' can alternatively extend along a longitudinal axis of the feeder shoe 34' such that the feeder shoe 34' applies a force to the opposed side rails 80a, 80b (FIG. 2D) of the clip track 30. The bend 35' can also angle the opposed ends 34a', 34b' in a downward direction, as shown in FIG. 27A, such that the feeder shoe 34' is substantially A-shaped, or alternatively the bend 35" can angle the opposed ends 34a'', 34b'' in an upward direction, as shown in FIG. 27B, such that the feeder shoe 34'' is substantially V-shaped. The feeder shoe 34' can also include any number of bends formed therein. A person skilled in the art will appreciate that the particular configuration of the bend(s) can be modified based on the properties of the feeder shoe 34' and the clip track 30 to obtain a desired amount of frictional force therebetween.

Figure 28A:
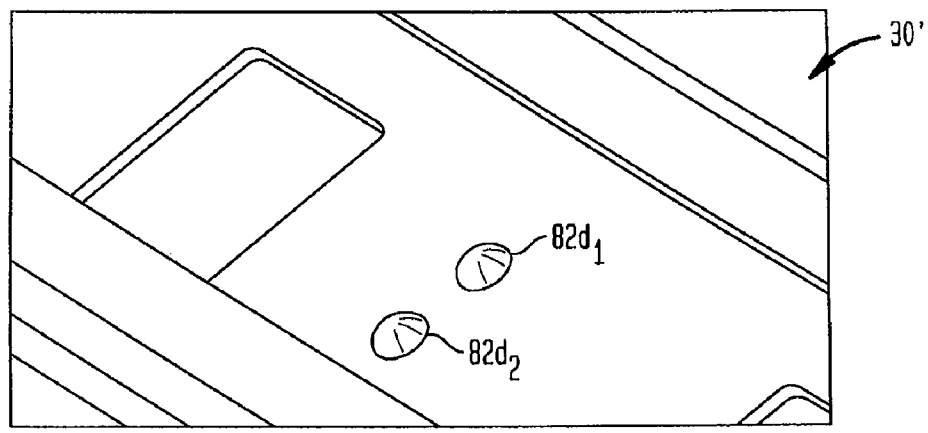
FIG. 28A is a perspective top view of a portion of a clip track having surface protrusions formed therein and configured to create friction between with the feeder shoe according to another embodiment of the invention.
Figure 28B:
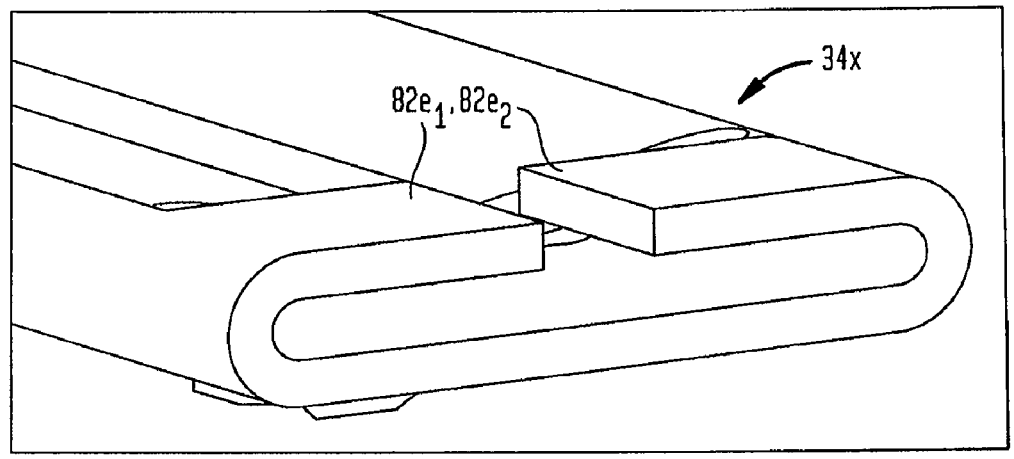
FIG. 28B is perspective end view of another embodiment of a feeder shoe having a tang formed thereon and adapted to engage the surface protrusions formed in the clip track shown in FIG. 28A.

FIGS. 28A and 28B illustrate another embodiment of a technique for creating frictional forces between the feeder shoe and clip track. In this embodiment, the clip track 30' and/or the feeder shoe $34_x$ can include one or more surface protrusions formed thereon. As shown in FIG. 28A, two surface protrusions $82d_1$, $82d_2$ are formed on the clip track 30'. While the surface protrusions $82d_1$, $82d_2$ can be formed at various locations on the clip track 30', including inside the opposed side rails or along the entire length of the clip track 30', or at various locations on the feeder shoe $34_x$, in the illustrated embodiment two protrusions $82d_1$, $82d_2$ are formed adjacent to the proximal end of the clip track 30' and they are positioned to prevent initial migration of the feeder shoe prior to use, e.g., during shipping. The size of the protrusions $82d_1$, $82d_2$ can vary depending upon the amount of frictional force necessary to prevent unintentional migration of the feeder shoe $34_x$.

While the protrusions $82d_1$, $82d_2$ can be configured to provide a sufficient amount of friction to prevent unintentional migration of the feeder shoe $34_x$, the feeder shoe $34_x$ and/or clip track 30' can optionally include a feature that is adapted to engage corresponding surface protrusions. FIG. 28B illustrates opposed tangs $82e_1$, $82e_2$ formed on a distal portion of the feeder shoe $34_x$ for engaging the protrusions $82d_1$, $82d_2$ on the clip track 30'. The tangs $82e_1$, $82e_2$ can vary in shape and size, and they can include a lip or other protrusion configured to engage or "catch" the protrusions $82d_1$, $82d_2$. As shown in FIG. 28B, the tangs $82e_1$, $82e_2$ extend toward one another from opposed sidewalls of the feeder show $34_x$.

Figure 29A:
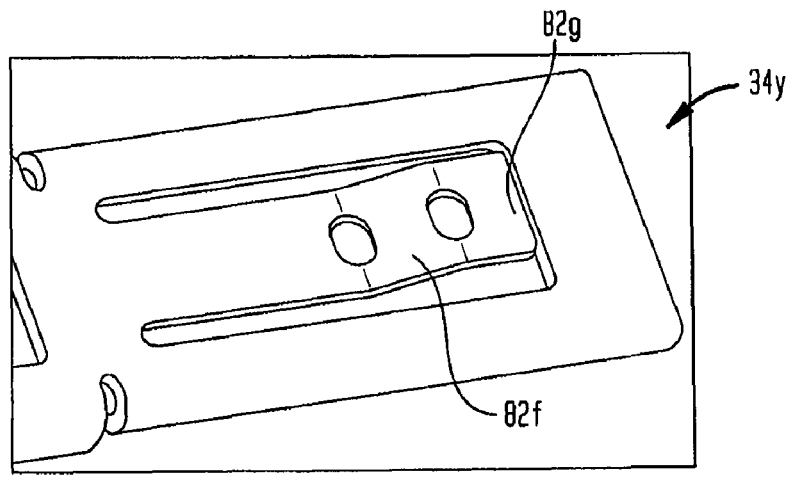
FIG. 29A is a bottom perspective view of another embodiment of a feeder shoe having a holdback lip formed on a tang that is adapted to engage a corresponding groove formed in a feed bar.
Figure 29B:
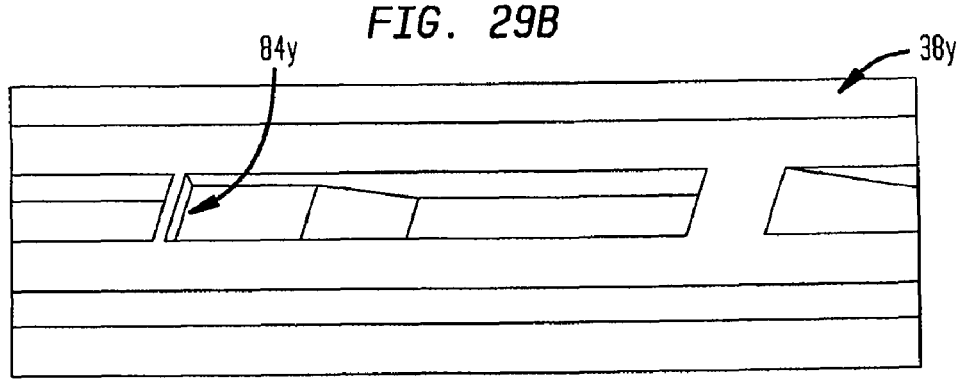
FIG. 29B is a top perspective view of another embodiment of a feed bar having a catch groove formed therein and adapted to be engaged by the holdback lip formed on the tang of the feeder shoe shown in FIG. 29A.
Figure 29C:
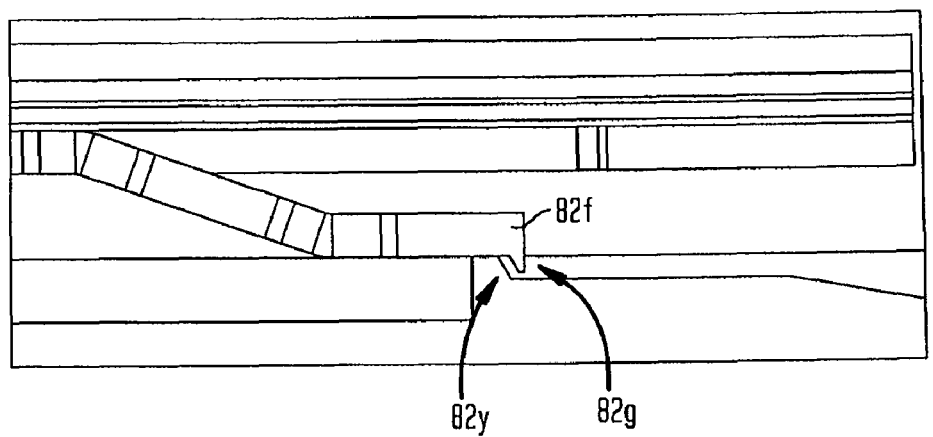
FIG. 29C is a side cross-sectional view of the feeder shoe of FIG. 29A disposed within and engaging the feed bar of FIG. 29B.

FIGS. 29A-29C illustrate another embodiment of a technique for preventing unintentional migration of the feeder shoe. In this embodiment, friction is generated between the feeder shoe and the feed bar. In particular, the feeder shoe $34_y$ includes a tang $82_f$ with a lip $82_g$ formed thereon, as shown in FIG. 29A, and the feed bar $38_y$ includes a corresponding groove $84_y$ formed therein. In use, as shown in FIG. 29C, the lip $82_g$ is configured to engage the groove $84_y$ to prevent unintentional migration of the feeder shoe $34_y$. The lip $82_g$ and groove $84_y$, however, are configured to allow movement of the feeder shoe 34y when a sufficient force is applied to the feeder shoe $34_y$ by actuation of the trigger 16.

A person skilled in the art will appreciate that a variety of other techniques can be used to prevent unintentional migration of a feeder shoe or other clip advancement mechanism within a clip track, and that any combination of features can be used and positioned at various locations on one or both components.

Figure 7:
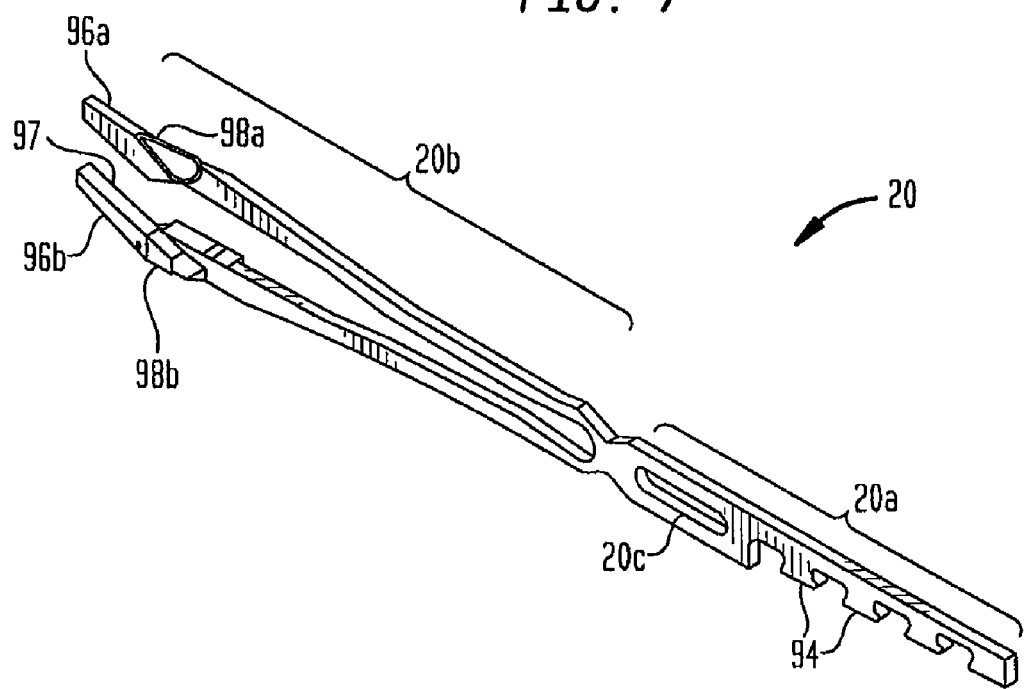
FIG. 7 is a side perspective view of a pair of jaws of the surgical clip applier shown in FIG. 1A.
Figure 8:
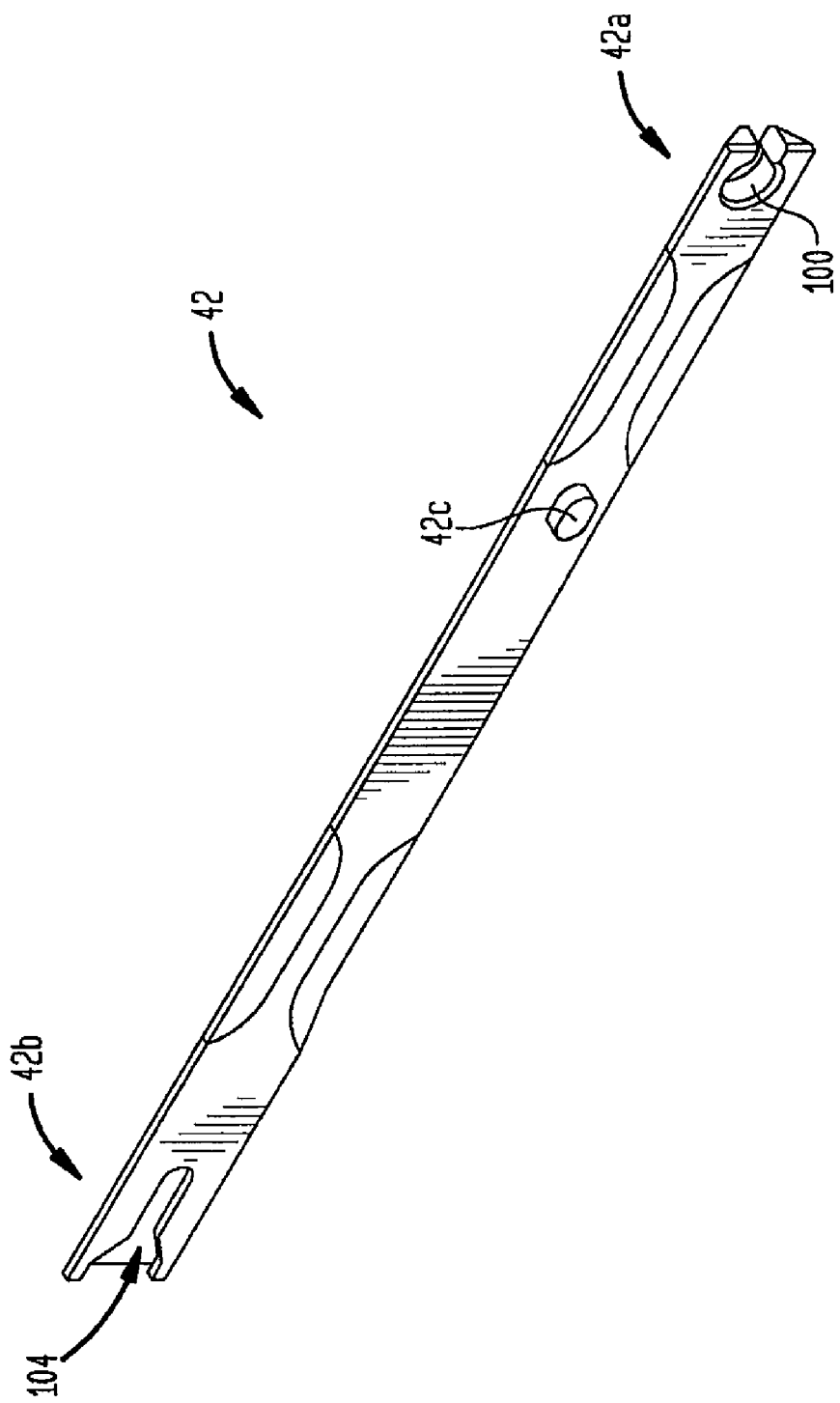
FIG. 8 is a side perspective view of a cam for use with the jaws shown in FIG. 7.

FIGS. 7-9 illustrate various exemplary components of a clip forming assembly. Referring first to FIG. 7, an exemplary embodiment of the jaws 20 are shown. As previously mentioned, the jaws 20 can include a proximal portion 20a having teeth 94 for mating with corresponding teeth 78 formed on the jaw retaining shaft 28. Other techniques can, however, be used to mate the jaws 20 to the jaw retaining shaft 28. For example, a dovetail connection, a male-female connection, etc., can be used. Alternatively, the jaws 20 can be integrally formed with the retaining shaft 28. The distal portion 20b of the jaws 20 can be adapted to receive a clip therebetween, and thus the distal portion 20b can include first and second opposed jaw members 96a, 96b that are movable relative to one another. In an exemplary embodiment, the jaw members 96a, 96b are biased to an open position, and a force is required to move the jaw members 96a, 96b toward one another. The jaw members 96a, 96b can each include a groove (only one groove 97 is shown) formed therein on opposed inner surfaces thereof for receiving the legs of a clip in alignment with the jaw members 96a, 96b. The jaws members 96a, 96b can also each include a cam track 98a, 98b formed therein for allowing the cam 42 to engage the jaw members 96a, 96b and move the jaw members 96a, 96b toward one another. In an exemplary embodiment, the cam track 98a, 98b is formed on a superior surface of the jaw members 96a, 96b.

FIG. 8 illustrates an exemplary cam 42 for slidably mating to and engaging the jaw members 96, 96b. The cam 42 can have a variety of configurations, but in the illustrated embodiment it includes a proximal end 42a that is adapted to mate to a push rod 44, discussed in more detail below, and a distal end 42b that is adapted to engage the jaw members 96a, 96b. A variety of techniques can be used to mate the cam 42 to the push rod 44, but in the illustrated exemplary embodiment the cam 42 includes a female or keyed cut-out 100 formed therein and adapted to receive a male or key member 102 formed on the distal end 44b of the push rod 44. The male member 102 is shown in more detail in FIG. 9, which illustrates the push rod 44. As shown, the male member 102 has a shape that corresponds to the shape of the cut-out 100 to allow the two members 42, 44 to mate. A person skilled in the art will appreciate that the cam 42 and the push rod 44 can optionally be integrally formed with one another. The proximal end 44a of the push rod 44 can be adapted to mate to a closure link assembly, discussed in more detail below, for moving the push rod 44 and the cam 42 relative to the jaws 20.

As is further shown in FIG. 8, the cam 42 can also include a protrusion 42c formed thereon that is adapted to be slidably received within an elongate slot 20c formed in the jaws 20. In use, the protrusion 42c and the slot 20c can function to form a proximal stop for the clip forming assembly.

Figure 10A:
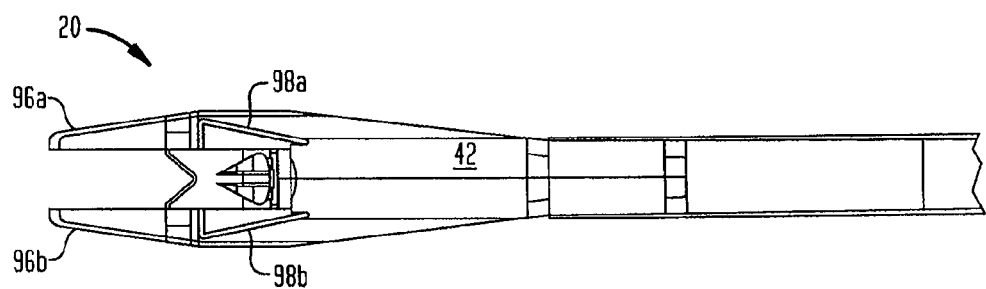
FIG. 10A is a top view of the cam shown in FIG. 8 coupled to the jaws shown in FIG. 7, showing the cam in an initial position and the jaws open.
Figure 10B:
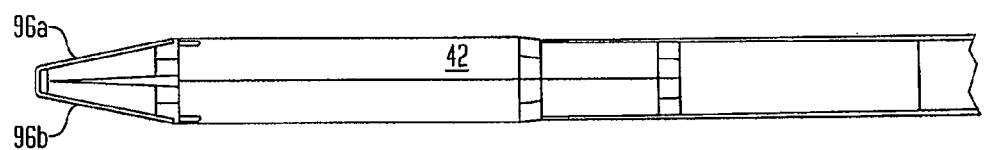
FIG. 10B is a top view of the cam shown in FIG. 8 coupled to the jaws shown in FIG. 7, showing the cam advanced over the jaws and the jaws in a closed position.

Referring back to FIG. 8, the distal end 42b of the cam 42 can be adapted to engage the jaw members 96a, 96b. While a variety of techniques can be used, in the illustrated exemplary embodiment the distal end 42b includes a camming channel or tapering recess 104 formed therein for slidably receiving the cam tracks 98a, 98b on the jaw members 96a, 96b. In use, as shown in FIGS. 10A and 10B, the cam 42 can be advanced from a proximal position, in which the jaw members 96a, 96b are spaced a distance apart from one another, to a distal position, in which the jaw members 96a, 96b are positioned adjacent to one another and in a closed position. As the cam 42 is advanced over the jaw members 96a, 96b, the tapering recess 104 will push the jaw members 96a, 96b toward one another, thereby crimping a clip disposed therebetween.

Figure 11A:
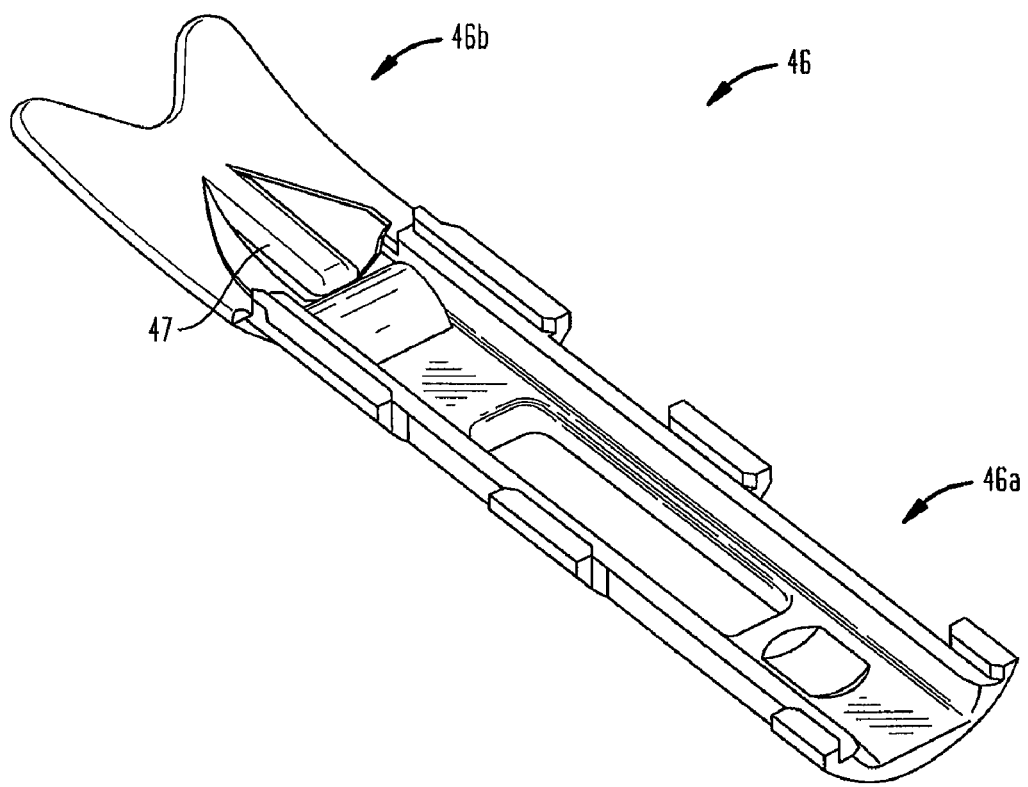
FIG. 11A is a top perspective view of a tissue stop that is adapted to couple to a distal end of the clip track of the jaw retainer assembly shown in FIGS. 2A-2D.

As previously mentioned, the surgical clip applier 10 can also include a tissue stop 46 for facilitating positioning of the tissue at the surgical site within jaws 20. FIG. 11A shows one exemplary embodiment of a tissue stop 46 having proximal end and distal ends 46a, 46b. The proximal end 46a can be adapted to mate to a distal end of the clip track 30 for positioning the tissue stop 46 adjacent to the jaws 20. However, the tissue stop 46 can be integrally formed with the clip track 30, or it can be adapted to mate to or be integrally formed with a variety of other components of the shaft 18. The distal end 46b of the tissue stop 46 can have a shape that is adapted to seat a vessel, duct, shunt, etc. therebetween to position and aligned the jaws 20 relative to the target site. As shown in FIG. 11A the distal end 46b of the tissue stop 46 is substantially v-shaped. The distal end 46b can also have a curved configuration to facilitate placement of the device through a trocar or other access tube.

The tissue stop, or other components of the device, can also optionally include features to support and stabilize a clip during clip formation. When a clip is being formed between the jaws, the clip can pivot and become misaligned. In particular, as the jaws are closed, the terminal end of each leg of the clip will be moved toward one another. As a result, the jaws will only engage a bend portion on each leg, thus allowing the terminal ends of the legs and the apex of the clip to swing out of alignment with the jaws, i.e., to pivot vertically relative to the jaws. Further closure of the jaws can thus result in a malformed clip. Accordingly, the device can include features to align and guide the clip into the jaws, and to prevent the clip from pivoting or otherwise becoming misaligned during clip formation.

While the alignment feature can have a variety of configurations, and it can be formed on various components of the device, FIG. 11A illustrates a central tang 47 formed at a mid-portion of the distal end 46b of the tissue stop 46 for maintaining a clip in alignment with the tip of the advancer assembly 40. In particular, the central tang 47 can allow the apex of a clip to ride therealong thus preventing the clip from becoming misaligned relative to the advancer assembly 40 that is pushing the clip in a distal direction. A person skilled in the art will appreciate that the tissue stop 46 can have a variety of other configurations, and it can include a variety of other features to facilitate advancement of a clip therealong.

Figure 12A:
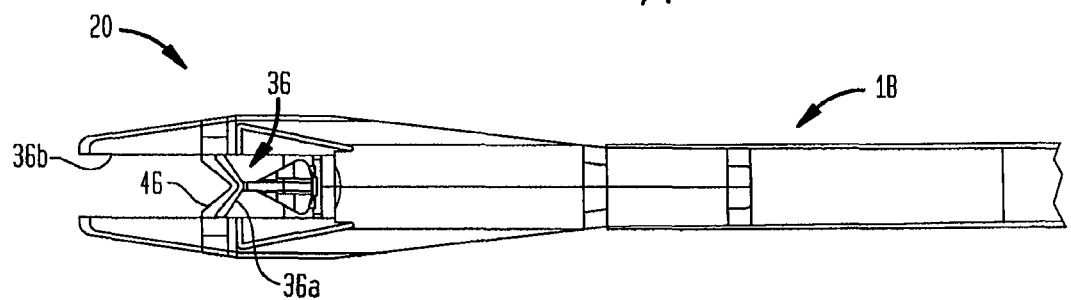
FIG. 12A is a top view of a distal end of the surgical clip applier shown in FIG. 1A showing the tissue stop of FIG. 11A positioned between the jaws of FIG. 7.
Figure 13:
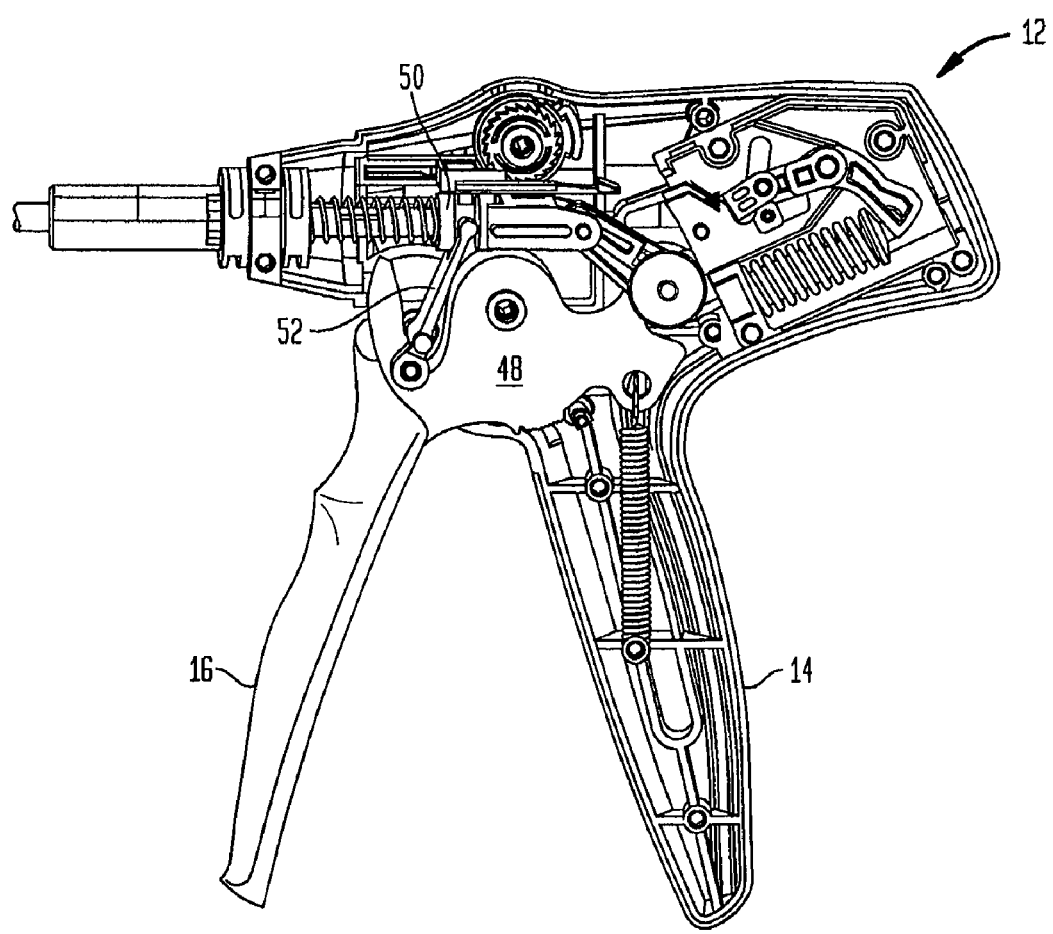
FIG. 13 is a side, partially cross-sectional view of the handle portion of the surgical clip applier shown in FIG. 1A.

FIG. 12A illustrates the tissue stop 46 in use. As shown, the tissue stop 46 is positioned just inferior to the jaws 20 and at a location that allows a vessel, duct, shunt etc. to be received between the jaws 20. As is further shown, a surgical clip 36 is positioned between the jaws 20 such that the bight portion 36a of the clip 36 is aligned with the tissue stop 46. This will allow the legs 36b of the clip 36 to be fully positioned around the vessel, duct, shunt, or other target site.

Figure 11B:
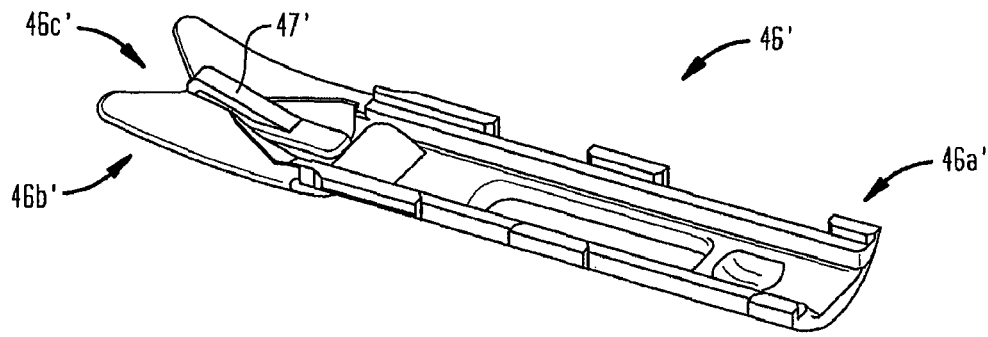
FIG. 11B is a top perspective view of another embodiment of a tissue stop having a ramp formed thereon for guiding a clip into the jaws and stabilizing the clip during clip formation.
Figure 11C:
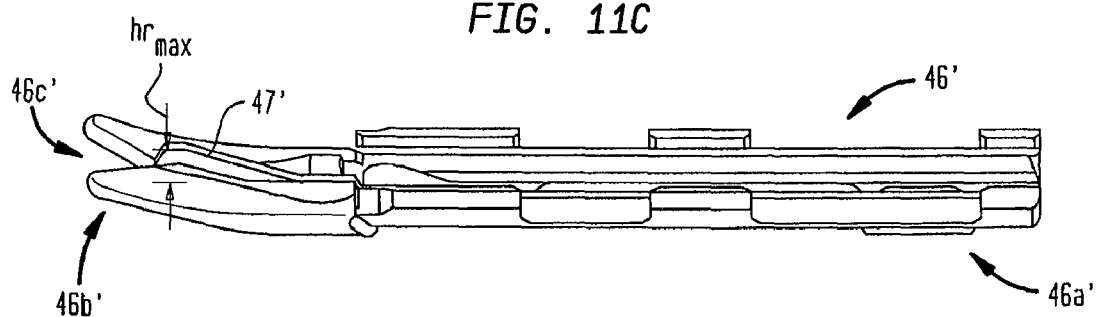
FIG. 11C is a side view of the tissue stop shown in FIG. 11B.
Figure 11D:
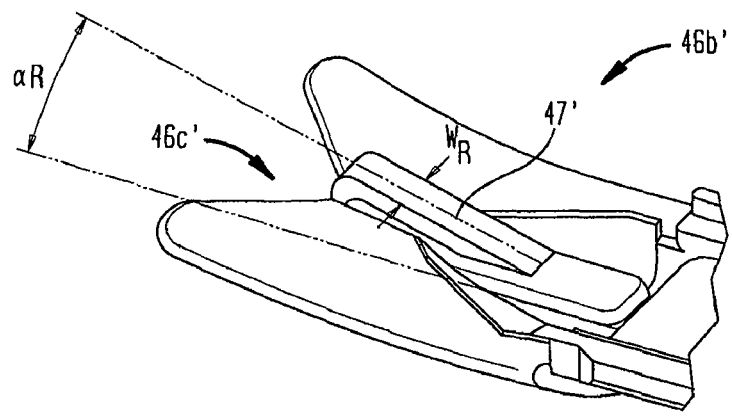
FIG. 11D is an enlarged view of the tissue stop shown in FIGS. 11B and 11C.

FIGS. 11B-11D illustrate another exemplary embodiment of a tissue stop 46' having an alignment feature or guide member formed thereon and adapted to align and guide the clip into the jaws, and more preferably to maintain the clip in alignment with the jaws during clip formation. In this embodiment, the alignment feature is in the form of a ramped member 47' extending longitudinally along a central axis of the tissue stop 46' and protruding above a superior surface of the tissue stop 46'. The ramped member 47' is preferably rigid, and increases in height from a proximal end 46a' to a distal end 46b' of the tissue stop 46'. The angle can vary, however, depending on the particular angle of the jaws. The ramp member 47' preferably terminates just proximal to the tissue-receiving recess 46c' formed in the distal tip of the tissue stop 46'. As a result, the ramped member 47' is positioned just proximal to the jaws 20, thus allowing the ramped member 47' to guide a clip, as well as the tip of the advancer assembly 40 that is pushing the clip, into the jaws 20 at an appropriate angle. In use, the ramped member 47' can abut against an inferior surface of the apex of a clip disposed between the jaws 20 to prevent the clip from pivoting vertically as the jaws 20 are closed to form the clip. In particular, when the advancer assembly 40 is moved to the distal-most position along the ramped member 47', the apex of the clip will abut against the surface of the ramped member 47'. As the clip is compressed between the jaws 20 and the legs of the clip move toward one another, the jaws 20 will only engage a bend portion on each leg. As a result, legs and the apex of the clip are free to pivot vertically. However, since the apex is resting against the superior surface 47a' of the ramped member 47', the ramped member 47' will prevent the apex from moving vertically in a downward or inferior direction, thereby preventing the legs of the clip from moving vertically in an upward or superior direction, i.e., the ramped member 47' will prevent the clip from swinging within the jaws 20. Thus, the ramped member 47' is effective to prevent or limit harmful rotational forces generated when the jaws 20 are closed to form the clip. The clip is thus maintained in alignment with the jaws 20.

A person skilled in the art will appreciate that the shape, size, and configuration of the ramp member can vary depending on the particular configuration of the jaws and other components of the clip applier. In one exemplary embodiment, the ramped member 47' can have a maximum height $h_{Rmax}$ of about 0.025", as measured from a central plane extending through the tissue stop 46'. More preferably the height $h_{Rmax}$ is in the range of about 0.008"" to 0.020", and most preferably the height $h_{Rmax}$ is in the range of about 0.010" to 0.015". The incline angle $\alpha_R$ of the ramped member 47' can also vary, but in an exemplary embodiment the ramped member 47' has an incline angle $\alpha_R$ in the range of about 5° to 45°, and more preferably 5° to 30°, and most preferably 10° to 20°. The width $w_r$ of the ramped member 47' can also vary, but in an exemplary embodiment the ramped member 47' preferably has a width $w_r$ that is slightly less than a space between the jaws 20 in the fully closed position.

FIGS. 11E and 11F illustrate another exemplary embodiment of a tissue stop 46" having proximal and distal ends 46a", 46b". The proximal end 46a" can be adapted to mate to a distal end of the clip track 30 for positioning the tissue stop 46" adjacent to the jaws 20. However, in other embodiments the tissue stop 46" can be integrally formed with the clip track 30, or it can be adapted to mate to or be integrally formed with a variety of other components of the shaft 18. The distal end 46b" of the tissue stop 46" can have a shape that is adapted to seat a vessel, duct, shunt, etc. therebetween to position and align the jaws 20 relative to the target site. For example the tissue stop 46" can have a V-shape that is defined, at least in part, by first and second arms 39a, 39b.

In this embodiment, the tissue stop 46", also referred to as a guide member or advancer guide, is particularly configured for use with the advancer 40" shown in FIGS. 5C and 5D. In particular, the tissue stop 46" includes features to accommodate the increased height of the advancer tip 90" as previously discussed. As shown in FIGS. 11E and 11F, the tissue stop 46" can include an opening or channel 49 formed therein and adapted to allow the distal tip 90" of the advancer 40" to deflect in an inferior direction, i.e., into or through the channel 49, during movement of the advancer 40" between proximal and distal positions. While the channel 49 can be located at any position on the tissue stop 46", in the embodiment the channel 49 is disposed at a central to proximal location longitudinally along the tissue stop 46". The channel 49 can also be located in a recessed track 46t formed in a superior surface 46s of the tissue stop 46", such that the channel 49 is located a distance apart and inferior to the superior surface 46s. The recessed track 46t can be in the form on a longitudinally extending cut-out formed along a substantial portion of the tissue stop 46", so as to create opposed side rails 46r extending longitudinally along a substantial length of the tissue stop 46". The guide rails 46r allow the advancer 40" to slide there along at a location above the channel 49.

As further shown in FIGS. 11E and 11F, the recessed track 46t can include a sloped or ramped surface adjacent to proximal and distal ends of the channel 49, such that the channel 49 includes a distal ramp 51 and a proximal ramp 53. The distal ramp 51 can increase in height in the inferior to superior direction from a proximal end to a distal end. The distal ramp 51 can function to deflect the advancer tip 90" in a superior direction as the advancer 40" is advanced distally. The proximal ramp 53 can increase in height in the inferior to superior direction from a distal end to a proximal end. The proximal ramp 53 can function to deflect the advancer tip 90" in a superior direction as the advancer 40" is advanced proximally.

As further shown in FIGS. 11E and 11F, the tissue stop 46" can also include a longitudinally-extending groove 55 located distal to the channel 49 and adjacent to the distal end. The groove 55 can extend along the longitudinal axis of the tissue stop 46" in a substantially central location laterally between the first and second arms 39a, 39b and it can be positioned substantially directly in line with the channel 49 such that the distal tip 90" traveling distally up the distal ramp 51 and out of the channel 49 can continue traveling in a straight line along the groove 55 to move a clip over the tissue stop 46". In other words, the groove 55 substantially prevents the distal tip 90" from moving laterally relative to opposed lateral sides of the tissue stop 46" to keep the tip 90" in alignment with the apex of the clip. In some embodiments, the groove 55 can be recessed below a top surface of the first and second arms 39a, 39b to accommodate the increased height H of the distal tip 90". Since an apex of a clip generally travels a distance above the tissue stop 46", this allows a height H of a distal tip 90" to extend both above and below the apex of the clip.

As noted above, when the clip is pushed into the jaws 20, the clip must reorient itself to accommodate the angle of the jaws 20. This reorientation can cause an apex of the clip to drop vertically or rotate downward (in an inferior direction) relative to the opposed legs of the clip. This drop may prevent the clip from being positioned properly within the jaws 20. For example, in some cases, the apex of the clip may drop below a distal end of the clip-pusher member such that the clip-pusher member bypasses the clip and moves over top of its apex. The clip-pusher member would then be unable to properly position the clip within the jaws 20. The height H of the clip-pusher member 90" in the embodiment shown in FIGS. 5C and 5D, however, in combination with the groove 55 in the tissue stop 46" in the embodiment shown in FIGS. 11E and 11F, provides a solid surface against which the apex of the clip can move if it pivots in the superior and/or inferior directions. If the apex of the clip drops as it is being pushed into the jaws 20, the distal facing surface 41 of the distal tip 90" can provide a solid surface that extends down into the recessed groove 55, thereby preventing the apex of the clip from slipping beneath the distal tip 90". In this way, an apex of a clip cannot fall below an inferior surface of the distal facing surface 41, thereby allowing the clip to always maintain contact with the distal tip 90" and thus to always be positioned properly within the jaws 20.

FIGS. 12B-12E illustrate an exemplary interaction between the tissue stop 46" and the distal tip 90" in more detail. In FIG. 12B, the distal tip 90" is near the beginning of a clip forming cycle. The distal tip 90" is shown pushing the distal-most clip C into the jaws 20. The next clip $C_1$ can be at a distal position in the clip track 30. As shown, the distal-facing surface 41 of the distal tip 90" is abutting an apex of the clip C and it has a height H that is substantially greater than a height of the apex. The distal-facing surface 41 of the distal tip 90" can travel within the groove 55 of the tissue stop 46" as it pushes the clip C into the jaws 20. In this way, as the legs of the clip C rotate upward (in a superior direction) slightly to enter the jaws 20, the apex of the clip C will always abut against the distal-facing surface 41, even if the apex pivots downward in the inferior direction. More particularly, the inferior surface of the distal tip 90" is in contact with the groove 55, and thus the apex of the clip C will never fall below the inferior surface of the distal tip 90". In this way, the distal-facing surface 41 is able to maintain contact with the apex of the clip C at all times and is therefore able to position the clip C properly within the jaws 20. The distal-facing surface 41 can also maintain contact with the apex of the clip C at all times during forming of the clip C between the jaws 20 to ensure that the clip C does not move proximally.

As illustrated in FIG. 12C, once the clip C is formed within the jaws 20 and released, the distal tip 90" begins moving proximally from its distal-most position within the groove 55 in order to position itself behind or proximal to the next clip $C_1$. At this point in the clip forming cycle, the distal tip 90" is positioned distal to the next clip $C_1$, and the highest point on the superior surface 47 of the distal tip 90" is at substantially the same height as the superior surface of the clip $C_1$. Therefore, as the distal tip 90" moves proximally into contact with the clip $C_1$, the superior surface 47 of the distal tip 90" can contact an inferior surface of an apex of the clip $C_1$. Since the clip $C_1$ is rigidly held within the clip track 30, the clip $C_1$ produces a downward force on the distal tip 90" to deflect the resilient distal tip 90" downward. As the clip $C_1$ and the superior surface 47 of the distal tip 90" contact one another, the distal tip 90" is traveling toward the distal ramp 51. Thus, the downward force applied by the clip $C_1$ can cause the distal tip 90" to deflect downward in an inferior direction such that the distal biasing surface 43 of the distal tip 90" travels down the distal ramp 51 and into or partially through the channel 49. With the distal tip 90" traveling proximally in the channel 49, its superior surface 47 is lower than an inferior surface of the apex of the clip $C_1$ and can thus travel proximally under the inferior surface of the apex of the clip $C_1$, as shown most clearly in FIG. 12D.

As the distal tip 90" continues to move proximally within the channel 49, the distal-facing surface 41 moves proximal to the apex of the clip $C_1$. As it moves proximally, the proximal biasing surface 45 contacts the proximal ramp 53 and begins to move up the proximal ramp 53. Since the superior surface 47 of the distal tip 90" is no longer in contact with the inferior surface of the clip $C_1$, when the proximal biasing surface 45 travels up the proximal ramp 53, the distal tip 90" deflects back up in a superior direction such that it is of a substantially even height with the apex of the clip $C_1$ once again, as shown most clearly in FIG. 12E. The distal tip 90" is now in its proximal-most position and is ready to begin the clip forming cycle over again. Thus, as the advancer 40", and hence the distal tip 90", are moved distally, the distal biasing surface 43 on the distal tip 90" will travel distally along the distal ramp 51 to cause the distal tip 90" to deflect upward in the superior direction, thus ensuring that contact is maintained between the apex of the clip and the distal-facing surface 41 of the distal tip 90".

FIGS. 13-26B illustrate various exemplary internal components of the housing 12 for controlling clip advancement and forming. As previously discussed, the surgical clip applier 10 can include some or all of the features disclosed herein, and it can include a variety of other features known in the art. In certain exemplary embodiments, the internal components of the clip applier 10 can include a clip advancing assembly, that couples to the clip advancing assembly of the shaft 18, for advancing at least one clip through the elongate shaft 18 to position the clip between the jaws 20, and a clip forming assembly, that couples to the clip forming assembly of the shaft 18, for closing the jaws 20 to form a partially or fully closed clip. Other exemplary features include an anti-backup mechanism for controlling movement of the trigger 16, an overload mechanism for preventing overload of the force applied to the jaws 20 by the clip forming assembly, and a clip quantity indicator for indicating a quantity of clips remaining in the device 10.

FIGS. 13-16D illustrate an exemplary embodiment of a clip advancing assembly of the housing 12 for effecting movement of the feed bar 38 within the shaft 18. In general, the clip advancing assembly can include a trigger insert 48 that is coupled to the trigger 16, a feed bar coupler 50 that can mate to a proximal end 38a of the feed bar 38, and a feed link 52 that is adapted to extend between the trigger insert 48 and the feed bar coupler 50 for transferring motion from the trigger insert 48 to the feed bar coupler 50.

Figure 14:
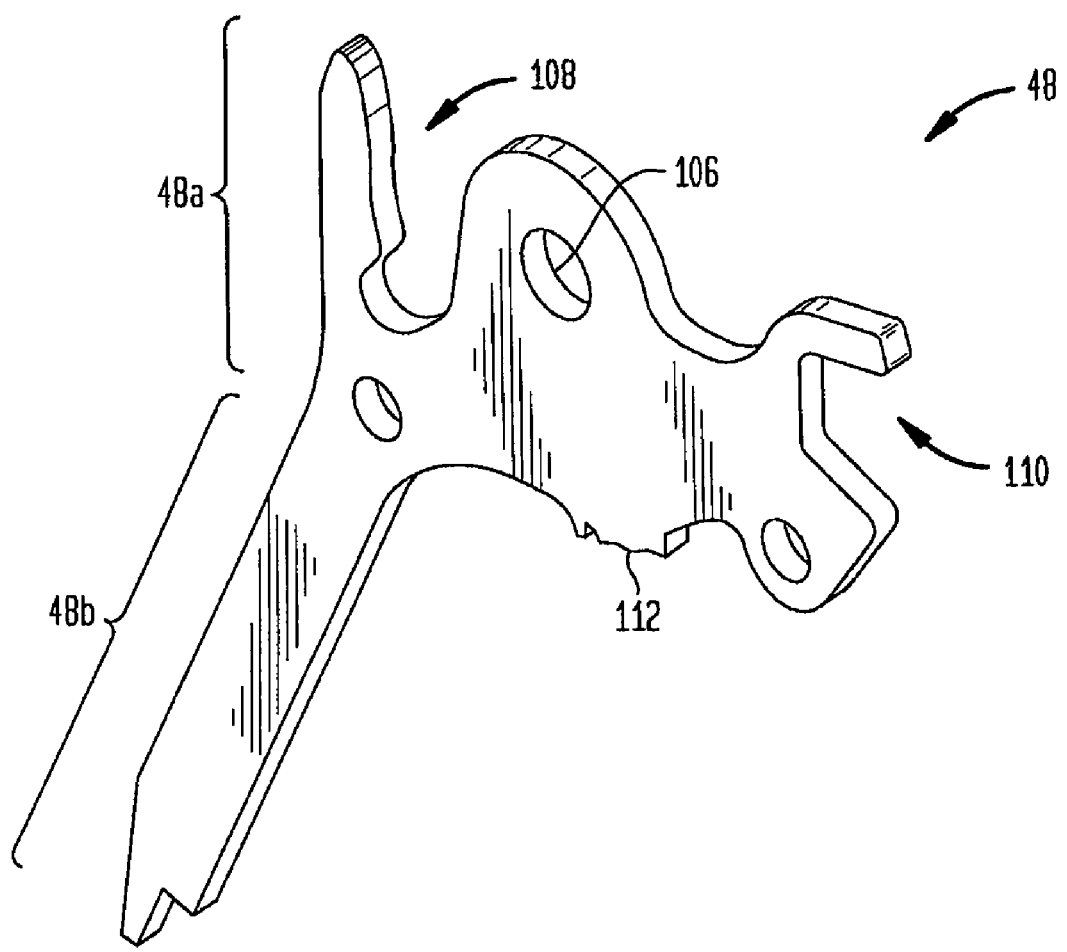
FIG. 14 is a side perspective view of a trigger insert of the surgical clip applier shown in FIG. 1A.

FIG. 14 illustrates the trigger insert 48 in more detail. The shape of the trigger insert 48 can vary depending on the other components of the housing 12, but in the illustrated embodiment the trigger insert 48 includes a central portion 48a that is adapted to pivotally mate to the housing 12, and an elongate portion 48b that is adapted to extend into and mate to the trigger 16. The central portion 48a can include a bore 106 extending therethrough for receiving a shaft for pivotally mating the trigger insert 48 to the housing 12. The central portion 48a can also include a first recess 108 formed in a superior side edge for receiving a portion of the feed link 52. The first recess 108 preferably has a size and shape that allows a portion of the feed link 52 to extend therein such that the feed link 52 will be forced to pivot when the trigger insert 48 pivots due to movement of the trigger 16. As shown in FIG. 14, the first recess 108 is substantially elongate and includes a substantially circular portion formed therein for seating a shaft formed on a proximal end of the feed link 52, as will be discussed in more detail with respect to FIG. 16. The trigger insert 48 can also include a second recess 110 formed in a back side edge for receiving a closure link roller 54 that is coupled to the push bar 44 for moving the cam 42 to close the jaws 20, and ratchet teeth 112 formed on the bottom side edge thereof for mating with a pawl 60 for controlling movement of the trigger 16, as will be discussed in more detail below.

Figure 15A:
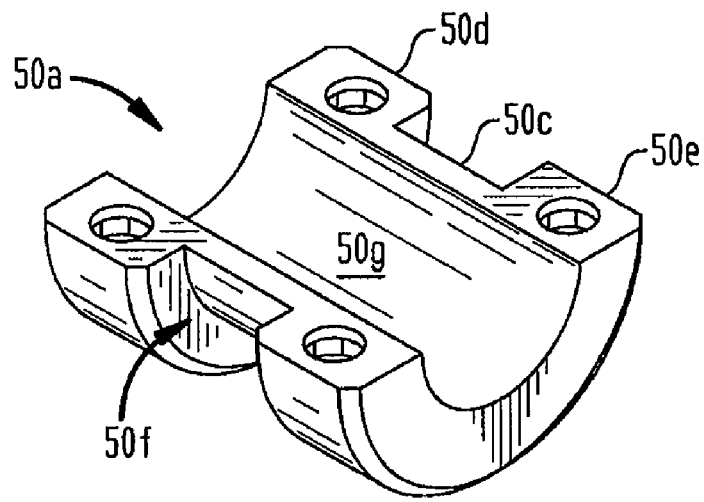
FIG. 15A is a side perspective view of one half of a feed bar coupler of the surgical clip applier shown in FIG. 1A.
Figure 15B:
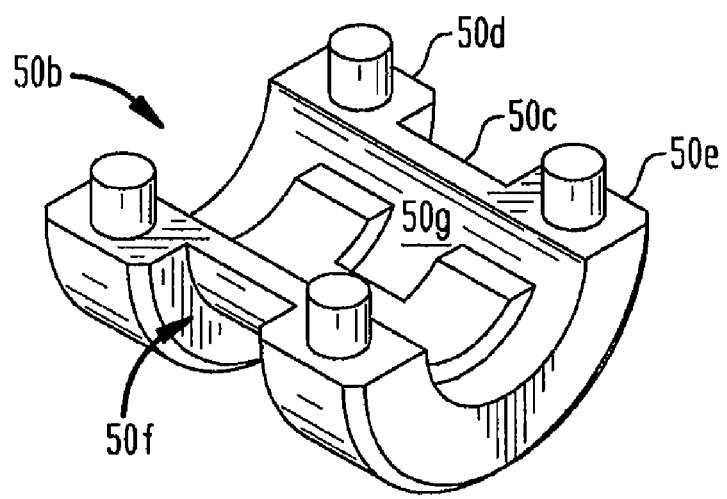
FIG. 15B is a side perspective view of the other half of the feed bar coupler shown in FIG. 15A.

The exemplary feed bar coupler 50 is shown in more detail in FIGS. 15A and 15B, and it can be adapted to couple the proximal end of the feed bar 38 to the distal end of the feed link 52. While a variety of techniques can be used to mate the feed bar coupler 50 to the proximal end 38a of the feed bar 38, in an exemplary embodiment the feed bar coupler 50 is formed from two separate halves 50a, 50b that mate together to maintain the proximal end 38a of the feed bar 38 therebetween. When mated, the two halves 50a, 50b together define a central shaft 50c having substantially circular flanges 50d, 50e formed on opposed ends thereof and defining a recess 50f therebetween for seating a distal portion of the feed link 52. The central shaft 50c defines a lumen 50g therethrough for receiving the proximal end 38a of the feed bar 38 and for locking the feed bar 38 in a substantially fixed position relative to the feed bar coupler 50. The feed bar coupler 50 can, however, be integrally formed with the feed bar 38, and it can have a variety of other shapes and sizes to facilitate mating with the feed link 52.

Figure 16:
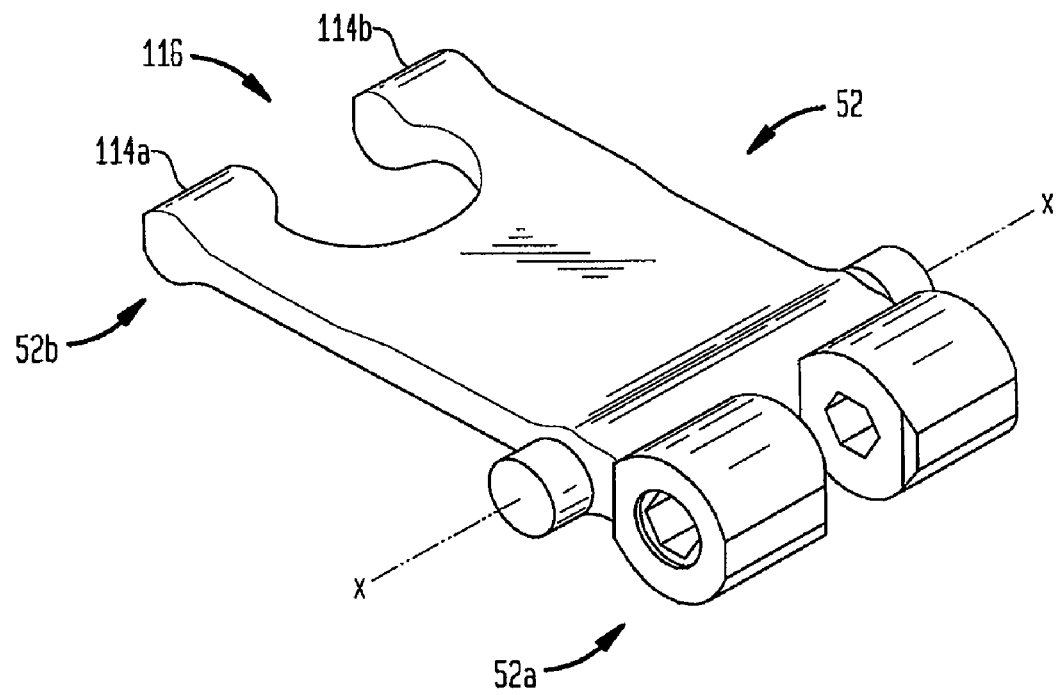
FIG. 16 is a top perspective view of a flexible link that forms part of a clip advancing assembly of the surgical clip applier shown in FIG. 1A.

FIG. 16 illustrates an exemplary feed link 52, which can extend between the trigger insert 48 and the feed bar coupler 52. In general, the feed link 52 can have a substantially planar elongate shape with proximal and distal ends 52a, 52b. The proximal end 52a is adapted to rotatably sit within the first recess 108 of the trigger insert 48 and thus, as previously discussed, it can include a shaft 53 (FIG. 1B) extending therethrough. The shaft 53 can be adapted to pivotally rotate within the first recess 108 of the trigger insert 48, thereby allowing the trigger insert 48 to pivot the feed link 52. The distal end 52b of the feed link 52 can be adapted to couple to feed bar coupler 50 and thus, in an exemplary embodiment, it includes opposed arms 114a, 114b formed thereon and defining an opening 116 therebetween for seating the central shaft 50a of the feed bar coupler 50. The arms 114a, 114b are effective to engage and move the coupler 50 as the feed link 52 pivots about a pivot axis X. The pivot axis X can be defined by the location at which the feed link 52 couples to the housing 12, and it can be positioned anywhere on the feed link 52, but in the illustrated embodiment it is positioned adjacent to the proximal end 52a of the feed link 52.

In an exemplary embodiment, the feed link 52 can be flexible to eliminate the need to calibrate the clip advancing assembly and the clip forming assembly. In particular, the feed link 52 allows the trigger 16 to continue moving toward a closed position even after the feed bar 38 and feed bar coupler 50 are in a distal-most position, and it provides some freedom to the clip forming and clip advancing assemblies. In other words, the trigger 16 is pliant relative to the feed bar 38 during closure of the trigger.

The particular stiffness and strength of the feed link 52 can vary depending on the configuration of the clip advancing assembly and the clip forming assembly, but in one exemplary embodiment the feed link 52 has a stiffness that is in the range of 75 to 110 lbs per inch, and more preferably that is about 93 lbs per inch (as measured at the interface between the link 52 and the feed bar coupler 50), and it has a strength of that is in the range of 25 lbs and 50 lbs, and more preferably that is about 35 lbs. The feed link 52 can also be formed from a variety of materials, including a variety of polymers, metals, etc. One exemplary material is a glass-reinforced polyetherimide, but a number of reinforced thermoplastics could be used, including glass reinforced liquid-crystal polymers, glass-reinforced nylons, and carbon-fiber reinforced versions of these and similar thermoplastics. Fiber-reinforced thermoset polymers such as thermoset polyesters could also be used. Feed link 52 could also be fabricated from a metal, such as spring steel to achieve the desired combination of limited flexibility and controlled strength.

Figure 17A:
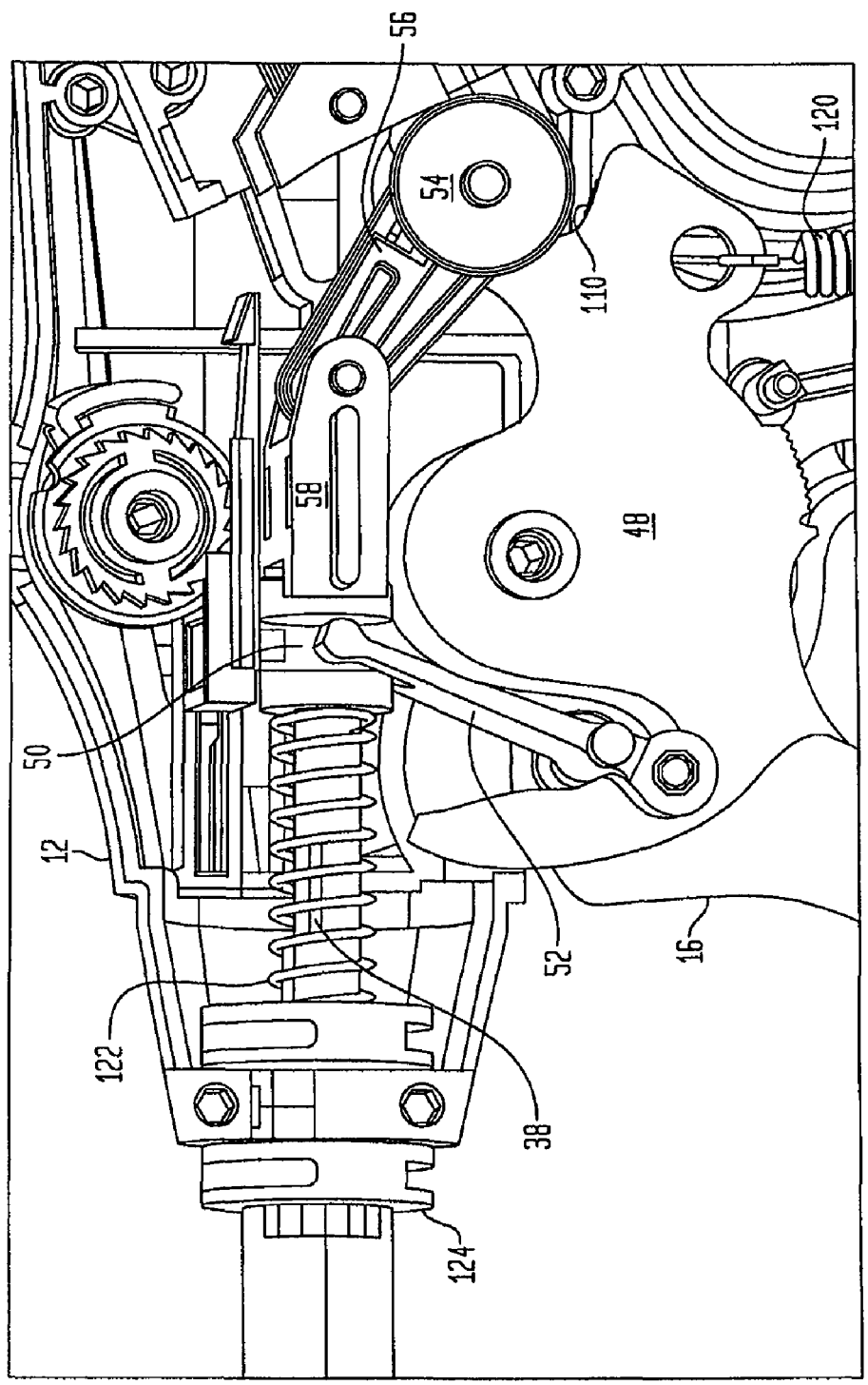
FIG. 17A is a side, partially cross-sectional view of a portion of the handle of the surgical clip applier shown in FIG. 1A, showing a clip advancing assembly in an initial position.

FIGS. 17A-17D illustrate the exemplary clip advancing assembly in use. FIG. 17A shows an initial position, wherein the trigger 16 is resting in an open position, the feed bar coupler 50 and feed bar 38 are in a proximal-most position, and the feed link 52 extends between the trigger insert 48 and the feed bar coupler 50. As previously discussed, in the initial open position the protrusion 86 on the feed bar 38 in positioned in the proximal end of the elongate slot 88 in the jaw retainer shaft 28. A first biasing member, e.g., spring 120, is coupled to the trigger insert 48 and the housing 12 to maintain the trigger insert 48 and trigger 16 in the open position, and a second biasing member, e.g., spring 122, extends between a shaft coupler 124, which rotatably mates the shaft 18 to the housing 12, and the feed bar coupler 50 to maintain the feed bar coupler 50 and feed bar 38 in the proximal-most position.

Figure 17B:
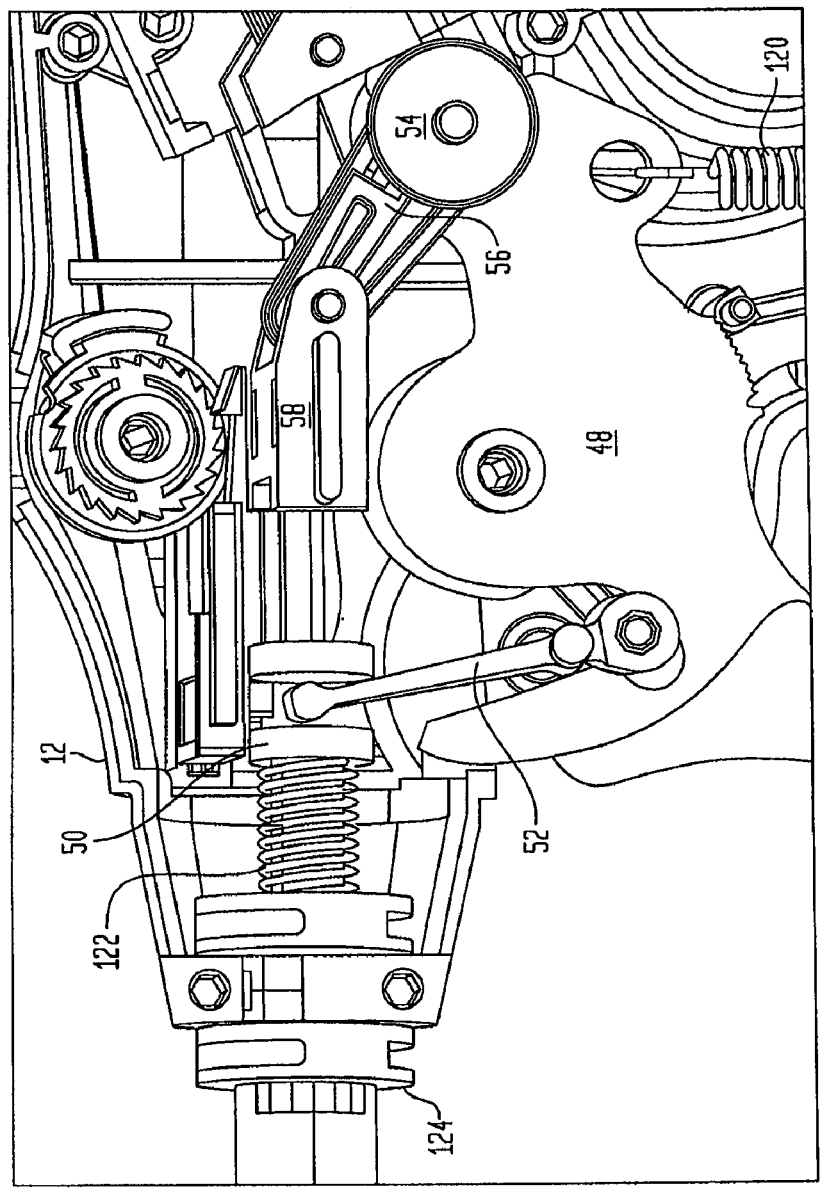
FIG. 17B is a side, partially cross-sectional view of a portion of the handle of the surgical clip applier shown in FIG. 17A, showing the clip advancing assembly partially actuated.

When the trigger 16 is actuated and moved toward the closed position, i.e., toward the stationary handle 14, to overcome the biasing forces applied by the springs 120, 122, the trigger insert 48 begins to pivot in a counter-clockwise direction, as shown in FIG. 17B. As a result, the feed link 52 is forced to pivot in a counter-clockwise direction, thereby moving the feed bar coupler 50 and feed bar 38 in a distal direction. The protrusion 86 on the feed bar 38 thus moves distally within the elongate slot 88 in the jaw retainer shaft 28, thereby advancing the feeder shoe 34 and the clips 36 disposed within the clip track. Spring 120 is extended between the housing and the trigger insert 48, and spring 122 is compressed between the feed bar coupler 50 and the shaft coupler 124.

Figure 17C:
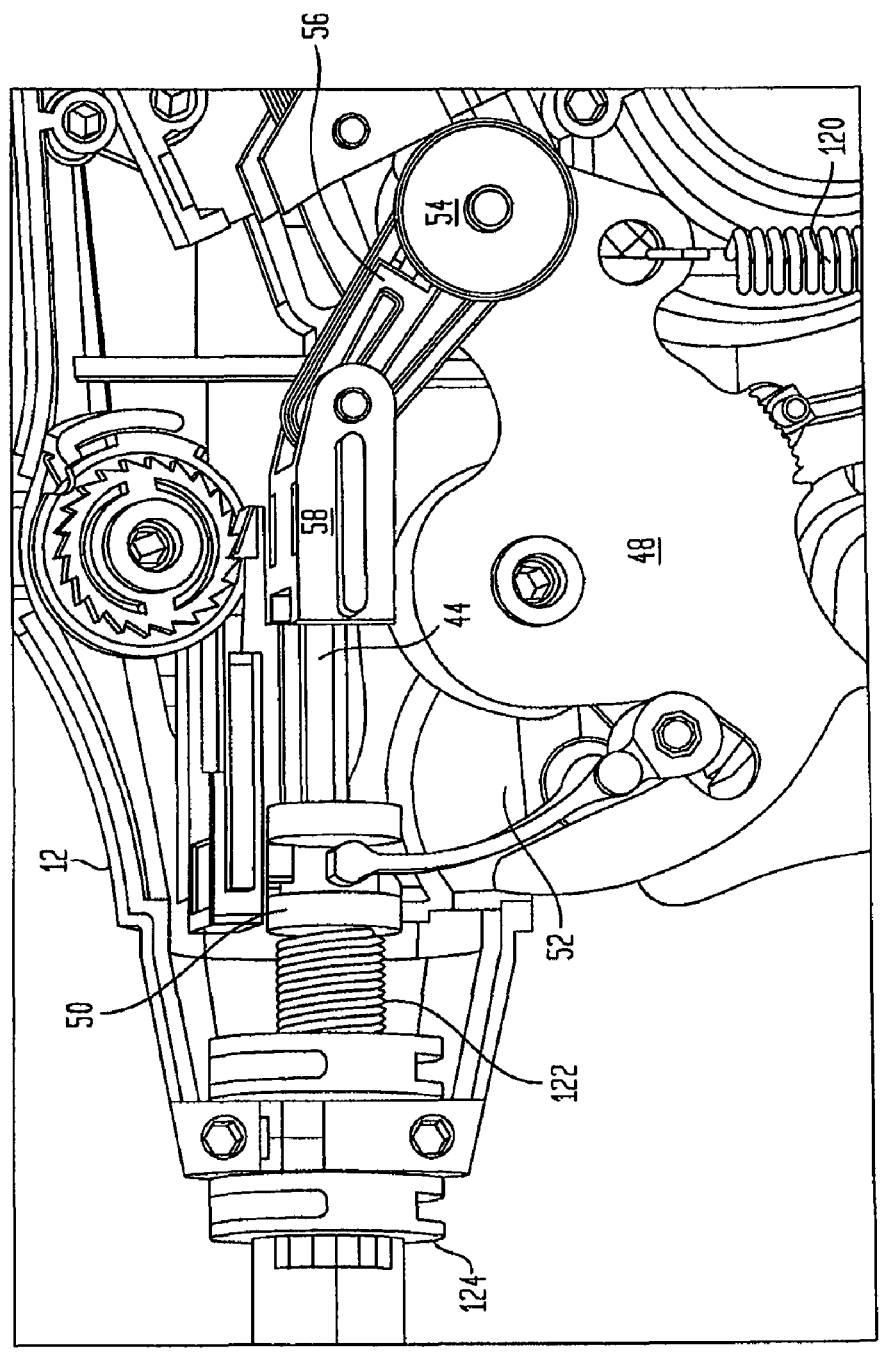
FIG. 17C is a side, partially cross-sectional view of a portion of the handle of the surgical clip applier shown in FIG. 17B, showing the clip advancing assembly fully actuated.
Figure 17D:
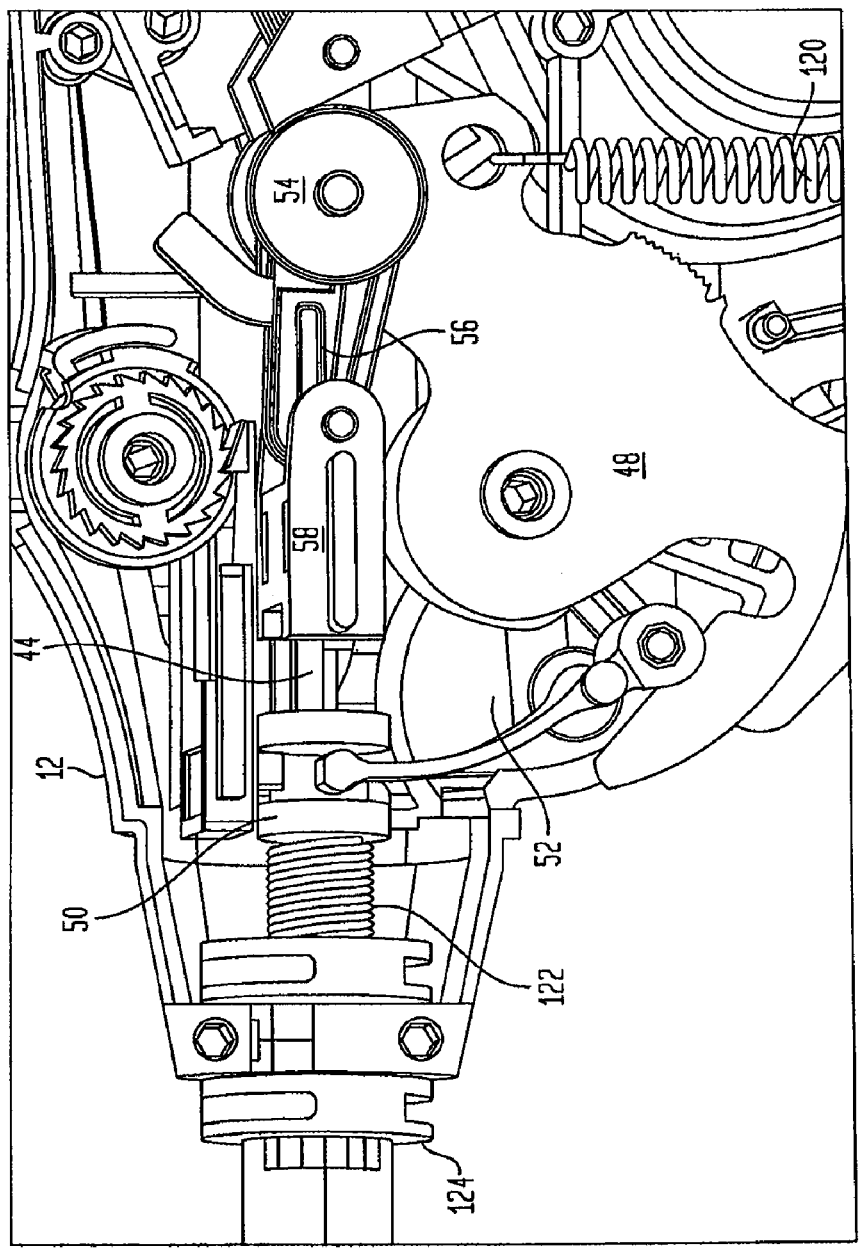
FIG. 17D is a side, partially cross-sectional view of a portion of the handle of the surgical clip applier shown in FIG. 17A, showing a clip forming assembly actuated.

As the trigger 16 is further actuated and the trigger insert 48 continues to pivot, the feed bar coupler 50 and feed bar 38 will eventually reach a distal-most position. In this position, the protrusion 86 on the feed bar 38 will be positioned at the distal end of the slot 88 in the jaw retainer shaft 28 and a clip will be positioned between the jaws 20, as previously discussed. Spring 122 will be fully compressed between the shaft coupler 124 and the feed bar coupler 50, and the feed link 52 will flex, as shown in FIGS. 17C and 17D. As the feed link 52 flexes, and more preferably once the feed link 52 fully flexed, the clip forming assembly will be actuated to close the jaws 20. The feed link 52 will remain flexed during actuation of the clip forming assembly, e.g., the second stage of actuation, such that the trigger insert 48 is pliant relative to the clip advancing assembly, and in particular the feed bar 38.

Figure 18:
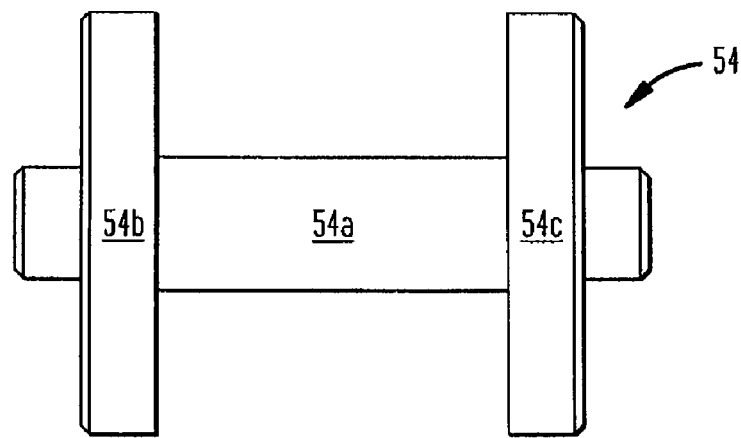
FIG. 18 is a side view of a closure link roller that forms part of a clip forming assembly of the surgical clip applier shown in FIG. 1A.
Figure 19:
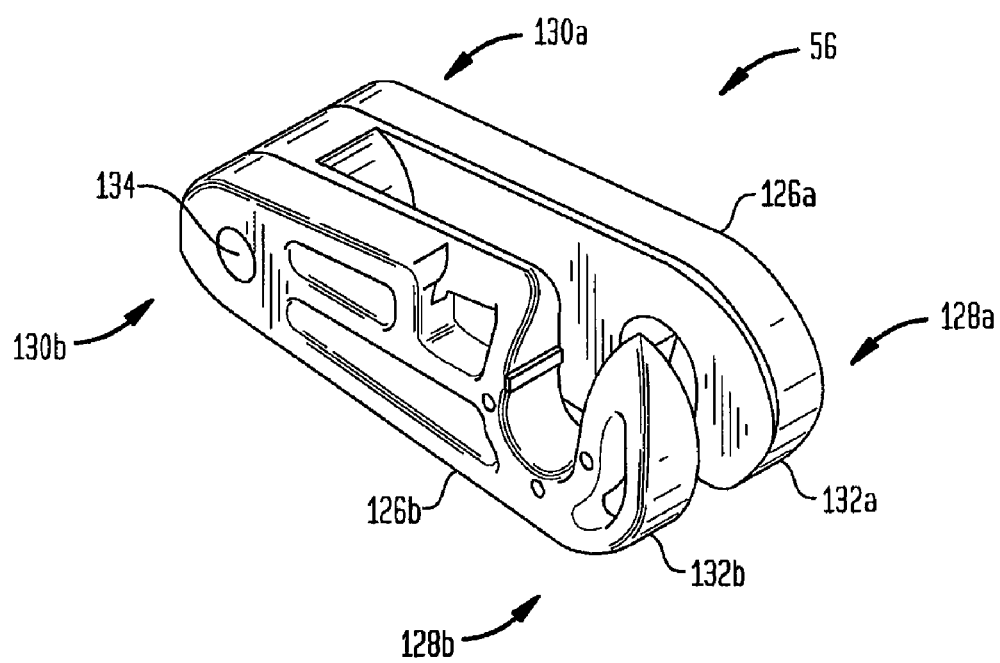
FIG. 19 is a top perspective view of a closure link that couples to the closure link roller shown in FIG. 18 to form part of a clip forming assembly of the surgical clip applier shown in FIG. 1A.

An exemplary clip forming assembly of the housing 12 is shown in more detail in FIGS. 18-20. In general, the clip forming assembly is disposed within the housing 12 and it is effective to move the push rod 44 and cam 42 relative to the jaws 20 to move the jaws 20 to a closed position and thereby crimp a clip positioned therebetween. While the clip forming assembly can have a variety of configurations, the illustrated exemplary clip forming assembly includes a closure link roller 54 that is slidably coupled to the trigger insert 48, a closure link 56 that is adapted to couple to the closure link roller 54, and a closure coupler 58 that is adapted to couple to the closure link 56 and to the push rod 44.

FIG. 18 illustrates the closure link roller 54 in more detail and, as shown, the closure link roller 54 includes a central shaft 54a having substantially circular flanges 54b, 54c formed adjacent to the opposed terminal ends thereof. The central shaft 54a can be adapted to sit within the second recess 110 in the trigger insert 48 such that the flanges 54b, 54c are received on opposed sides of the trigger insert 48. The central shaft 54a can also be adapted to mate to opposed arms 126a, 126b of the closure link 56 to position the arms on opposed sides of the trigger insert 48.

An exemplary embodiment of a closure link 56 is shown in more detail in FIG. 19, and as shown it has opposed arms 126a, 126b that are spaced a distance apart from one another. Each arm 126a, 126b includes a proximal end 128a, 128b that is adapted to engage the central shaft 54a of the closure link roller 54, and a distal end 130a, 130b that is adapted to mate to a closure coupler 58 for coupling the closure link roller 54 and closure link 56 to the push rod 44. In an exemplary embodiment, the proximal end 128a, 128b of each arm 126a, 126b is adapted to pivotally mate to the closure link roller 54, and thus the arms 126a, 126b can include, for example, hook-shaped members 132a, 132b formed thereon for engaging the central shaft 54a. The hook-shaped members 132a, 132b extend in opposite directions to facilitate engagement between the closure link 56 and the closure link roller 54. The distal end 130a, 130b of the arms 126a, 126b can be mated to one another, and they can include a lumen 134 extending therethrough for receiving a shaft that is adapted to pivotally mate the closure link 56 to the closure coupler 58. A person skilled in the art will appreciate that a variety of other techniques can be used to mate the closure link 56 to the closure link roller 54 and the closure coupler 58.

Figure 20A:
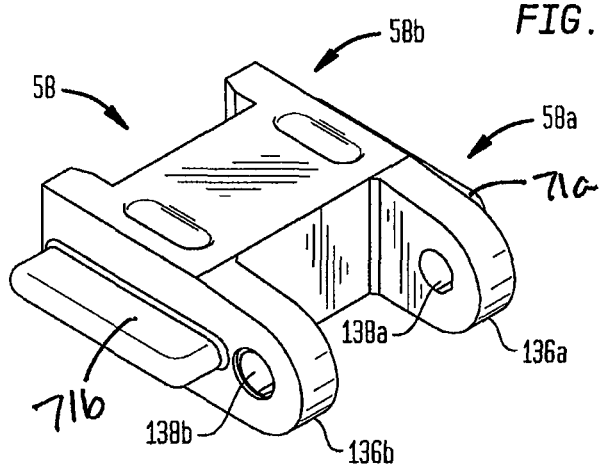
FIG. 20A is a top perspective view of a closure link coupler that couples to the closure link shown in FIG. 19 and that also forms part of the clip forming assembly of the surgical clip applier shown in FIG. 1A.
Figure 20B:
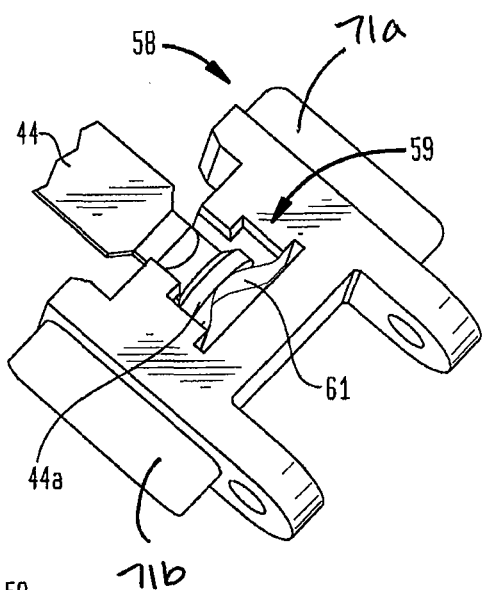
FIG. 20B is a bottom view of the closure link coupler shown in FIG. 20A coupled to the push rod of FIG. 9 and having one embodiment of a biasing element disposed therein.

An exemplary closure coupler 58 is shown in more detail in FIG. 20A, and as shown it includes a proximal portion 58a having two arms 136a, 136b with lumens 138a, 138b extending therethrough and adapted to be aligned with the lumen 134 in the closure link 56 for receiving a shaft to mate the two components. The closure coupler 58 can also include a distal portion 58b that is adapted to mate to the proximal end 44a of the push rod 44 (FIG. 9). In an exemplary embodiment, the closure coupler 58 includes a cut-out 59 (FIGS. 20B and 20C) formed therein and having a shape that is adapted to seat the proximal end 44a of the push rod 44. The distal portion 58b of the closure coupler 58 can also be configured to receive a portion of the feed bar coupler 50 when the trigger 16 is in the open position. A person skilled in the art will appreciate that a variety of other mating techniques can be used to mate the closure coupler 58 to the push rod 44, and that the closure coupler 58 and the push rod 44 can optionally be integrally formed with one another. The closure coupler 58 can further include side wings 71a, 71b. The wing 71a can be in contact with a compression spring 81, described in more detail below, to bias the closure coupler 58 proximally as the trigger 16 is squeezed.

In other exemplary embodiments, a preloaded joint can be formed between the push rod 44 and the closure coupler 58 to prevent accidental release of a clip from the jaws, particularly during the early stages of closure, if the user eases-up on the trigger 16. In particular, while the anti-backup mechanism, discussed in more detail below, can be adapted to prevent the trigger 16 from opening until the trigger 16 reaches a predetermined position, the anti-backup mechanism may allow some minor movement of the trigger 16. Thus, in the event a user eases-up on the trigger 16 and minor opening of the trigger 16 occurs, the preloaded joint will bias the push rod 44 in a distal direction, thereby maintaining the push rod 44 in a substantially fixed position, while allowing the closure coupler 58 to move proximally until the trigger 16 is engaged by the anti-backup mechanism.

Figure 20C:
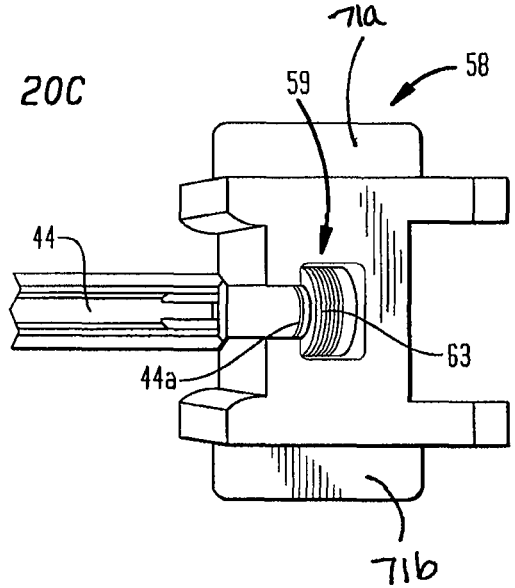
FIG. 20C is a bottom view of the closure link shown in FIG. 20A coupled to the push rod of FIG. 9 and having another embodiment of a biasing element disposed therein.

While the preloaded joint can have a variety of configurations, and it can be positioned at various locations along the clip forming assembly, in one exemplary embodiment the preloaded joint can be in the form of a biasing member disposed within the cut-out 59 to bias the push rod 44 in a distal direction. While a variety of biasing members can be used, in the embodiment shown in FIG. 20B, the biasing member is a cantilevered beam 61 that is positioned between the proximal end 44a of the push rod 44 and the back wall of the recess 59 to bias the push rod 44 distally. The cantilevered beam 61 can be formed from a shape memory material, such as Nitinol, that allows the beam 61 to flex or flatten when a proximally-directed force is applied thereto. The beam 61 can also be formed from a variety of other materials, such as spring steel or reinforced polymers, and more than one beam can be used. FIG. 20C illustrates another embodiment of a biasing member which is in the form of a coil or other type of spring 63. As shown, the spring 63 is disposed between the proximal end 44a of the push rod 44 and the back wall of the recess 59 to bias the push rod 44 distally. The spring 63 is adapted to compress when a proximally-directed force is applied thereto. A person skilled in the art will appreciate that a variety of other biasing members can be used, including elastomeric compression members.

The preloaded joint can also optionally include features to enhance performance of the cantilevered beam or spring during the clip forming process. In the embodiment shown in FIG. 20B, the load of the cantilevered beam 61 remains primarily uniform as the cantilevered beam is compressed during closure, however the load increases significantly during the final stages of closure. This is illustrated in FIG. 20D, which shows a graph of the load/displacement curve of the cantilevered beam 61 shown in FIG. 20B. The left end of the curve represents the unloaded height of the cantilevered beam 61, while the right end of the curve represents the point at which the cantilevered beam 61 is fully compressed or flattened. The upper curve represents the force resulting as the cantilevered beam 61 is compressed during a typical closing stroke, with the exception that the force is measured from a free state of the cantilevered beam 61 whereas the cantilevered beam 61 is initially partially compressed when it is disposed within the closure coupler 58. As shown, the load remains substantially constant (excluding the initial compression stages), increasing only slightly during the closing stroke as the cantilevered beam 61 is being compressed. However, the load increases significantly at the final stages of closure when the cantilevered beam 61 is fully flattened. This is due to deflection of the cantilevered beam 61 which causes the load to be transferred from the terminal ends of the cantilevered beam 61 inward. As the cantilevered beam 61 deflects and the load is transferred inward, the effective length of the cantilevered beam 61 is decreased, thereby increasing the load. In order to prevent this, the preloaded joint can optionally include features to enhance the cantilevered beam or spring performance, and in particular to maintain a substantially constant load during clip formation.

Figure 20E:
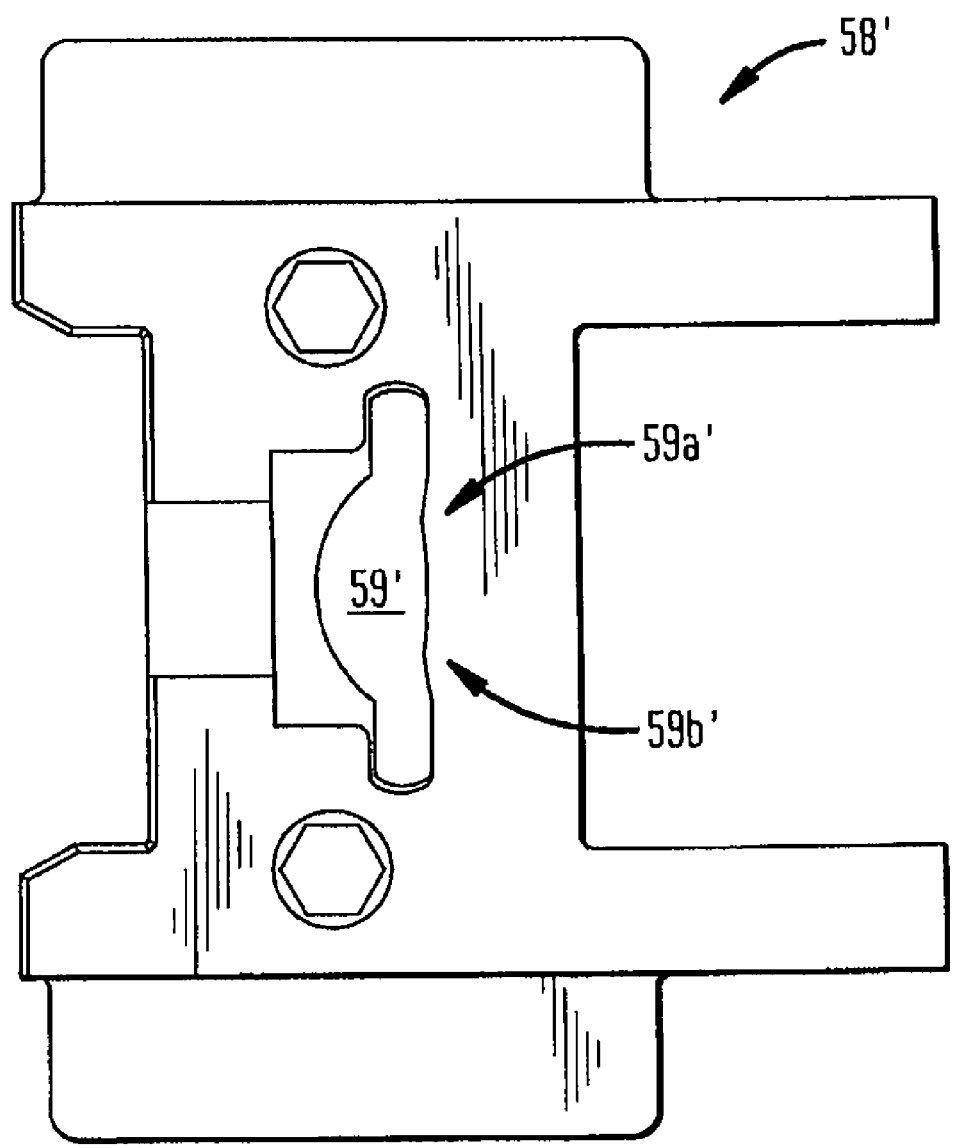
FIG. 20E is a side view of another embodiment of a portion of a closure link coupler having ridges formed therein.

FIG. 20E illustrates one exemplary embodiment of a technique for enhancing the cantilevered beam or spring performance. As shown, the recess 59' in the closure coupler 58' includes two ridges 59a', 59b' formed therein on the back surface thereof such that the ridges 59a', 59b' are positioned underneath or behind the cantilevered beam (not shown). The ridges 59a', 59b' are spaced a distance apart from one another and each ridge 59a', 59b' has a height of at least about 0.005" to prevent the cantilevered beam from fully flattening against the back surface of the recess. As a result, the ridges 59a', 59b' will prevent the cantilevered beam from deflecting, thereby preventing the load of the spring or cantilevered beam from transferring from the terminal ends inward. A person skilled in the art will appreciate that the particular location, quantity, and size of the ridges 59a', 59b' can vary depending on the configuration of the preloaded joint, as well as the forces necessary to prevent clip fallout during closure.

In use, referring back to FIGS. 17A-17D, as the trigger 16 is initially moved from the open position toward the closed position, the closure link roller 54 will roll within the recess 110 in the trigger insert 48. Once the feed bar 38 and feed bar coupler 50 are in the distal-most position, as shown in FIG. 17C, further actuation of the trigger 16 will cause the recess 110 in the trigger insert 48 to engage the closure link roller 54 forcing it to pivot with the trigger insert 48, as shown in FIG. 17D. As a result, the closure coupler 58 will move distally, thereby causing the push rod 44 to move distally. As the push rod 44 advances distally, the cam 42 is advanced over the jaws 20 to close the jaws 20 and crimp the clip positioned therebetween. The trigger 16 can optionally be partially closed to only partially close the jaws 20 and thus partially crimp a clip disposed therebetween. Exemplary techniques for facilitating selective full and partial closure of the clip will be discussed in more detail below. Once the clip is applied, the trigger 16 can be released thereby allowing spring 120 to pull the trigger insert 48 back to its initial position, and allowing spring 122 to force the feed bar coupler 50 and feed bar 38 back to the proximal position. As the trigger insert 48 returns to its initial position, the closure link roller 54 is moved back to its initial position as well, thereby pulling the closure link 56, closure coupler 58, and push bar 44 proximally.

The surgical clip applier 10 can also include a variety of other features to facilitate use of the device 10. In one exemplary embodiment, the surgical clip applier 10 can include an anti-backup mechanism for controlling movement of the trigger 16. In particular, the anti-backup mechanism can prevent the trigger 16 from opening during a partial closing stroke. However, once the trigger reaches a predetermined position, at which point the clip positioned between the jaws can be partially crimped, the anti-backup mechanism can release the trigger allowing the trigger to open and release the clip or to close to fully crimp the clip, as may be desired by the user.

Figure 21A:
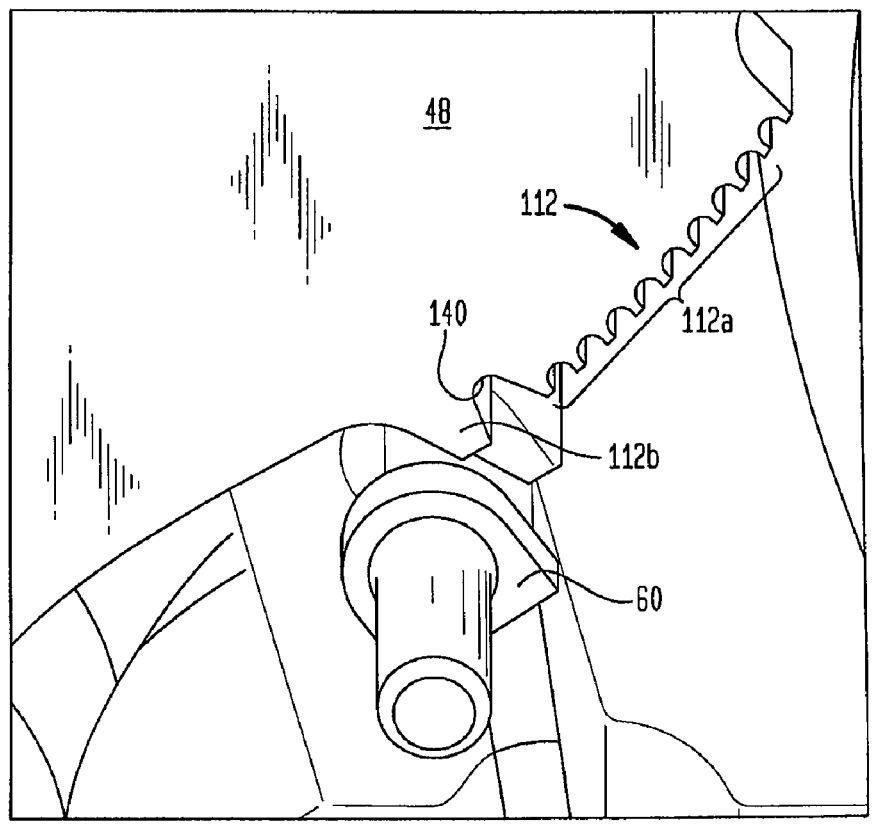
FIG. 21A is an enlarged side perspective view of an anti-backup mechanism of the surgical clip applier shown in FIG. 1A.
Figure 21B:
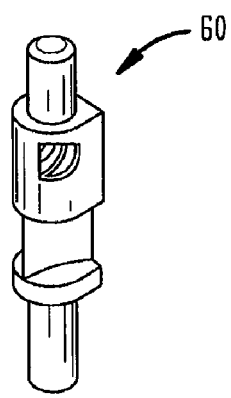
FIG. 21B is a perspective view of a pawl mechanism of the anti-backup mechanism shown in FIG. 21A.

FIGS. 21A and 21B illustrate one exemplary embodiment of an anti-backup mechanism in the form of a ratchet. As shown, the ratchet includes a set of teeth 112 formed on the trigger insert 48, and a pawl 60 that is adapted to be rotatably disposed within the housing 12 and positioned adjacent to the trigger insert 48 such that closure of the trigger 16 and pivotal movement of the trigger insert 48 will cause the pawl 60 to engage the teeth 112. The teeth 112 can be configured to prevent rotation of the pawl 60 until the pawl 60 reaches a predetermined position, at which point the pawl 60 is free to rotate, thereby allowing the trigger 16 to open or close. The predetermined position preferably corresponds to a position at which the jaws 20 are partially closed. In an exemplary embodiment, as shown, the teeth 112 include a first set of teeth 112a, e.g., ten teeth, having a size that prevents rotation of the pawl 60 relative thereto, thus preventing the trigger 16 from opening when the pawl 60 is engaged with the first set 112a of teeth 112. The teeth 112 can also include a final or terminal tooth, referred to as a tock tooth 112b, that has a size that allows the pawl 60 to rotate relative thereto when the pawl 60 is engaged with the tock tooth 112b. In particular, the tock tooth 112b preferably has a size that is substantially greater than the size of the first set of teeth 112a such that a relatively large notch 140 is formed between the first set of teeth 112a and the tock tooth 112b. The notch 140 has a size that allows the pawl 60 to pivot therein, thus allowing the pawl 60 to be selectively moved beyond the tock tooth 112b or back toward the first set of teeth 112a. A person skilled in the art will appreciate that the tock tooth 112b can have the same size or a smaller size than the first ten teeth 112a while still providing a notch 140 formed therebetween that allows the pawl 60 to pivot therein.

Figure 22A:
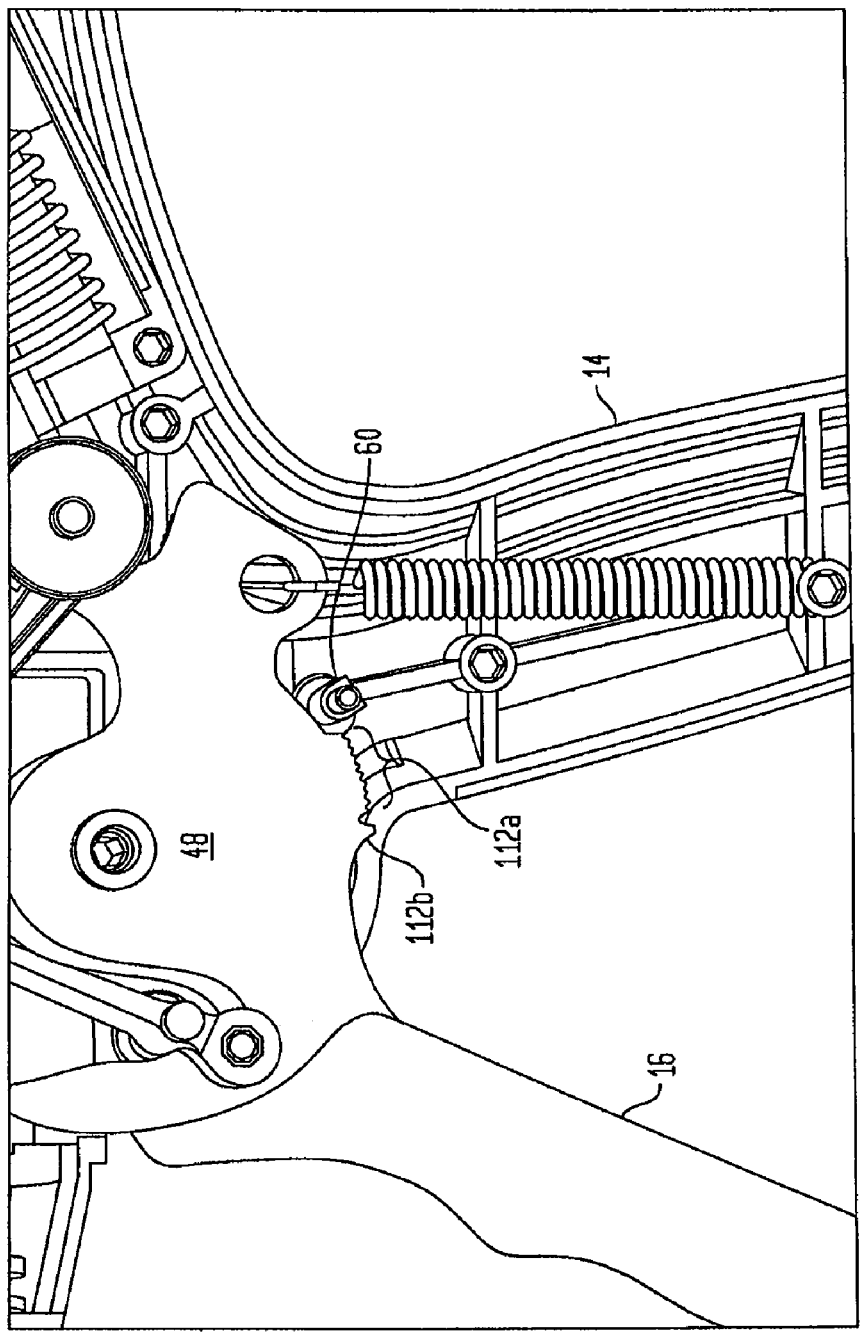
FIG. 22A is a side, partially cross-sectional view of a portion of the handle of the surgical clip applier shown in FIG. 1A, showing the anti-backup mechanism in an initial position.
Figure 22B:
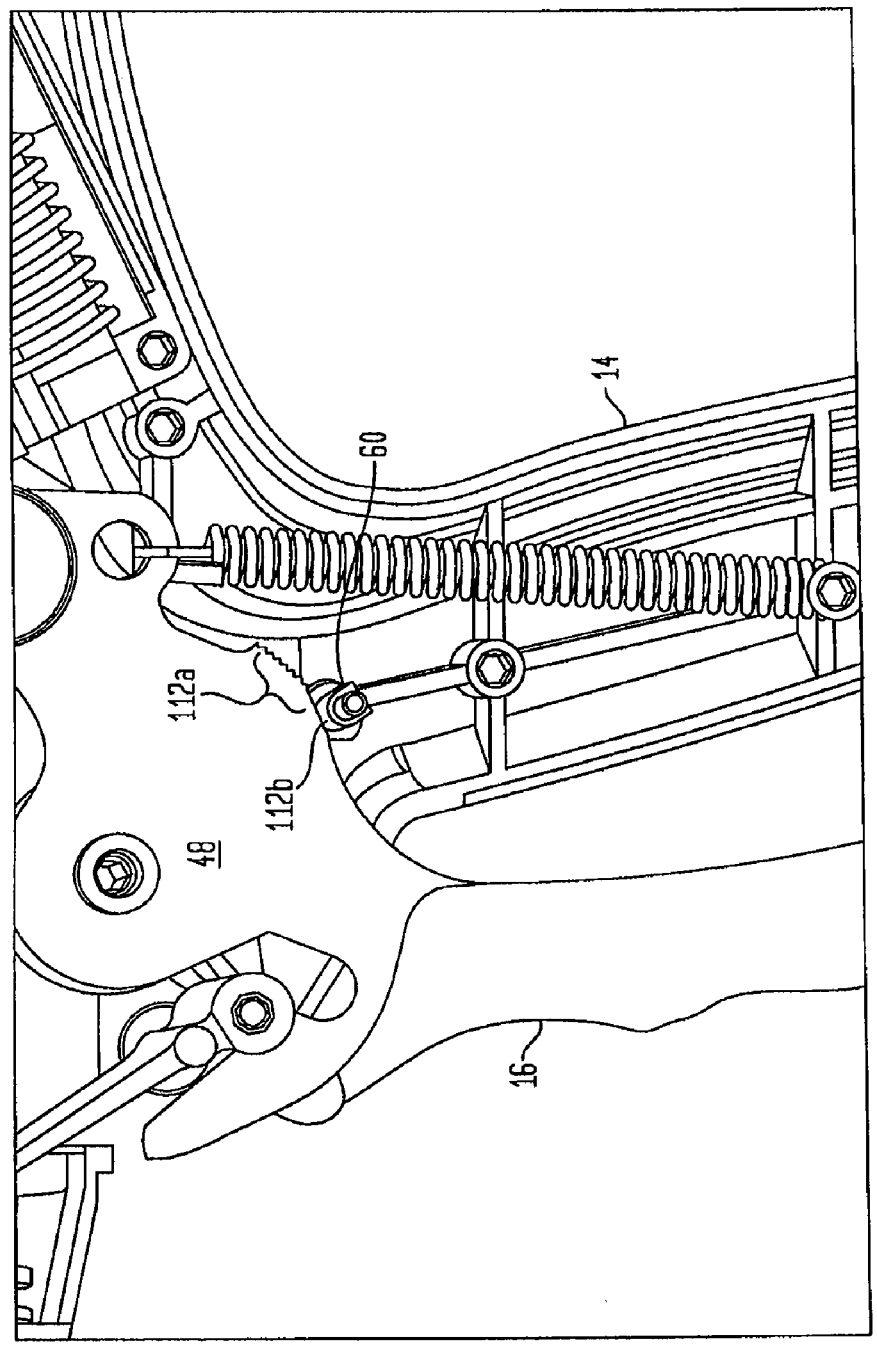
FIG. 22B is a side, partially cross-sectional view of a portion of the handle of the surgical clip applier shown in FIG. 22A, showing the anti-backup mechanism in a partially actuated position.
Figure 22C:
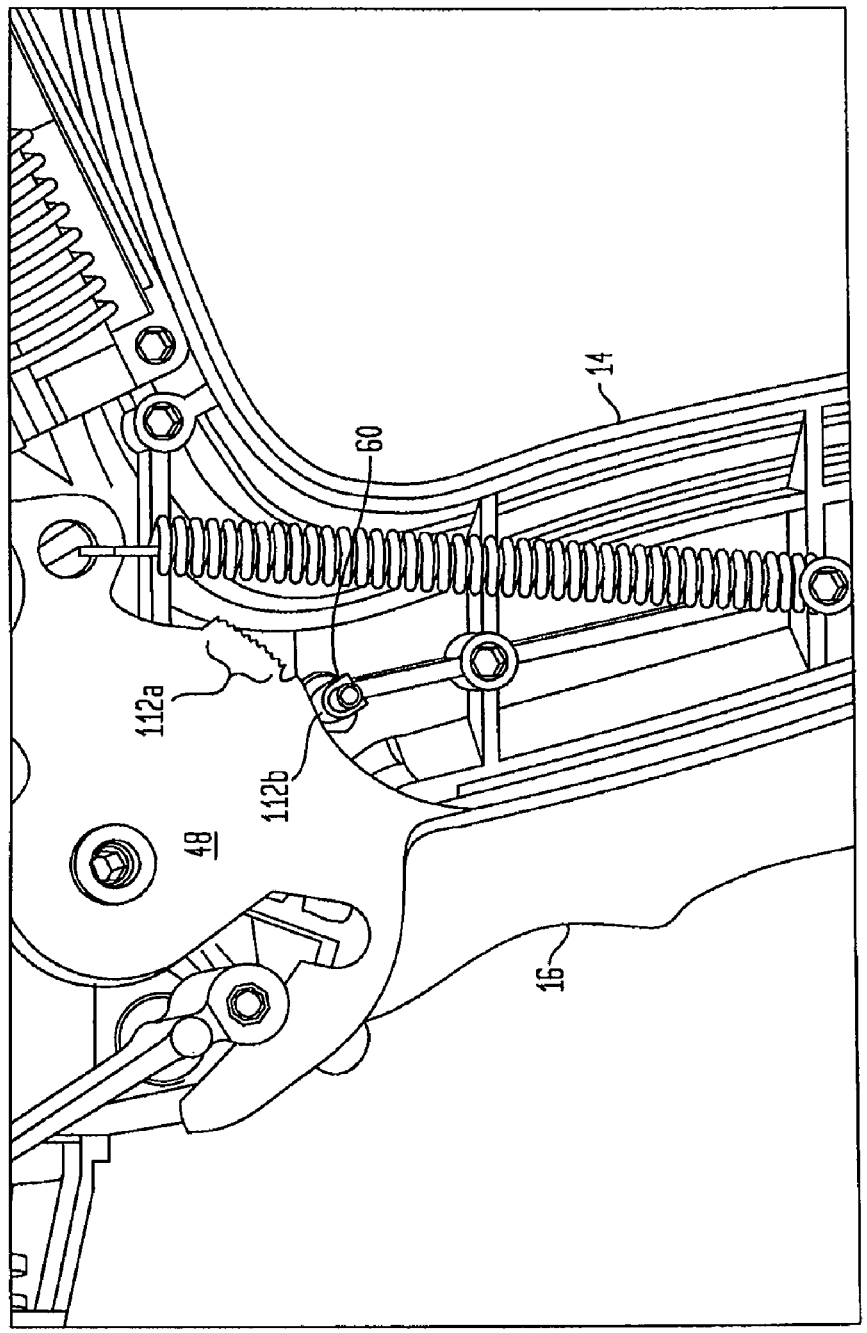
FIG. 22C is a side, partially cross-sectional view of a portion of the handle of the surgical clip applier shown in FIG. 22B, showing the anti-backup mechanism in a fully actuated position.
Figure 22D:
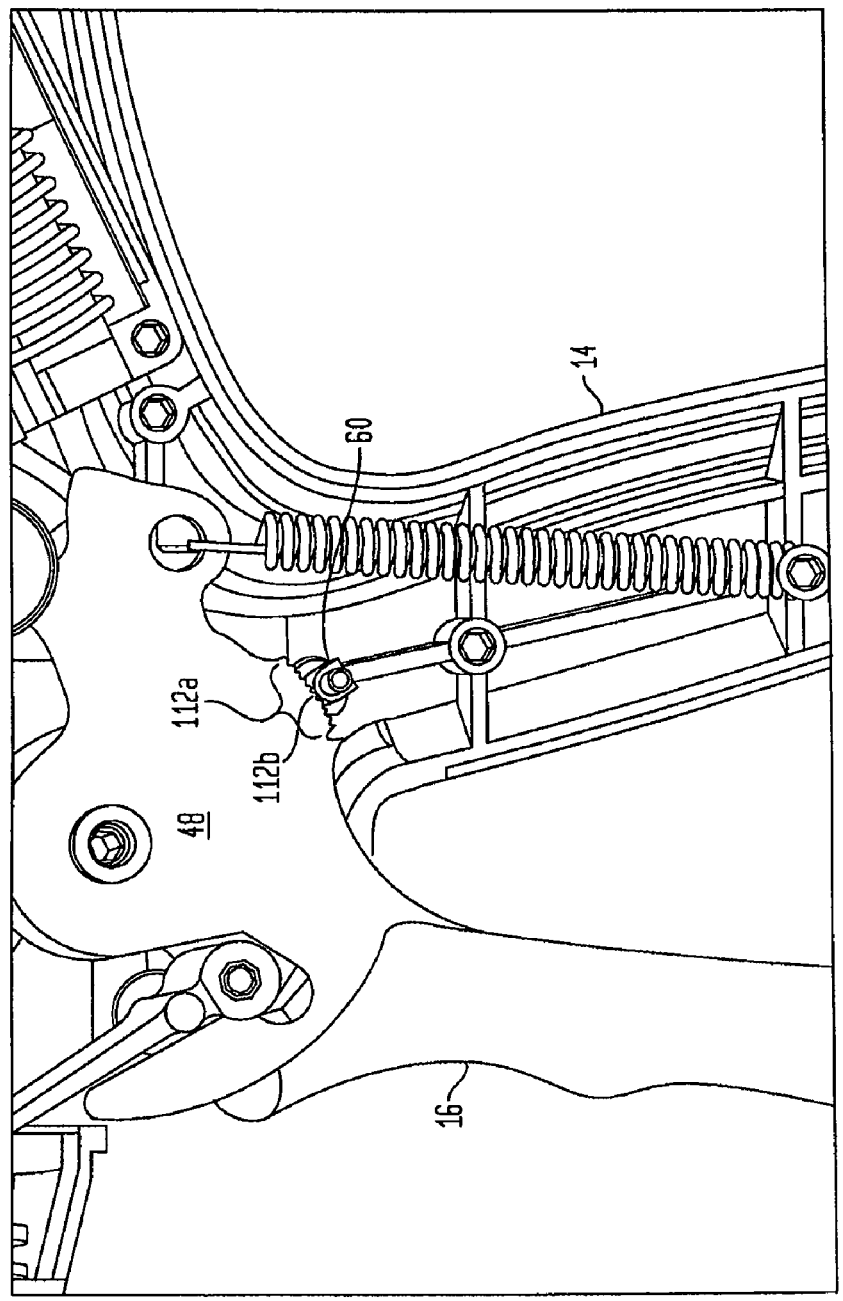
FIG. 22D is a side, partially cross-sectional view of a portion of the handle of the surgical clip applier shown in FIG. 22C, showing the anti-backup mechanism returning to an initial position.
Figure 22E:
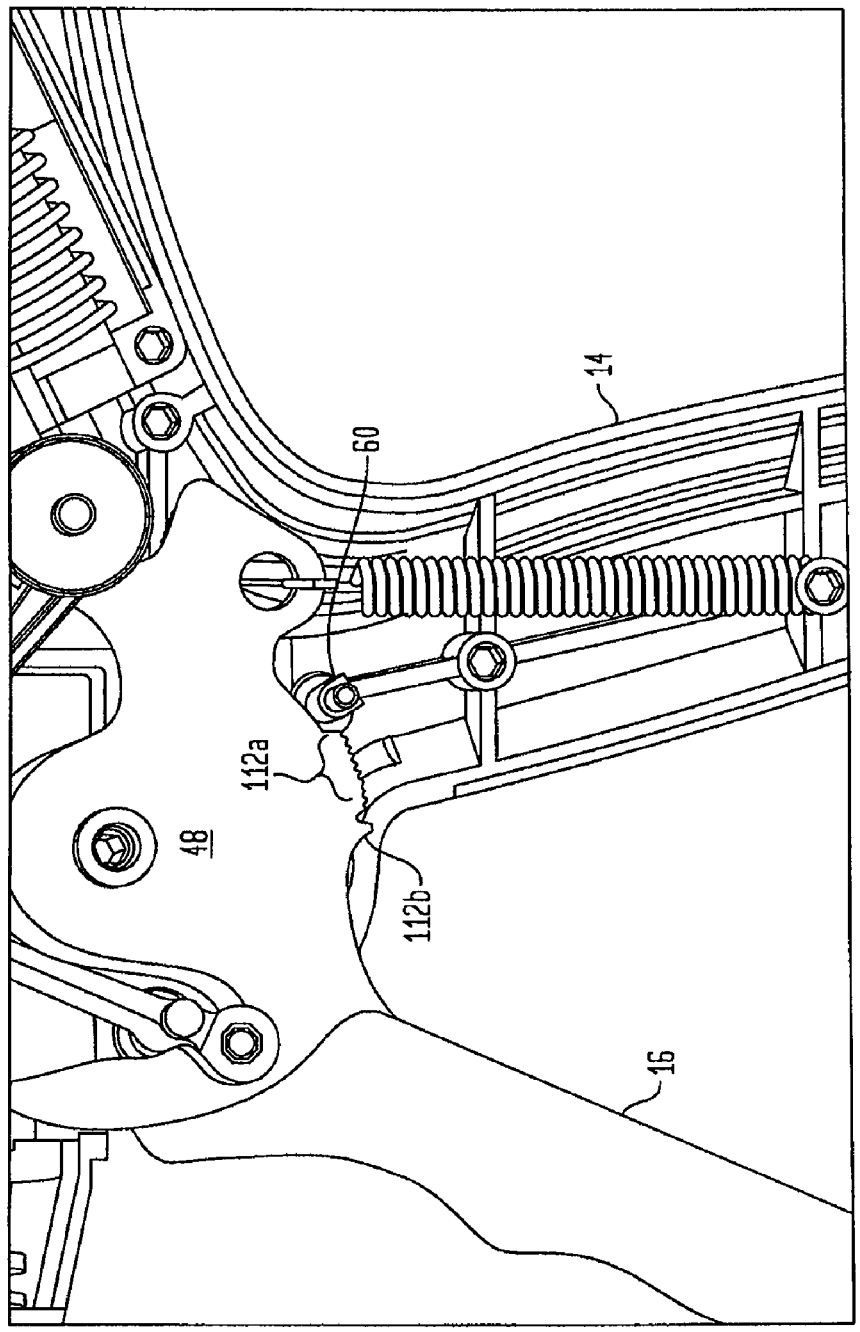
FIG. 22E is a side, partially cross-sectional view of a portion of the handle of the surgical clip applier shown in FIG. 22D, showing the anti-backup mechanism returned to the initial position.

FIGS. 22A-22D illustrates the ratchet mechanism in use. When the trigger 16 is initially moved toward a closed position, as shown in FIG. 22A, the pawl 60 will engage the first set of teeth 112a thereby preventing the trigger 16 from opening. Further actuation of the trigger 16 will cause the pawl 60 to advance past the first set of teeth 112a until the pawl 60 reaches the notch 140 next to the tock tooth 112b. Once the pawl 60 reaches the tock tooth 112b, at which point the jaws 20 are partially closed due the partial distal movement of the cam 42 over the jaws 20, the pawl 60 is free to rotate thereby allowing the trigger 16 to open or close, as may be desired by the user. FIG. 22C illustrates the trigger 16 in a fully closed position, and FIGS. 22D and 22E illustrate the trigger 16 returning to the open position.

As previously explained herein, in other embodiments the clip applier can include a stop mechanism for indicating to a user when the clip supply is depleted. In an exemplary embodiment, the stop mechanism can be operatively associated with the ratchet mechanism to aid in maintaining the trigger in a fixed, partially opened position after the last clip is applied. In particular, the stop mechanism can be configured to activate when the pawl 60 is engaged with the teeth 112a, and prior to the pawl 60 reaching the notch during the opening stroke. In this position, the pawl 60 is unable to rotate in either direction, thus preventing the trigger 16 from moving, and thereby providing feedback to a user through the trigger 16 that the clip supply is depleted. As previously described, in one embodiment the stop mechanism can be in the form of a tang 82d' formed on the feeder shoe 34''', and recesses 51a, 51b formed in the advancer 40'' and feed bar 38''. After the proximal-most clip is formed, the trigger 16 can be released to move from the fully closed position toward the open position, thereby causing the feed bar 38' and the advancer 40'' to retract proximally. Proximal movement of the feed bar 38'' will cause the pawl 60 to re-engage the teeth 122b, 112a. With the pawl 60 in engagement with the teeth 112a, and before the pawl 60 reaches the notch 140, the recesses 51a, 51b formed in the advancer 40'' and the feed bar 38' will engage with the tang 82d' on the feeder shoe 34''' to prevent further proximal movement of the feed bar 38' and the advancer 40'. The fixed or locked position of the feed bar 38' and the advancer 40'' thus prevents the pawl 60 from reaching the notch 140. As a result, the pawl 60 cannot rotate and thus the trigger 16 is prevented from opening or closing, and is thereby locked in a fixed, partially closed position preventing further use of the device.

Figure 22F:
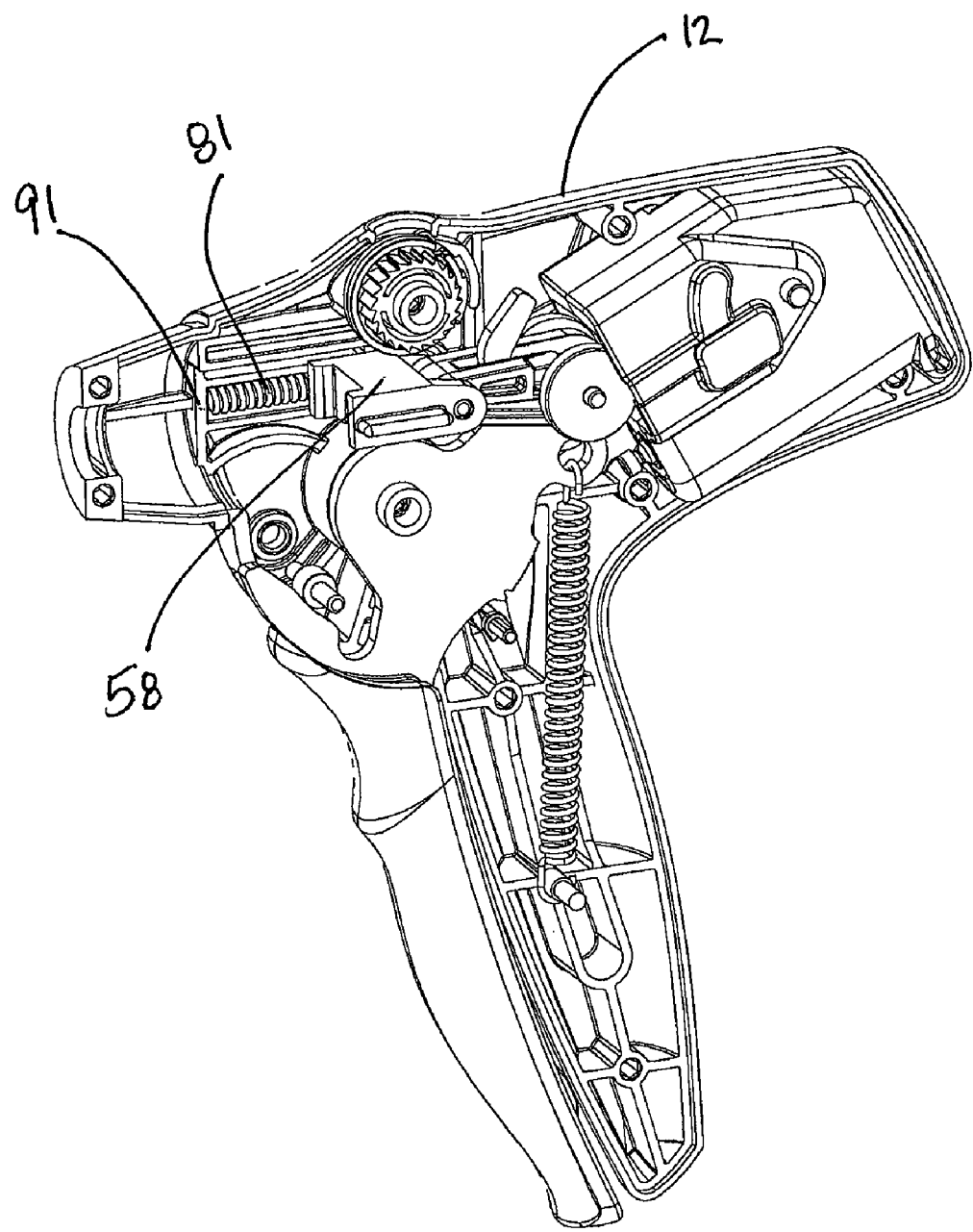
FIG. 22F is a perspective view of one embodiment of a compression spring for biasing the closure link coupler of FIG. 20A.
Figure 22G:
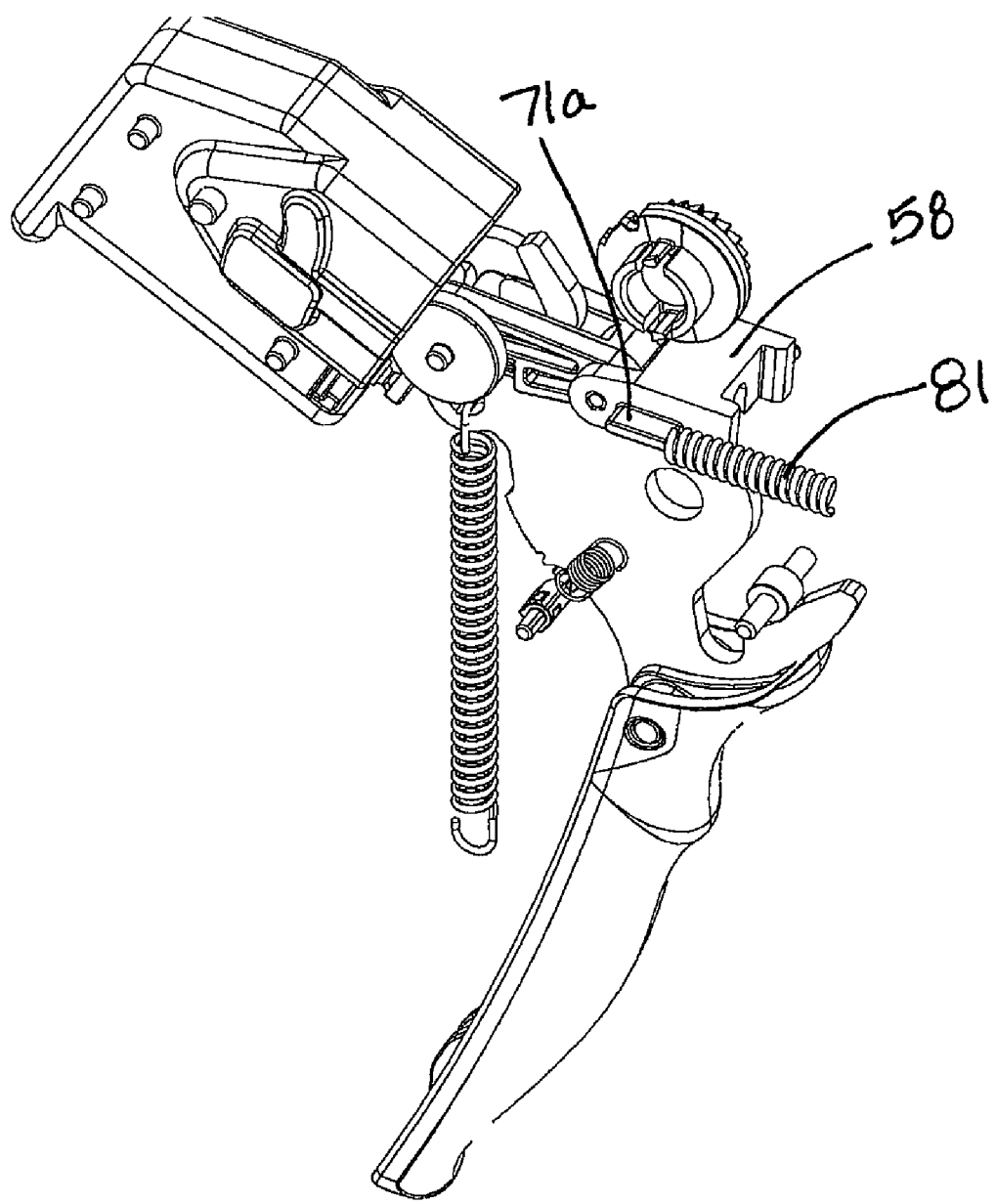
FIG. 22G is a perspective view of the compression spring of FIG. 22F.

While the trigger 16 is locked in a partially opened position after the last clip is applied, the jaws 20 should fully open to allow the clip to be released. This can be achieved by adding a biasing element, such as a compression spring 81 as shown in FIGS. 22F and 22G, that biases the push rod 44 to the proximal position. The spring 81 can be disposed anywhere within the housing 12, but in the illustrated embodiment, the spring 81 is disposed between a wall 91 of the housing 12 and a wing 71*a* formed on the closure coupler 58. A distal end of the spring 81 can abut up against the wall 91 of the housing 12, and a proximal end of the spring 81 can abut against the wing 71*a* of the closure coupler 58 to bias the closure coupler 58 in a proximal direction, which in turn biases a proximal end 44*a* of the push rod 44 in a proximal direction. Thus, when the trigger 16 is fully closed, the spring 81 is compressed between the wall 91 of the housing 12 and the wing 71*a*, biasing the closure coupler 58, and hence the push rod 44, proximally. The trigger 16, however, prevents any proximal movement of the closure coupler 58 and the push rod 44. As the trigger 16 is partially released from its fully closed position, the spring 81 will move the closure coupler 58, and thus the push rod 44, proximally to allow the jaws 20 to open and release the clip. The jaws 20 will thus open before the trigger 16 is fully opened and, in particular, before the trigger 16 is locked by the lockout mechanism.

The ratchet mechanism can also be configured to emit an audible sound that indicates the position of the jaws 20. For example, a first sound can be emitted when the pawl 60 engages the first set of teeth 112*a*, and a second, different sound, e.g., a louder sound, can be emitted when the pawl 60 engages the tock tooth 112*b*. As a result, when the trigger 16 reaches the predetermined position at which the pawl 60 is engaged with the tock tooth 112*b*, the sound indicates to the user that the jaws 20 are in the partially closed position. The user can thus release the trigger 16 to release a partially closed clip, or they can fully close the trigger 16 to fully close the clip.

In another exemplary embodiment, the surgical clip applier 10 can include an overload mechanism that is adapted to prevent overload of a force applied to the jaws 20 by the trigger 16. Typically, during application of a surgical clip, a certain force is required to close the jaws 20 and crimp the clip around the tissue positioned therebetween. As the forming process proceeds and the clip is at least partially closed, the force required to continue closing the jaws 20 around the clip significantly increases. Accordingly, in an exemplary embodiment, the overload mechanism can have a resistance that correlates to the force required to close the jaws 20. In other words, the resistance of the overload mechanism can increase as the force required to close the jaws 20 increases. The resistance is, however, preferably slightly greater than the force required to close the jaws 20 to prevent accidental actuation of the overload mechanism. As a result, if the jaws 20 are prevented from closing when the trigger 16 is initially actuated, the force required to overcome the resistance of the overload mechanism is relatively low. This is particularly advantageous as the jaws 20 are more susceptible to being deformed when they are open or only partially closed. The overload mechanism will actuate more readily in the early stages of clip formation to prevent deformation of the jaws. Conversely, when the jaws 20 are substantially closed, the resistance is relatively high such that the overload mechanism can only be actuated upon application of a significant force applied to the jaws 20.

Figure 23A:
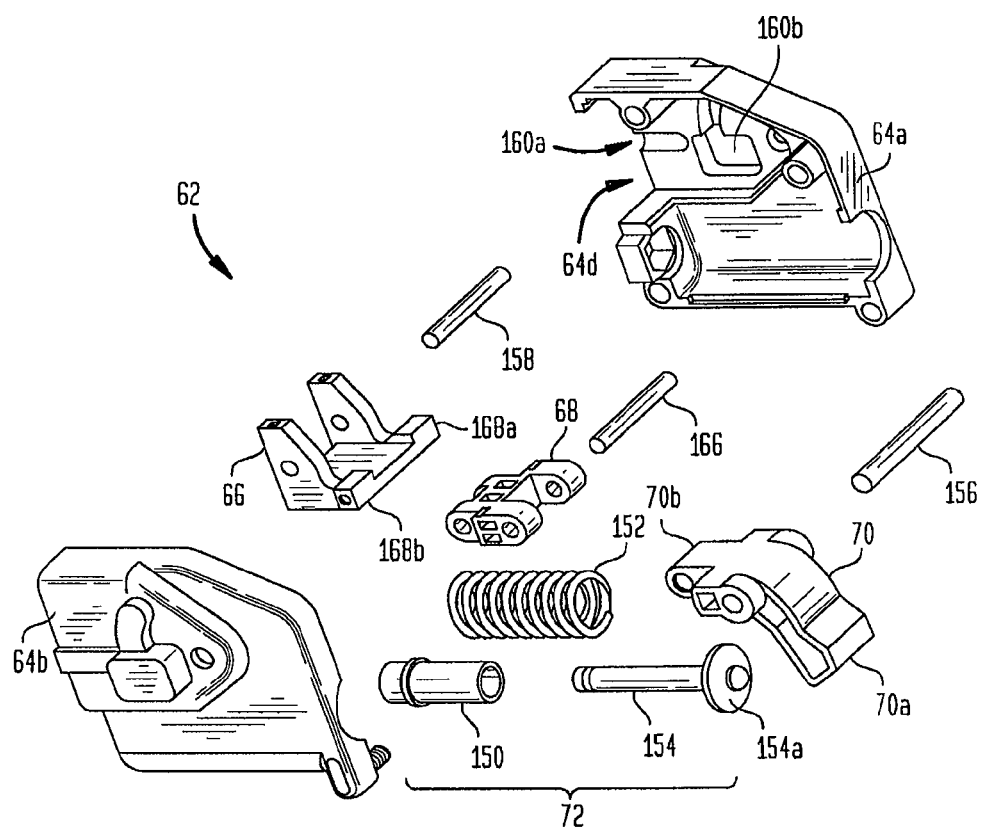
FIG. 23A is an exploded view of an overload mechanism of the surgical clip applier shown in FIG. 1A.

FIG. 23A illustrates one exemplary embodiment of an overload mechanism 62, showing an exploded view. In general, the overload mechanism can include an overload housing 64 formed from two halves 64*a*, 64*b* and containing a profile link 66, a toggle link 68, a pivot link 70, and a biasing assembly 72. The biasing assembly 72 can include a spring post 150 that is coupled to the housing 64 and that includes a bore extending therethrough for receiving a plunger 154. A spring 152 is disposed around the spring post 150, and the plunger 154 extends through the spring post 150 and includes a head 154*a* formed thereon that is adapted to abut against the spring 152. The pivot link 70 can be generally L-shaped and it can be coupled to the housing 64 by a pivot pin 156 extending therethrough. A proximal end 70*a* of the pivot link 70 can contact the head 154*a* of the plunger 154, and a distal end 70*b* of the pivot link 70 can be pivotally coupled to the toggle link 68 by a pivot pin 166. The toggle link 68, in turn, can be coupled to the profile link 66, which can be slidably and pivotally positioned within the housing 64 adjacent to an opening 64*d* formed in the housing. Pivotal movement of the profile link 66 within the housing 64 can be achieved by, for example, a pivot pin 158 that extends through the profile link 66 and is that disposed within a first slot 160*a* (only one slot is shown) formed in each half 64*a*, 64*b* of the housing 64, and slidable movement of the profile link 66 within the housing 64 can be achieved by, for example, opposed protrusions 168*a*, 168*b* formed on the profile link 66 that are received within a second slot 160*b* (only one slot is shown) formed in each half 64*a*, 64*b* of the housing 64.

In use, the profile link 66 can be adapted to receive a force from the clip forming assembly and to counter the force with the resistance of the biasing assembly 72. In particular, the overload mechanism 62 uses the spring 152 along with the toggle link 68 and pivot link 70 to bias the profile link 66 from either rotating about the pivot pin 158 or sliding against the housing 64. For the rotational aspect, the force exerted by the compressed spring 152 is transferred through the toggle link 68 and pivot link 70, such that a rotational moment is applied to the profile link 66 against the housing 64. Thus this assembly causes the profile link 66 to resist rotation with respect to the housing 64. If the moment generated by a radial load from the closure link roller 54 against the profile link 66 exceeds the moment of the pivot link 70 and toggle link 68, the profile link 66 begins to rotate, buckling the toggle link 68 and causing the pivot link 70 to further compress the spring 152. For the sliding aspect, the pivot link 70, toggle link 68, and profile link 66 are aligned such that the sliding force (resistance to slide) is the force required to buckle the toggle link 68 and pivot link 70. If the radial load from the closure link roller 54 against the profile link 66 exceeds the buckling force of the linkages, then the pivot link 70 further compresses the spring 152 as the profile link 66 slides proximally.

Figure 23B:
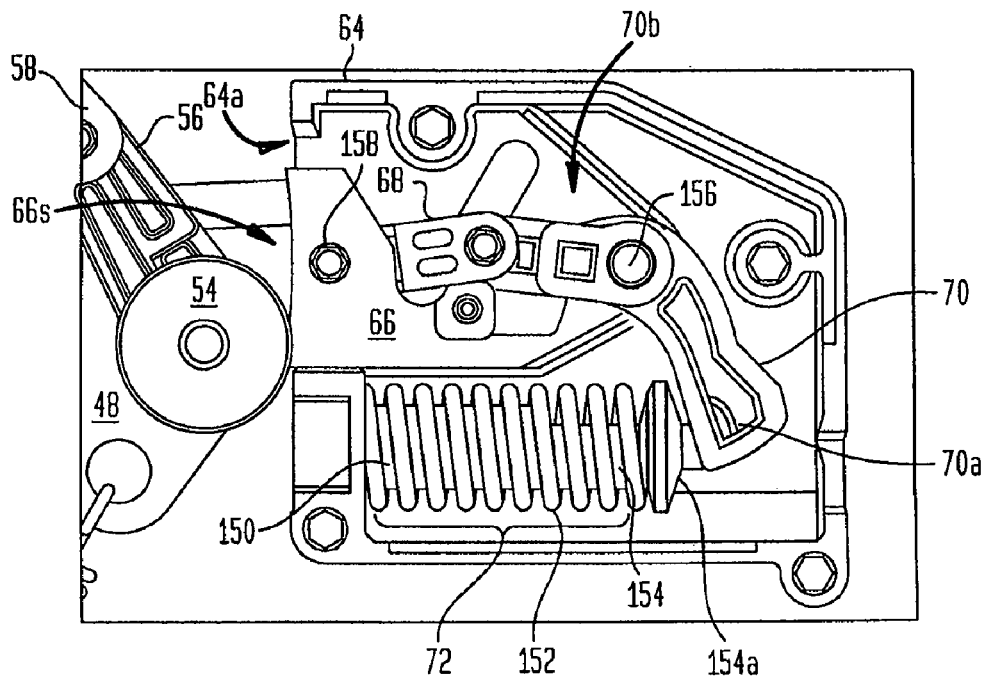
FIG. 23B is a partially cross-sectional view of the overload mechanism shown in FIG. 23A, showing the closure link roller first coming into contact with the profile link.
Figure 23C:
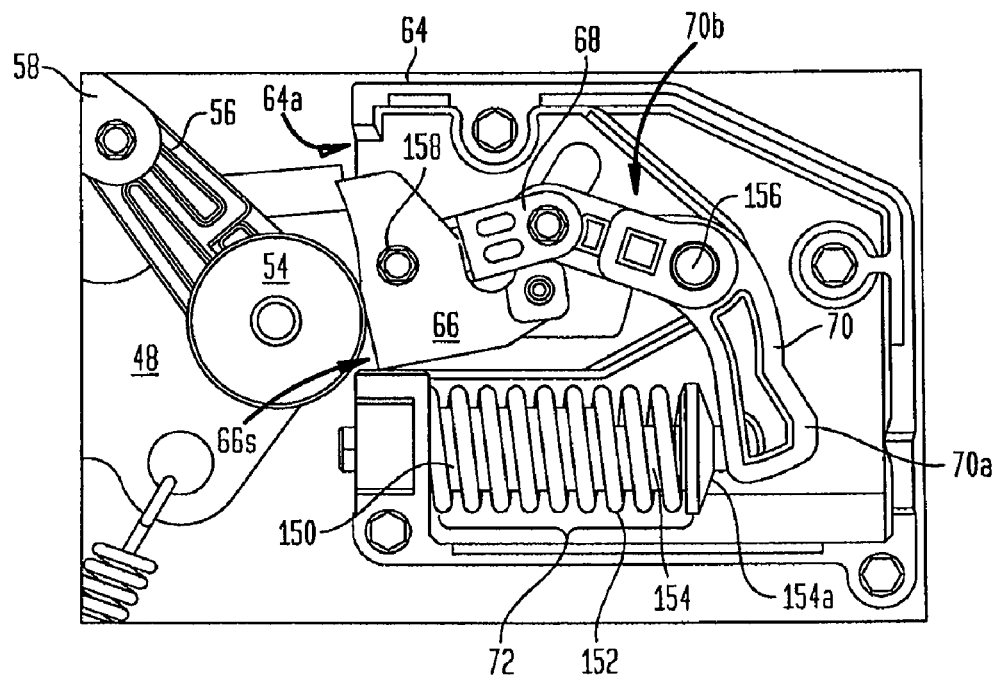
FIG. 23C is a partially cross-sectional view of the overload mechanism shown in FIG. 23B, showing the closure link roller applying a force to the profile link causing the profile link to pivot.

This is shown in more detail in FIGS. 23B-23C, and as shown the opening 64*d* in the housing 64 allows the closure link roller 54 of the clip forming assembly to roll against the profile link 66. As a result, when the trigger 16 is actuated and moved toward the closed position, the closure link roller 54 applies a force to the profile link 66. The resistance of the overload spring 152 will, however, maintain the profile link 66 in a substantially fixed position unless the force applied by the closure link roller 54 increases to a force that is greater than the resistance, e.g., a threshold force. This can be caused by, for example, a foreign object positioned between the jaws 20 or when the jaws 20 are fully closed with the clip and vessel, duct, shunt, etc. therebetween. When the jaws 20 cannot be further closed, the force applied to the closure link roller 54 from the closing motion of the trigger 16 will be transferred to the profile link 66, which will then pivot and slide within the housing 64, thereby causing the pivot link 70 to pivot, which forces the plunger 154 to compress the overload spring 152.

As previously noted, the force required to actuate the overload mechanism can correlate to the force required to close the jaws 20, which increases as the trigger 16 is moved to the closed position. This can be achieved due to the configuration of the profile link 66. In particular, when the closure link roller 54 first comes into contact with the profile link 66 and is thus in a lower position, the profile link 66 can pivot within the housing 64, as shown in FIG. 23B. As the closure link roller 54 moves upward along the profile link 66, the force required to overcome the resistance of the overload mechanism increases because the profile link 66 must slide within the housing 64, as shown in FIG. 23C. The force required to pivot the profile link 66 can be less than the force required to slide the profile link 66. Accordingly, if the jaws 20 are prevented from being closed, e.g., by a foreign object, as the trigger is initially actuated, a minimal force will be required to cause the closure link roller 54 to transfer the force to the lower portion of the profile link 66 causing the profile link 66 to pivot. When the jaws 20 are substantially closed and the trigger 16 is almost fully actuated, a significant amount of force is required to cause the closure link roller 54 to transfer the force to the upper portion of the profile link 66 causing the profile link 66 to slide within the housing 64 to overcome the resistance of the overload spring 152. While the amount of force required to actuate the overload mechanism can be greater than and can increase relative to the amount of force required to close the jaws 20, the force is preferably only slightly greater than the force required to close the jaws 20 to prevent deformation or other damage to the jaws 20. A person skilled in the art will appreciate that the resistance can be adjusted based on the force necessary to close the jaws 20.

The profile link 66, and in particular the distal-facing surface 66s of the profile link 66, can also have a shape that facilitates correlation between the force required to actuate the overload mechanism and the force required to close the jaws 20. For example, where the force required to close the jaws 20 increases at a linear rate, the distal-facing surface 66s of the profile link 66 can be planar to prevent the profile link 66 from interfering with movement of the closure link roller 54 there over, and to allow a linear force to be applied to the trigger 16 to close the jaws 20. Conversely, where the force required to close the jaws 20 is non-linear as the trigger 16 is moved to the closed position, the profile link 66 can have a non-linear shape that corresponds to the non-linear force. Such a configuration will prevent the forces required to close the cam 42 (FIG. 8) from becoming too high.

By way of non-limiting example, the force required to close the jaws 20 can be non-linear due to the shape of the recess 104 in the cam 42 that is adapted to push the jaw members 96a, 96b toward one another. As shown in FIG. 8, the recess 104 can have a curved configuration such that the force will vary as the cam 42 passes over the jaw members 96a, 96b. The profile link 66 can therefore having a corresponding curved distal-facing surface such that the force will also vary as the closure link roller 54 passes there over. As shown in FIGS. 23A and 23B, the profile link 66 is curved such that the lower portion of the profile link 66 is substantially convex and the upper portion of the profile link 66 is substantially concave. A person skilled in the art will appreciate that the profile link 66 can have a variety of other shapes, and that a variety of other techniques can be used to optimize the force necessary to close the jaws 20 and the force necessary to actuate the overload mechanism.

Figure 23D:
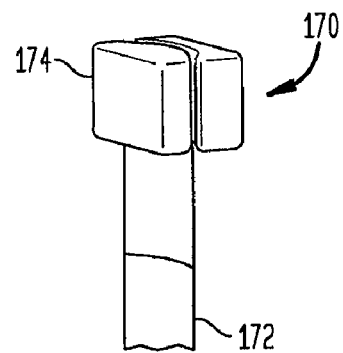
FIG. 23D is a perspective view of another embodiment of an overload mechanism for use with a surgical clip applier.

A person skilled in the art will also appreciate that the overload mechanism can have a variety of other configurations. By way of non-limiting example, FIG. 23D illustrates an overload mechanism that is in the form of a cantilevered beam 170 for receiving a force applied by the closure link roller 54. The beam 170 can have a substantially curved member 172 with a bracket 174 coupled to one end thereof. The curved member 172 can have a bending moment that, when loaded with a force greater then the bending moment, buckles to assume a low rigidity condition. The bracket 174 can provide more rigidity to the curved member 172 such that the bending moment increases adjacent to the bracket 174. In use, the beam 170 can be loaded within the housing 12 of the clip applier 10 such that the closure link roller 54 contacts the concave surface, and the beam 170 can be positioned at an angle such that the closure link roller 54 is farther away from the beam when the trigger 16 is initially actuated, and the closure link roller 54 becomes closer to the beam as the trigger 16 moves to the closed position. As a result, the resistance to buckling will increase as the closure link roller 54 moves thereof and the trigger 16 of the clip applier is moved to the closed position. Although not shown, multiple beams could optionally be used in a stacked fashion and the terminal or free end of the beam(s) could be contoured to tailor the buckling load at a particular point along the length of the beam.

In another exemplary embodiment, the surgical clip applier 10 can include a clip quantity indicator for indicating the number of clips remaining in the device 10. While various techniques can be used to indicate the quantity of clips remaining, FIGS. 24A-25 illustrate one exemplary embodiment of a clip quantity indicator having an indicator wheel 74 and an indicator actuator 76.

Figure 24A:
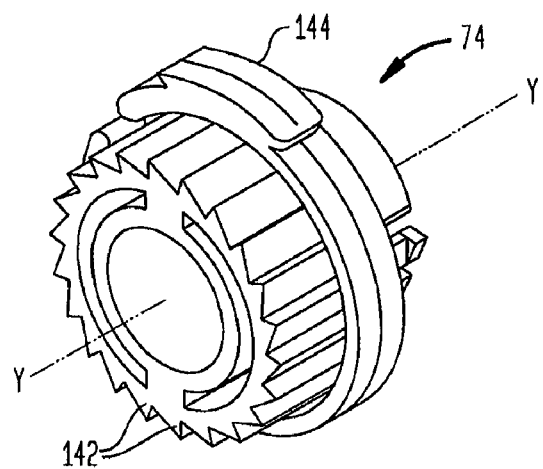
FIG. 24A is a side perspective view of a clip quantity indicator wheel of the surgical clip applier shown in FIG. 1A.
Figure 24B:
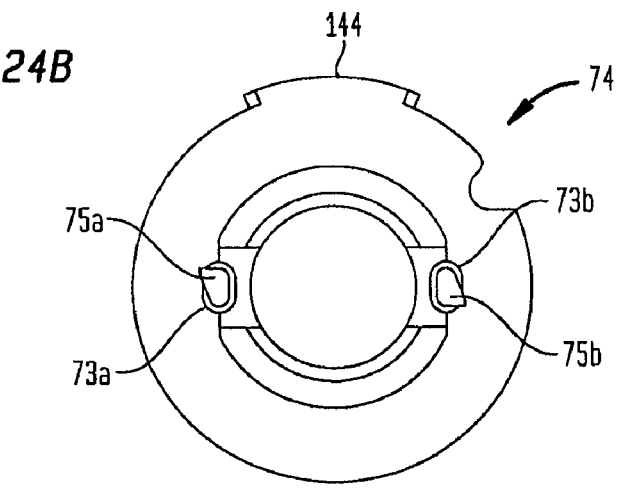
FIG. 24B is a side view of a clip quantity indicator wheel shown in FIG. 24A.

The indicator wheel 74 is shown in detail in FIGS. 24A and 24B, and as shown it has a generally circular or cylindrical shape that defines a central axis Y about which the wheel 74 is adapted to rotate. The wheel 74 includes teeth 142 formed therearound and adapted to be engaged by the indicator actuator 76, and an indicator member 144. The indicator member 144 can have a variety of configurations, but in an exemplary embodiment the indicator member 144 is in the form of a contrasting color pad having a color, e.g., orange, red, etc., that differs from the remainder of the indicator wheel 74.

Figure 25:
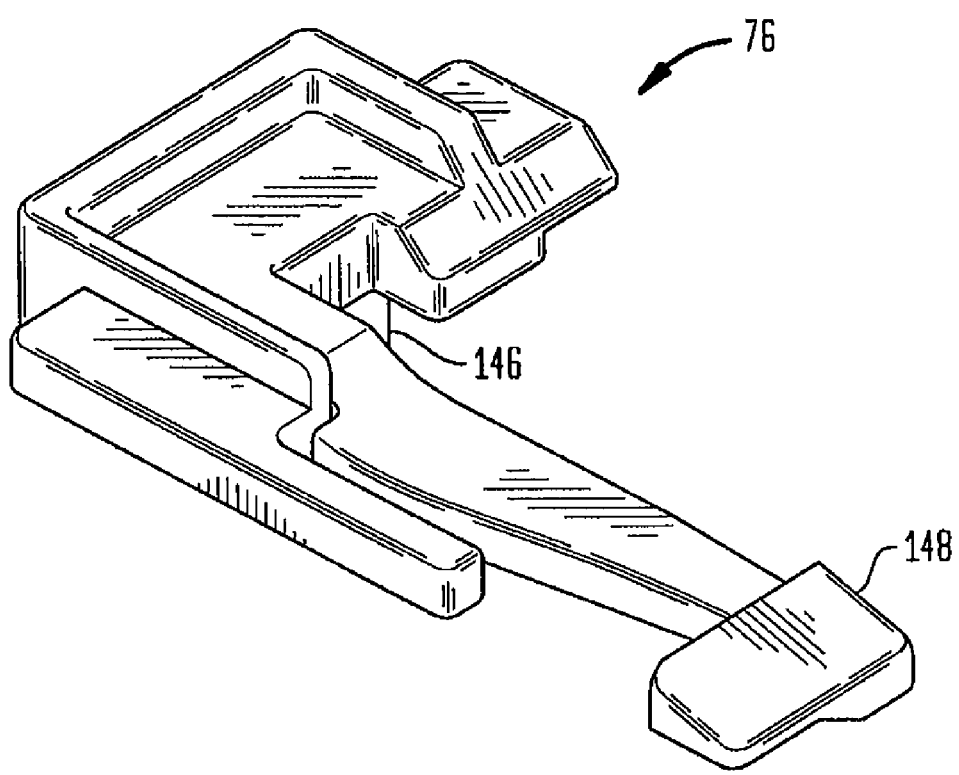
FIG. 25 is a top perspective view of a clip quantity actuator for use with the clip quantity indicator wheel shown in FIG. 24.

FIG. 25 illustrates the exemplary indicator actuator 76 in more detail. The actuator 76 is adapted to be slidably disposed within the housing 12 and to couple to the feed link coupler 50 and move as the feed bar coupler 50 and feed bar 38 are moved. Accordingly, the indicator actuator 76 can include a protrusion 146, only a portion of which is shown, formed on an inferior surface thereof for extending into the recess 50f formed between the circular flanges 50d, 50e on the feed bar coupler 50. The protrusion 146 allows the indicator actuator 76 to be engaged by the feed bar coupler 50 and moved therewith. The indicator actuator 76 can also include an engagement mechanism 148 formed thereon and adapted to engage the teeth 142 formed on the indicator wheel 74. As shown in FIG. 25, the engagement mechanism 148 on the indicator actuator 76 is in the form of an arm having a tab formed on the end thereof for engaging the teeth 142.

Figure 26A:
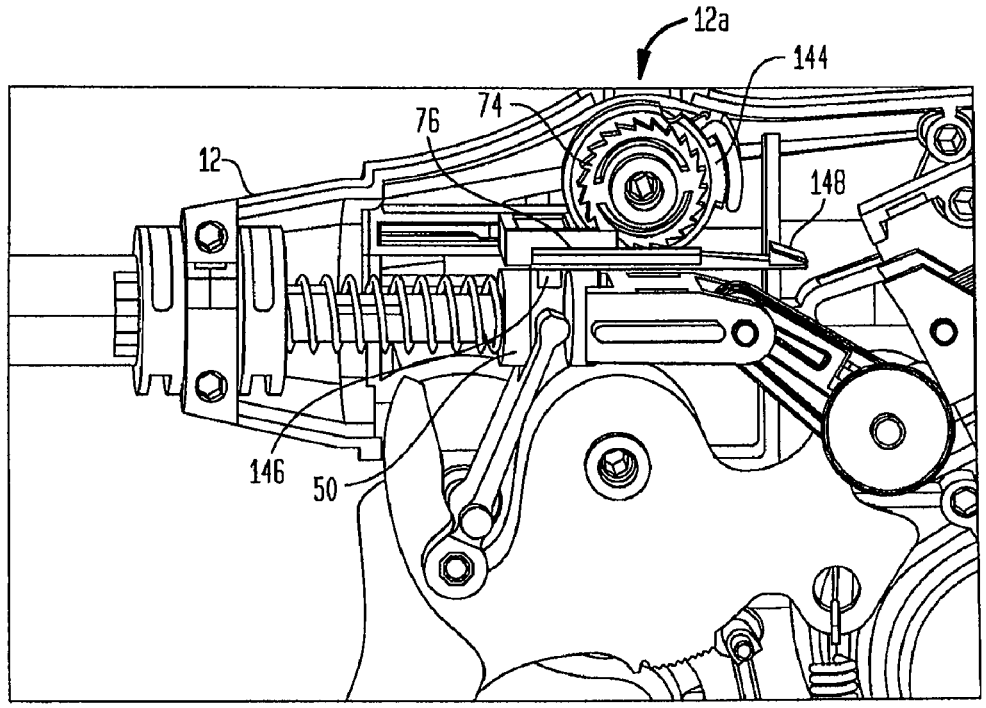
FIG. 26A is a side, partially cross-sectional view of a portion of the handle of the surgical clip applier shown in FIG. 1A, showing movement of the clip quantity actuator of FIG. 25 and the clip quantity indicator wheel of FIG. 24.
Figure 26B:
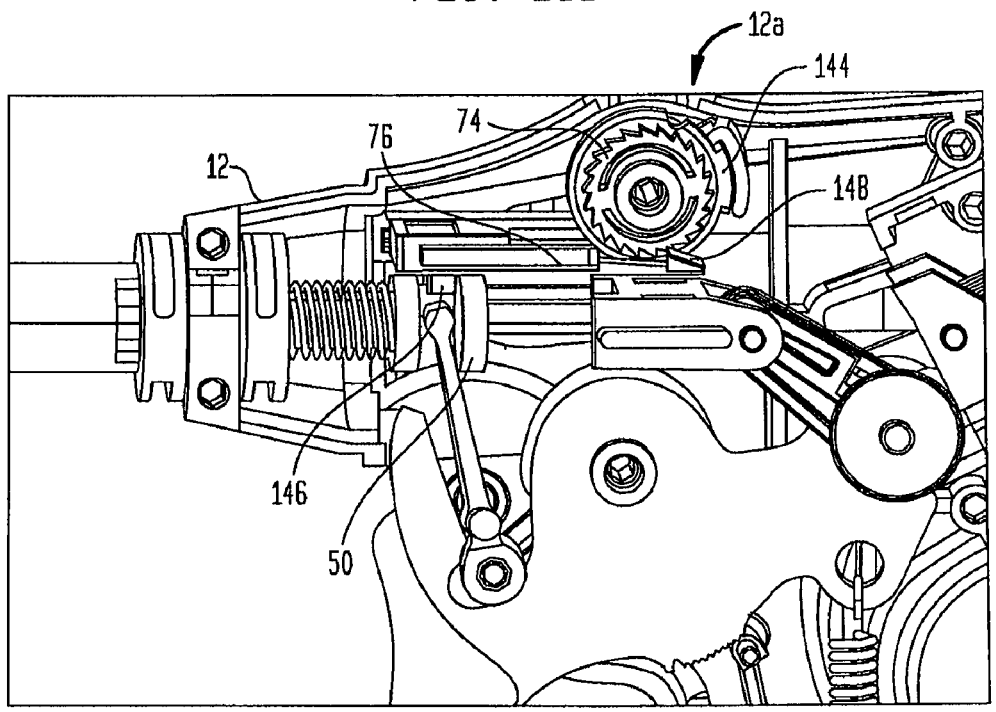
FIG. 26B is a side, partially cross-sectional view of a portion of the handle of the surgical clip applier shown in FIG. 26A, showing further movement of the clip quantity actuator of FIG. 25 and the clip quantity indicator wheel of FIG. 24.

In use, the indicator wheel 74 is rotatably disposed within the housing 12, as shown in FIGS. 26A-26B, and the indicator actuator 76 is slidably disposed within the housing 12 such that the engagement mechanism 148 is positioned adjacent to the indicator wheel 74 and the protrusion 146 extends into the feed bar coupler 50. The housing 12 includes a window 12a formed therein for providing visual access to the indicator wheel 144. As the trigger 16 is moved to the closed position and the feed bar coupler 50 is moved distally, the indicator actuator 76 will move distally with the feed bar 38 and feed bar coupler 50. As a result, the engagement mechanism 148 on the indicator actuator 76 will engage the teeth 142 on the indicator wheel 74, thereby causing the wheel 74 to rotate as a clip is advanced into the jaws 20. Each time the trigger 16 is actuated to advance a clip 20 into the jaws 20, the indicator actuator 74 rotates the indicator wheel 76. When the clip supply has two or three clips left, the contrasting color pad 144 on the indicator wheel 74 will begin to appear in the window 12a formed in the housing 12, thereby indicating to the user that only a few clips remain. The contrasting color pad 144 can be adapted to occupy the entire window 12a when the clip supply is depleted.

In another exemplary embodiment, the indicator wheel 74 can include an anti-backup mechanism that is adapted to prevent the indicator wheel 74 from rotating in a reverse direction, e.g., a counter-clockwise direction, after being advanced. While the anti-backup mechanism can have a variety of configurations, in the embodiment shown in FIG. 24B the indicator wheel 74 includes opposed arms 73a, 73b that extend substantially parallel to the axis Y. Each arm 73a, 73b has a pawl 75a, 75b formed on a distal-most end thereof that is adapted to engage corresponding teeth formed on the housing 12. While not shown, the corresponding teeth can be formed within a circular protrusion formed on an inner portion of the housing 12 adjacent to the window 12a. When the indicator wheel 74 is disposed within the housing 12, the arms 73a, 73b extend into the circular protrusion formed around the inner circumference thereof. As a clip is applied and the indicator wheel 74 is rotated, the arms 73a, 73b can deflect over the teeth in the housing to move to the next position. When the indicator actuator 76 slides proximally to return to its initial position, the arms 73a, 73b will engage the teeth in the housing to prevent the indicator wheel 74 from rotating in a reverse direction, i.e., returning to the previous position. A person skilled in the art will appreciate that a variety of other techniques can be used to prevent backup of the indicator wheel 74.

As previously mentioned, the surgical clip applier 10 can be used to apply a partially or fully closed clip to a surgical site, such as a vessel, duct, shunt, etc. In laparoscopic and endoscopic surgery, a small incision is made in the patient's body to provide access to a surgical site. A cannula or access port is typically used to define a working channel extending from the skin incision to the surgical site. Often during surgical procedures it is necessary to cease blood flow through the vessels or other ducts, and some procedures may require the use of a shunt. A surgical clip can thus be used to crimp the vessel or to secure the shunt to the vessel. Accordingly, a surgical clip applier, such as clip applier 10, can be introduced through the cannula or otherwise introduced into the surgical site to position the jaws 20 around the vessel, shunt, or other duct. The tissue stop 46 can facilitate positioning of the jaws 20 around the target site. The trigger 16 can then be actuated to cause a clip to be advanced between the jaws and positioned around the target site, and to cause the jaws 20 to close to crimp the clip. Depending on the intended use of the clip, the trigger 16 can be partially actuated, as indicated by the audible sound of the pawl 60 reaching the tock tooth 112b, or it can be fully actuated. The trigger 16 is then released to release the partially or fully closed clip, and the procedure can be repeated if necessary to apply additional clips.

Various surgical clip appliers and methods are also described in U.S. Pat. No. 7,297,149 entitled "Surgical Clip Applier Methods" and filed on Apr. 14, 2005; U.S. Pat. No. 7,288,098 entitled "Force Limiting Mechanism For Medical Instrument" and filed on Apr. 14, 2005; U.S. Pat. No. 7,261,724 entitled "Surgical Clip Advancement Mechanism" and filed on Apr. 14, 2005; U.S. Publication No. 2006/0235440 entitled "Surgical Clip Applier Ratchet Mechanism" and filed on Apr. 14, 2005; U.S. Publication No. 2006/0235441 entitled "Surgical Clip Advancement and Alignment Mechanism" and filed on Apr. 14, 2005; U.S. Publication No. 2006/0235442 entitled "Clip Applier With Migrational Resistance Features" and filed on Sep. 15, 2005; U.S. Publication No. 2006/0235443 entitled "Clip Applier Configured to Prevent Clip Fallout" and filed on Sep. 15, 2005; U.S. Publication No. 2006/0235444 entitled "Clip Advancer Mechanism With Alignment Features" and filed on Sep. 15, 2005; U.S. Publication No. 2008/0015615 entitled "Surgical Clip Advancement Mechanism" and filed on Jul. 23, 2007; U.S. Publication No. 2008/0004639 entitled "Force Limiting Mechanism for Medical Instrument" and filed on Sep. 14, 2007; U.S. Publication No. 2008/0027465 entitled "Surgical Clip Applier Methods" and filed on Oct. 9, 2007; U.S. Publication No. 2008/0027466 entitled "Surgical Clip Applier Methods" and filed on Oct. 9, 2007; and U.S. application Ser. No. 12/576,736 entitled "Improved Clip Advancer" and filed on Oct. 9, 2009, all of which are incorporated herein by reference in their entireties.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A surgical clip applier, comprising:
  a housing having a trigger movably coupled thereto and an elongate shaft extending therefrom with opposed jaws formed on a distal end thereof;
  an advancer assembly coupled to the trigger, disposed within the elongate shaft, and configured to advance one of a plurality of clips disposed within the elongate shaft into the opposed jaws, the advancer assembly being movable between a proximal position and a distal position; and
  a feeder shoe disposed within the elongate shaft and having a tang configured to engage the advancer assembly to lock the advancer assembly, and thus the trigger, in respective partially advanced positions to prevent the advancer assembly from moving to the proximal position, and thus to prevent the trigger from moving to a fully opened position, after the advancer assembly has moved to the distal position to advance a proximal-most clip into the opposed jaws.

2. The surgical clip applier of claim 1, wherein movement of the trigger from an open position to a closed position is effective to move the advancer assembly from the proximal position to the distal position.

3. The surgical clip applier of claim 1, further comprising a clip track disposed within the elongate shaft and having a plurality of clips seated therein.

4. The surgical clip applier of claim 3, wherein the feeder shoe is slidably disposed within the clip track to distally advance the plurality of clips through the clip track.

5. The surgical clip applier of claim 1, wherein the advancer assembly includes a recess formed therein that is configured to be engaged by the tang on the feeder shoe to prevent the advancer assembly from moving to the proximal position after the advancer assembly has moved a proximal-most clip into the opposed jaws.

6. The surgical clip applier of claim 5, wherein the tang on the feeder shoe is configured to move distally with the feeder shoe as the feeder shoe advances the plurality of clips through the clip track.

7. The surgical clip applier of claim 5, wherein the advancer assembly comprises a feed bar coupled to an advancer, the advancer having a distal end configured to contact and advance one of a plurality of clips into the opposed jaws.

8. The surgical clip applier of claim 7, wherein the recess is formed through a distal portion of the feed bar and a proximal portion of the advancer.

9. The surgical clip applier of claim 5, wherein a proximal portion of the tang is connected to the feeder shoe and a distal portion of the tang is disconnected from the feeder shoe and extends a distance below an inferior surface of the feeder shoe.

10. A surgical clip applier, comprising:
a handle housing having a trigger movably coupled thereto and an elongate shaft extending distally therefrom, the elongate shaft having opposed jaws on a distal end thereof;
a clip advancing assembly having a feedershoe and an advancer assembly, an inferior surface of the feeder shoe being in slidable engagement with a superior surface of the advancer assembly, and the clip advancing assembly being operatively associated with the trigger and configured to advance one of a plurality of clips disposed within the elongate shaft into the opposed jaws; and
a lockout mechanism configured to lock the clip advancing assembly in place after the clip advancing assembly has distally advanced a proximal-most clip into the opposed jaws, the clip advancing assembly configured to lock the trigger in an actuated position when the clip advancing assembly is locked in place by the lockout mechanism.

11. The surgical clip applier of claim 10, further comprising a pawl and ratchet mechanism disposed within the handle housing and operatively associated with the trigger, the pawl and ratchet mechanism having an engaged configuration in which the pawl and ratchet mechanism controls movement of the trigger and a disengaged configuration in which the trigger is movable independently of the pawl and ratchet mechanism.

12. The surgical clip applier of claim 11, wherein the lockout mechanism is configured to lock the pawl and ratchet mechanism in an engaged configuration after the clip advancing assembly has advanced a proximal-most clip into the opposed jaws to thereby lock the trigger in an actuated position.

13. The surgical clip applier of claim 11, wherein the trigger is movable in a first direction from a fully open position to a fully closed position, and a second direction from the fully closed position to the fully open position, and wherein the trigger is limited to movement in only one of the first and second directions when the pawl and ratchet mechanism are in the engaged configuration, and the trigger is freely movable in both the first and second directions when the pawl and ratchet mechanism are in the disengaged configuration.

14. The surgical clip applier of claim 11, wherein the ratchet mechanism includes a series of teeth for engaging the pawl.

15. The surgical clip applier of claim 10, wherein the lockout mechanism comprises a tang formed on the feeder shoe that is configured for locking engagement with a recess formed in the advancer assembly after the advancer assembly advances a proximal-most clip into the opposed jaws.

16. The surgical clip applier of claim 10, wherein the opposed jaws are configured to open and release a proximal-most clip before the lockout mechanism locks the clip advancing assembly.

17. A method for advancing surgical clips, comprising:
moving a trigger from an open-most position to a closed-most position to correspondingly advance a proximal-most clip of a plurality of clips into opposed jaws of a clip applier; and
releasing the trigger such that the trigger is locked in an actuated position intermediate the open-most and closed-most positions to prevent the trigger from being moved to the open-most position.

18. The method of claim 17, wherein a tang formed on a feeder shoe is engaged by a recess formed in an advancer assembly to lock the trigger.

19. The method of claim 18, wherein moving the trigger from the open-most position to the closed-most position moves the advancer assembly distally over the feeder shoe to advance the proximal-most clip into the opposed jaws of the clip applier and releasing the trigger moves the advancer assembly proximally over the feeder shoe until the recess in the advancer assembly engages the tang on the feeder shoe.

20. The method of claim 17, further comprising releasing the proximal-most clip from the opposed jaws of the clip applier before the trigger is locked in an actuated position between the open-most and closed-most positions to prevent the trigger from being moved to the open-most position.

* * * * *